United States Patent
Stevis et al.

(10) Patent No.: US 11,642,390 B2
(45) Date of Patent: May 9, 2023

(54) METHOD OF TREATMENT WITH A FUSION PROTEIN COMPRISING APELIN AND AN ANTI-APLNR ANTIBODY

(71) Applicant: Regeneron Pharmaceuticals, Inc., Tarrytown, NY (US)

(72) Inventors: Panayiotis Stevis, West Orange, NJ (US); Andrew J. Murphy, Croton-on-Hudson, NY (US); Jesper Gromada, Scarsdale, NY (US); Yonaton Ray, Bergenfield, NJ (US); Jee H. Kim, Ardsley, NY (US); Ivan B. Lobov, New York, NY (US)

(73) Assignee: Regeneran Pharmaceuticals, Inc., Tarrytown, NY (US)

( * ) Notice: Subject to any disclaimer, the term of this patent is extended or adjusted under 35 U.S.C. 154(b) by 63 days.

(21) Appl. No.: 17/167,990

(22) Filed: Feb. 4, 2021

(65) Prior Publication Data
US 2021/0403551 A1  Dec. 30, 2021

Related U.S. Application Data

(60) Division of application No. 16/218,862, filed on Dec. 13, 2018, now Pat. No. 10,947,310, which is a
(Continued)

(51) Int. Cl.
| | | |
|---|---|---|
| *A61K 39/395* | (2006.01) | |
| *A61K 38/22* | (2006.01) | |
| *A61K 38/08* | (2019.01) | |
| *A61K 38/10* | (2006.01) | |
| *A61K 47/64* | (2017.01) | |
| *A61P 9/04* | (2006.01) | |
| *A61P 9/08* | (2006.01) | |
| *A61P 9/10* | (2006.01) | |
| *C07K 16/28* | (2006.01) | |
| *C07K 7/06* | (2006.01) | |
| *C07K 7/08* | (2006.01) | |
| *C07K 14/575* | (2006.01) | |
| *C07K 19/00* | (2006.01) | |
| *C07K 14/705* | (2006.01) | |
| *C07K 14/72* | (2006.01) | |
| *A61P 37/02* | (2006.01) | |

(Continued)

(52) U.S. Cl.
CPC ............ *A61K 38/08* (2013.01); *A61K 38/10* (2013.01); *A61K 38/22* (2013.01); *A61K 39/3955* (2013.01); *A61K 47/64* (2017.08); *A61P 9/04* (2018.01); *A61P 9/08* (2018.01); *A61P 9/10* (2018.01); *C07K 16/2869* (2013.01); *A61K 38/00* (2013.01); *A61P 35/00* (2018.01); *A61P 37/02* (2018.01); *C07K 7/06* (2013.01); *C07K 7/08* (2013.01); *C07K 14/47* (2013.01); *C07K 14/575* (2013.01); *C07K 14/705* (2013.01); *C07K 14/72* (2013.01); *C07K 16/28* (2013.01); *C07K 16/46* (2013.01); *C07K 19/00* (2013.01); *C07K 2317/21* (2013.01); *C07K 2317/24* (2013.01); *C07K 2317/56* (2013.01); *C07K 2317/565* (2013.01); *C07K 2317/74* (2013.01); *C07K 2317/75* (2013.01); *C07K 2317/76* (2013.01); *C07K 2317/92* (2013.01); *C07K 2319/30* (2013.01); *C07K 2319/74* (2013.01)

(58) Field of Classification Search
CPC .. A61K 38/22; A61K 39/3955; C07K 14/575; C07K 16/2869; C07K 19/00; A61P 9/04; A61P 9/08; A61P 9/10
See application file for complete search history.

(56) References Cited

U.S. PATENT DOCUMENTS

| | | |
|---|---|---|
| 6,492,324 B1 | 12/2002 | Hinuma et al. |
| 7,736,646 B2 | 6/2010 | Krieg |

(Continued)

FOREIGN PATENT DOCUMENTS

| | | |
|---|---|---|
| CN | 102516393 | 6/2012 |
| EP | 1040189 B1 | 1/2008 |

(Continued)

OTHER PUBLICATIONS

"Product Datasheet: Anti APJ Receptor antibody ab66218," Abcam plc, 2 pages, (2013). [Retrieved from the Internet Feb. 24, 2015: <URL: http://www.abcam.com/APJ-Receptor-antibody-ab66218.pdf>], [Author Unknown].

(Continued)

*Primary Examiner* — Zachary C Howard
(74) *Attorney, Agent, or Firm* — Schwabe, Williamson & Wyatt PC; Christopher Westberg

(57) ABSTRACT

The present invention provides apelin receptor (APLNR) modulators that bind to APLNR and methods of using the same. The invention includes APLNR modulators such as antibodies, or antigen-binding fragments thereof, which inhibit or attenuate APLNR-mediated signaling. The invention includes APLNR modulators such as antibodies, or antibody fusion proteins thereof, that activate APLNR-mediated signaling. According to certain embodiments of the invention, the antibodies or antigen-binding fragments or antibody fusion proteins are fully human antibodies that bind to human APLNR with high affinity. The APLNR modulators of the invention are useful for the treatment of diseases and disorders associated with APLNR signaling and/or APLNR cellular expression, such as cardiovascular diseases, angiogenesis diseases, metabolic diseases and fibrotic diseases.

18 Claims, 3 Drawing Sheets
Specification includes a Sequence Listing.

Related U.S. Application Data continuation of application No. 15/480,199, filed on Apr. 5, 2017, now Pat. No. 10,189,901, which is a division of application No. 14/717,914, filed on May 20, 2015, now Pat. No. 9,644,018, which is a continuation-in-part of application No. PCT/US2014/066687, filed on Nov. 20, 2014.

(60) Provisional application No. 61/906,568, filed on Nov. 20, 2013.

(51) Int. Cl.
    *A61P 35/00*     (2006.01)
    *A61K 38/00*     (2006.01)
    *C07K 14/47*     (2006.01)
    *C07K 16/46*     (2006.01)

(56) References Cited

U.S. PATENT DOCUMENTS

| | | |
|---|---|---|
| 8,637,641 B2 | 1/2014 | Dahiyat et al. |
| 8,841,416 B2 | 9/2014 | Ledbetter et al. |
| 9,353,163 B2 | 5/2016 | Stevis et al. |
| 9,644,018 B2 | 5/2017 | Stevis et al. |
| 9,751,921 B2 | 9/2017 | Stevis et al. |
| 10,155,811 B2 | 12/2018 | Stevis et al. |
| 10,189,901 B2 | 1/2019 | Stevis et al. |
| 10,626,173 B2 | 4/2020 | Stevis et al. |
| 10,947,310 B2 | 3/2021 | Stevis et al. |
| 2002/0062488 A1 | 5/2002 | Doms et al. |
| 2004/0219152 A1 | 11/2004 | Krieg |
| 2005/0075275 A1 | 4/2005 | Albrecht et al. |
| 2005/0186662 A1 | 8/2005 | Low |
| 2006/0045880 A1 | 3/2006 | Krieg |
| 2006/0159676 A1 | 7/2006 | Krieg |
| 2009/0233854 A1 | 9/2009 | Fujii |
| 2010/0221255 A1 | 9/2010 | Cuttitta et al. |
| 2011/0305692 A1 | 12/2011 | Hamblin et al. |
| 2013/0196899 A1 | 8/2013 | Zecri et al. |
| 2015/0030594 A1 | 1/2015 | Yuan et al. |
| 2017/0058028 A1 | 3/2017 | Stevis et al. |

FOREIGN PATENT DOCUMENTS

| | | |
|---|---|---|
| EP | 1613348 B1 | 6/2010 |
| WO | 85/00974 A1 | 3/1985 |
| WO | 2000/014220 | 3/2000 |
| WO | 01/010912 A1 | 2/2001 |
| WO | 02/036762 A1 | 5/2002 |
| WO | 05/106493 A1 | 11/2005 |
| WO | 07/021807 A1 | 2/2007 |
| WO | 08/147143 A2 | 12/2008 |
| WO | 10/053545 A2 | 5/2010 |
| WO | 01/036489 A2 | 5/2011 |
| WO | 11/140086 A2 | 11/2011 |
| WO | 12/125408 A1 | 9/2012 |
| WO | 12/133825 A1 | 10/2012 |
| WO | 13/012855 A1 | 1/2013 |
| WO | 13/079487 A1 | 6/2013 |
| WO | 13/111110 A3 | 8/2013 |
| WO | 14/099984 A1 | 6/2014 |
| WO | 14/152955 A1 | 9/2014 |
| WO | 15/013169 A9 | 1/2015 |
| WO | 15/077491 A1 | 5/2015 |

OTHER PUBLICATIONS

"Product Datasheet: Anti APJ Receptor antibody ab97464," Abcam plc, 2 pages, (2013). [Retrieved from the Internet Feb. 24, 2015: <URL: http://www.abcam.com/APJ-Receptor-antibody-ab97464.pdf>], [Author Unknown].

"Product Datasheet: Anti-APJ Receptor antibody ab84296," Abcam plc, 4 pages, (2013). [Retrieved from the Internet Feb. 24, 2015: <URL: http://www.abcam.com/APJ-Receptor-antibody-ab84296.pdf>], [Author Unknown].

"Product Datasheet: Anti-APJ Receptor antibody ab97452," Abcam plc, 2 pages, (2013). [Retrieved from the Internet Feb. 24, 2015: <URL: http://www.abcam.com/APJ-Receptor-antibody-ab97452.pdf>], [Author Unknown].

Beck et al., "Therapeutic Fc-fusion proteins and peptides as successful alternatives to antibodies," mAbs, Landes Bioscience, 3(5):415-416, (2011).

Benjamini et al., "Immunology A Short Course, Second Edition," A John Wiley & Sons, Inc., vol. (2):40, (1991). [ISBN 0-471-56751-5].

Carter, "Introduction to current and future protein therapeutics: A protein engineering perspective", Experimental Cell Research, Academic Press, US, 317(9):1261-1269, (2011).

Cayabyab et al., "Apelin, the Natural Ligand of the Orphan Seven-Transmembrane Receptor APJ, Inhibits Human Immunodeficiency Virus Type Entry," J. Virol., 74(24):11972-11976, (2000).

Charo et al., "Endogenous regulation of cardiovascular function by apelin-APJ," Am J Physiol Heart Circ Physiol, 297:H1904-H1913, (2009).

Chen et al., "Apelin is a marker of the progression of liver fibrosis and portal hypertension in patients with biliary atresia," Pediatr Surg Int, 29:79-85, (2013).

Cheng et al., "Neuroprotection of apelin and its signaling pathway," Peptides, 37:171-173, (2012).

Claing et al., "Endocytosis of G protein-coupled receptors: roles of G protein-coupled receptor kinases and p-arresting proteins," Progress in Neurobiology, 66:61-79, (2002).

Ferrara et al., "Recombinant renewable polyclonal antibodies," Taylor & Francis Group, LLC., vol. (7.1):32-41, (2015). [www.tandfonline.com].

Hecht et al., "Rationale-Based Engineering of a Potent Long-Acting FGF21 Analog for the Treatment of Type 2 Diabetes," PLOS ONE, vol. 7, Issue 11 (e49345), Nov. 2012. [Retrieved from the Internet Jan. 18, 2018: <URL http://journals.plos.org/plosone/article?id=10.1371/journal.pone.0049345>].

Hosoya et al., "Molecular and Functional Characteristics of APJ," The Journal Of Biological Chemistry, 275(28):21061-21067, (2000).

Huang et al., "Receptor-Fc fusion therapeutics, traps, and MIMETIBODY™ technology," Current Opinion in Biotechnology, 20(6):692-699, (2009).

Iturrioz et al., "By Interacting with the C-terminal Phe of Apelin, Phe255 and Trp259 in Helix VI of the Apelin Receptor Are Critical for Internalization," The Journal Of Biological Chemistry, 285(42):32627-32637, (2010).

Iturrioz et al., "Identification and pharmacological properties of E339-3D6, the first nonpeptidic apelin receptor agonist," FASEBJ, www.fasebj.org, 24:1506-1517, (2010).

Japp et al., "Vascular Effects of Apelin In Vivo in Man," Journal of the American College of Cardiology, 52(11):908-913, (2008).

Jia et al., "Cardiovascular effects of a PEGylated apelin," Peptides, 38:181-188, (2012).

Kidoya et al., "Spatial and temporal role of the apelin/APJ system in the caliber size regulation of blood vessels during angiogenesis," The EMBO Journal, 27:522-534, (2008).

Kidoya et al., "The apelin/APJ system induces maturation of the tumor vasculature and improves the efficiency of immune therapy," Oncogene, 31:3254-3264, (2012).

Lee et al., "Characterization of Apelin, the Ligand for the APJ Receptor," J. Neurochem., 74:34-41, (2000).

Lee et al., "Modification of the Terminal Residue of Apelin-13 Antagonizes Its Hypotensive Action," Endocrinology, 146:231-236, (2005).

Lee et al., "The fate of the internalized apelin receptor is determined by different isoforms of apelin mediating differential interaction with p-arrestin," Biochemical and Biophysical Research Communications, 395:185-189, (2010).

Lee et al., "Unravelling the roles of the apelin system: prospective therapeutic applications in heart failure and obesity," Trends in Pharmacological Sciences, 27(4):190-194, (2006).

(56) References Cited

OTHER PUBLICATIONS

Li et al., "Heterodimerization of human apelin and kappa opioid receptors: Roles in signal transduction," Cellular Signaling, 24:991-1001, (2012).
Lo et al., "High level expression and secretion of Fc-X fusion proteins in mammalian cells," Protein Engineering, 11(6):495-500, (1998).
Maguire et al., "[Pyr$^1$] Apelin-13 Identified as the Predominant Apelin Isoform in the Human Heart: Vasoactive Mechanisms and Inotropic Action in Disease," Hypertension, 54:598-604, (2009).
Masri et al., "Apelin signaling: a promising pathway from cloning to pharmacology," Cellular Signaling, 17:415-426, (2005).
Medhurst et al., "Pharmacological and immunohistochemical characterization of the APJ receptor and its endogenous ligand apelin," J. Neorochem., 84:1162-1172, (2003).
Messari et al., "Functional dissociation of apelin receptor signaling and endocytosis: implications for the effects of apelin on arterial blood pressure," J. Neurochem., 90:1290-1301, (2004).
Murza et al., "Elucidation of the Structure-Activity Relationships of Apelin: Influence of Unnatural Amino Acids on Binding, Signaling, and Plasma Stability," ChemMedChem, 7(2):318-325, (2012).
Murza et al., "Stability and Degradation Patterns of Chemically Modified Analogs of Apelin-13 in Plasma and Cerebrospinal Fluid," Peptide Science, 102(4):297-303, (2014).
Nishimura et al., "A novel system for the preparation of orphan receptor ligand peptides," J. Chem. Soc., Perkin Trans. 1, Royal Society of Chemistry, GB, 16:1960-1968, (2001).
PCT WO 04/081198 A2 Sep. 23, 2004 Arizona Board of Regents on Behalf of the University of Arizona.
Pisarenko et al., "Effects of structural analogues of apelin-I2 in acute myocardial infarction in rats," J Pharmacol Pharmacother, Epub before print, 13 pages, (2013).
Pisarenko et al., "In Vivo Reduction of Reperfusion Injury to the Heart with Apelin-12 Peptide in Rats," Bulletin of Experimental Biology and Medicine, 152(1):79-82, (2011). [Translated from Byulleten' Eksperimental'noi Biologii i Meditsiny, 152(7):79-82, (2011).].
Pitkin et al., "Modulation of the apelin/APJ system in heart failure and atherosclerosis in man," British Journal of Pharmacology, 160:1785-1795, (2010).
Puffer et al., "Expression and Coreceptor Function of APJ for Primate Immunodeficiency Viruses," Virology, vol. 276:435-444, (2000). DOI: 10.1006/viro.2000.0557; available online at http://www.idealibrary.com.
Sato et al., "Therapeutic peptides: technological advances driving peptides into development", Current Opinion In Biotechnology, GB, 17(6): 638-642, (2006).
Shimamoto et al., "Peptibodies A flexible alternative format to antibodies," mAbs 4(5): 586-591, (2012).
Siddiquee et al., "The apelin receptor inhibits the angiotensin II type 1 receptor via allosteric trans-inhibition," Br J Pharmacol, Epub before print, doi: 10.1111/j.1476-5381.2012.02192.x, 168(5):1104-1117, (2013).
Sidorova et al., "Synthesis and Cardioprotective Properties of Apelin-12 and its Structural Analogues," Russian Journal of Bioorganic Chemistry, 38(1):30-411, (2012).
Sun et al., "Non-activated APJ suppresses the angiotensin II type 1 receptor, whereas apelin-activated APJ acts conversely," Hypertension Research, 34:701-706, (2011).
U.S. Appl. No. 14/212,753, Final Office Action dated Sep. 21, 2015.
U.S. Appl. No. 14/212,753, Non-Final Office Action dated Mar. 18, 2015.
U.S. Appl. No. 14/212,753, Notice of Allowance dated Feb. 4, 2016.
U.S. Appl. No. 14/717,914, Final Office Action dated Nov. 23, 2016.
U.S. Appl. No. 14/717,914, Non-Final Office Action dated Jul. 13, 2016.
U.S. Appl. No. 14/717,914, Notice of Allowance dated Jan. 4, 2017.
U.S. Appl. No. 14/717,914, Requirement for Restriction/Election dated Feb. 12, 2016.
U.S. Appl. No. 15/038,202, Final Office Action dated Apr. 10, 2018.
U.S. Appl. No. 15/038,202, Non-Final Office Action dated May 12, 2017.
U.S. Appl. No. 15/038,202, Non-Final Office Action dated Nov. 8, 2017.
U.S. Appl. No. 15/038,202, Notice of Allowance dated Jul. 30, 2018.
U.S. Appl. No. 15/038,202, Requirement for Restriction/Election dated Dec. 13, 2016.
U.S. Appl. No. 15/146,730, Non-Final Office Action dated Dec. 6, 2016.
U.S. Appl. No. 15/146,730, Notice of Allowance dated May 1, 2017.
U.S. Appl. No. 15/480,199, Notice of Allowance dated Sep. 13, 2018.
U.S. Appl. No. 15/480,199, Requirement for Restriction/Election dated Oct. 5, 2017.
U.S. Appl. No. 15/480,199, Requirement for Restriction/Election dated Mar. 28, 2018.
U.S. Appl. No. 15/665,973, Final Office Action dated Mar. 4, 2019.
U.S. Appl. No. 15/665,973, Non-Final Office Action dated Aug. 24, 2018.
U.S. Appl. No. 16/175,357, Requirement for Restriction/Election dated Mar. 20, 2019.
U.S. Appl. No. 16/175,357, Non-Final Office Action dated Jul. 25, 2019.
U.S. Appl. No. 15/665,973, Non-Final Office Action dated Aug. 19, 2019.
U.S. Appl. No. 16/175,357, Notice of Allowance dated Dec. 17, 2019.
U.S. Appl. No. 16/218,862, Requirement for Restriction/Election dated Jan. 23, 2020.
U.S. Appl. No. 16/218,862, Non-Final Office Action dated Jun. 15, 2020.
U.S. Appl. No. 16/218,862, Notice of Allowance dated Nov. 5, 2020.
Vickers et al., "Hydrolysis of Biological Peptides by Human Angiotensin-Converting Enzyme-Related Carboxypeptidase (ACE2)," J Biol Chem, 277:14838-14843, (2002).
Wang et al., "Loss of Apelin Exacerbates Myocardial Infarction Adverse Remodeling and Ischemia reperfusion Injury: Therapeutic Potential of Synthetic Apelin Analogues," J Am Heart Assoc., 2:e000249, doi: 10.1161/JAHA.113.000249, 34 pages, (2013).
WIPO Application No. PCT/US2014/028384, PCT International Preliminary Report on Patentability dated Sep. 24, 2015.
WIPO Application No. PCT/US2014/028384, PCT International Search Report and Written Opinion of the International Searching Authority dated Jan. 28, 2014.
WIPO Application No. PCT/US2014/066687, PCT International Preliminary Report on Patentability dated Jun. 2, 2016.
WIPO Application No. PCT/US2014/066687, PCT International Search Report and Written Opinion of the International Searching Authority dated May 13, 2015.
WIPO Application No. PCT/US2014/066687, PCT Invitation to Pay Additional Fees dated Mar. 6, 2015.
Zhang et al., "Identifying structural determinants of potency for analogs of apelin-13: Integration of C-terminal truncation with structure-activity," Bioorg & Med. Chem., 22:2992-2997, (2014).

METHOD OF TREATMENT WITH A FUSION PROTEIN COMPRISING APELIN AND AN ANTI-APLNR ANTIBODY

STATEMENT OF RELATED PATENT APPLICATIONS

This application is a division of U.S. application Ser. No. 16/218,862, filed Dec. 13, 2018, which is a continuation of U.S. application Ser. No. 15/480,199, filed Apr. 5, 2017, now U.S. Pat. No. 10,189,901, which is a division of U.S. application Ser. No. 14/717,914, filed May 20, 2015, now U.S. Pat. No. 9,644,018, which is a continuation-in-part of International Application No. PCT/US2014/066687, filed Nov. 20, 2014, which claims the benefit under 35 USC § 119(e) of U.S. Provisional Application No. 61/906,568, filed Nov. 20, 2013. Each of these applications is incorporated herein by reference in its entirety for all purposes.

SEQUENCE LISTING

This application incorporates by reference the Sequence Listing submitted in Computer Readable Form as file 7410US06-Sequence.txt created on Feb. 4, 2021 and containing 160,849 bytes.

FIELD OF THE INVENTION

The present invention relates to apelin receptor (APLNR) modulators that are antibodies, antibody-fusion proteins or antigen-binding fragments thereof, which are specific for human APLNR, and methods of use thereof.

BACKGROUND

Preproapelin is a 77 amino acid protein expressed in the human CNS and peripheral tissues, e.g. lung, heart, and mammary gland. Peptides comprising C-terminal fragments of varying size of apelin peptide were shown to activate the G protein—coupled receptor, APJ receptor (now known as APLNR) (Habata, et al., 1999, *Biochem Biophys Acta* 1452: 25-35; Hosoya, et al., 2000, JBC, 275(28):21061-67; Lee, et al., 2000, *J Neurochem* 74:34-41; Medhurst, et al., 2003, *J Neurochem* 84:1162-1172). Many studies indicate that apelin peptides and analogues convey cardiovascular and angiogenic actions through their interaction with the APJ receptor (APLNR), such as endothelium-dependent vasodilation (Tatemoto et al., 2001, *Regul Pept* 99:87-92).

APLNR is a Class A (rhodopsin-like) G protein-coupled receptor (GPCR). Although monoclonal antibodies offer an alternative approach to small molecule compounds or peptidomimetics for modulating APLNR, a number of factors make it particularly difficult to generate therapeutic antibodies that bind to and modulate GPCRs. For one, target epitopes (ligand binding domains) of a GPCR are often embedded in the plasma membrane. Furthermore, generating an immune response to GPCR proteins in host animals can be problematic since mammals share high structural homology for these membrane proteins and therefore may not recognize the GPCR antigen as foreign (Herr, D R, 2012 Intl Rev *Cell Mol Biol* 297:45-81). Still, antibodies to GPCRs remain promising for therapeutic intervention if the antibody can instill an active or nonactive conformation (e.g. agonism or antagonism) of the receptor or prevent (neutralize) binding of the receptor's endogenous ligand.

The apelin system appears to play a role in pathophysiological angiogenesis. Studies have indicated that apelin may be involved in hypoxia-induced retinal angiogenesis (Kasai et al., 2010, *Arterioscler Thromb Vasc Bioi* 30:2182-2187). In some reports, certain compositions may inhibit angiogenesis by inhibiting the apelin/APJ pathway (see, e.g., U.S. Pat. No. 7,736,646), such as APLNR inhibitors capable of blocking pathological angiogenesis and therefore useful in inhibiting tumor growth or vascularization in the retina (Kojima, Y. and Quertermous, T., 2008, *Arterioscler Thromb Vasc Biol;* 28; 1687-1688; Rayalam, S. et al. 2011, *Recent Pat Anticancer Drug Discov* 6(3):367-72). As such, interference with apelin-mediated signaling may also be beneficial in early prevention of proliferative diabetic retinopathy (Tao et al., 2010, *Invest Opthamol Visual Science* 51:4237-4242; Lu, Q. et al, 2013, *PLoS One* 8(7):e69703).

Apelin has also been reported in the regulation of insulin and mechanisms of diabetes and obesity-related disorders. In mouse models of obesity, apelin is released from adipocytes and is directly upregulated by insulin (Boucher, et al., 2005, *Endocrinol* 146:1764-71). Apelin knockout mice demonstrate diminished insulin sensitivity (Yue, et al., 2010, *Am J Physiol Endocrinol Metab* 298:E59-E67).

Furthermore, APLNR agonists may mimick apelin-induced vasodilation and angiogenesis to be protective in ischemia-reperfusion injury and improve cardiac function in conditions such as congestive heart failure, myocardial infarction, and cardiomyopathy. Therapeutic administration of apelin peptides reportedly contributes to the promotion of angiogenesis and functional recovery from ischemia. (Eyries M, et al., 2008, *Circ Res* 103:432-440; Kidoya H, et al., 2010, *Blood* 115:3166-3174). The small molecule E339-3D6, which behaves as a partial agonist with respect to cAMP production, induces vasorelaxation in an ex vivo precontracted rat aorta model (Iturrioz, X, et al., 2010 FASEB 24(5):1506-1517).

APLNR signaling, and modulation thereof, has been implicated as a factor in a variety of diseases and disorders (e.g. WO2004081198A2, published on 23 Sep. 2004), and there is still a need for therapeutic agents that modulate APLNR biological activity.

BRIEF SUMMARY OF THE INVENTION

The present invention provides APLNR modulators that bind human apelin receptor ("APLNR"). The APLNR modulators of the invention are useful, inter alia, for activating or inhibiting APLNR-mediated signaling and for treating diseases and disorders related to APLNR activity and/or signaling.

The APLNR modulators of the invention include antibodies, antibody-fusion proteins, and antigen-binding fragments thereof.

The antibodies and antibody-fusion proteins of the invention can be full-length (for example, an IgG1, IgG2 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, *J. Immunol.* 164: 1925-1933).

The present invention provides antibodies, antibody-fusion proteins or antigen-binding fragments thereof comprising a heavy chain variable region (HCVR) having an amino acid sequence selected from the group consisting of SEQ ID NO: 2, 18, 34, 50, 66, 82, 98, 114, 130, 146, 162, 178, 194, 210, 287, 303, 319, 335, 351, and 367, or a substantially similar sequence thereof having at least 90%, at least 95%, at least 98% or at least 99% sequence identity.

The present invention also provides an antibody, antibody-fusion protein or antigen-binding fragment of an antibody comprising a light chain variable region (LCVR) having an amino acid sequence selected from the group consisting of SEQ ID NO: 10, 26, 42, 58, 74, 90, 106, 122, 138, 154, 170, 186, 202, 218, 295, 311, 327, 343, 359, and 375, or a substantially similar sequence thereof having at least 90%, at least 95%, at least 98% or at least 99% sequence identity.

The present invention also provides an antibody, antibody-fusion protein or antigen-binding fragment thereof comprising a HCVR and LCVR (HCVR/LCVR) sequence pair selected from the group consisting of SEQ ID NO: 2/10, 18/26, 34/42, 50/58, 66/74, 82/90, 98/106, 114/122, 130/138, 146/154, 162/170, 178/186, 194/202, 210/218, 287/295, 303/311, 319/327, 335/343, 351/359, and 367/375.

The present invention also provides an antibody, antibody-fusion protein or antigen-binding fragment of an antibody comprising a heavy chain CDR3 (HCDR3) domain having an amino acid sequence selected from the group consisting of SEQ ID NO: 8, 24, 40, 56, 72, 88, 104, 120, 136, 152, 168, 184, 200, 216, 293, 309, 325, 341, 357 and 373, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 16, 32, 48, 64, 80, 96, 112, 128, 144, 160, 176, 192, 208, 224, 301, 317, 333, 349, 365, and 381, or a substantially similar sequence thereof having at least 90%, at least 95%, at least 98% or at least 99% sequence identity.

In certain embodiments, the antibody, antibody-fusion protein or antigen-binding portion of an antibody comprises a HCDR3/LCDR3 amino acid sequence pair selected from the group consisting of SEQ ID NO: 8/16, 24/32, 40/48, 56/64, 72/80, 88/96, 104/112, 120/128, 136/144, 152/160, 168/176, 184/192, 200/208, 216/224, 393/301, 309/317, 325/333, 341/349, 357/365, and 373/381.

The present invention also provides an antibody, antibody-fusion protein or fragment thereof further comprising a heavy chain CDR1 (HCDR1) domain having an amino acid sequence selected from the group consisting of SEQ ID NO: 4, 20, 36, 52, 68, 84, 100, 116, 132, 148, 164, 180, 196, 212, 289, 305, 321, 337, 353, and 369, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54, 70, 86, 102, 118, 134, 150, 166, 182, 198, 214, 291, 307, 323, 339, 355, and 371, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60, 76, 92, 108, 124, 140, 156, 172, 188, 204, 220, 297, 313, 329, 345, 361, and 377 or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62, 78, 94, 110, 126, 142, 158, 174, 190, 206, 222, 299, 315, 331, 347, 363, and 379, or a substantially similar sequence thereof having at least 90%, at least 95%, at least 98% or at least 99% sequence identity.

Certain non-limiting, exemplary antibodies, antibody-fusion proteins and antigen-binding fragments of the invention comprise HCDR1-HCDR2-HCDR3-LCDR1-LCDR2-LCDR3 domains, respectively, having the amino acid sequences selected from the group consisting of: SEQ ID NOs: 4-6-8-12-14-16 (e.g. H1M9207N); 20-22-24-28-30-32 (e.g. H2aM9209N); 36-38-40-44-46-48 (e.g. H2aM9222N); 52-54-56-60-62-64 (e.g. H2aM9227N); 68-70-72-76-78-80 (e.g. H2aM9228N); 84-86-88-92-94-96 (e.g. H2aM9230N); 100-102-104-108-110-112 (e.g. H2aM9232N); 116-118-120-124-126-128 (e.g. H4H9092P); 132-134-136-140-142-144 (e.g. H4H9093P); 148-150-152-156-158-160 (e.g., H4H9101P); 164-166-168-172-174-176 (e.g. H4H9103P); 180-182-184-188-190-192 (e.g., H4H9104P); 196-198-200-204-206-208 (e.g. H4H9112P); 212-214-216-220-222-224 (e.g. H4H9113P); 289-291-293-297-299-301 (e.g. H2aM9221N); 305-307-309-313-315-317 (e.g. H2aM9223N); 321-323-325-329-331-333 (e.g. H2aM9226N); 337-339-341-345-347-349 (e.g. H2aM9229N); 353-355-357-361-363-365 (e.g. H2aM9224N); and 369-371-373-377-379-381 (e.g. H2aM9225N).

In a related embodiment, the invention includes an antibody, antibody-fusion protein or antigen-binding fragment of an antibody which specifically binds APLNR, wherein the antibody, antibody-fusion protein or antigen-binding fragment comprises the heavy and light chain CDR domains contained within heavy and light chain variable region (HCVR/LCVR) sequences selected from the group consisting of SEQ ID NO: 2/10, 18/26, 34/42, 50/58, 66/74, 82/90, 98/106, 114/122, 130/138, 146/154, 162/170, 178/186, 194/202, 210/218, 287/295, 303/311, 319/327, 335/343, 351/359, and 367/375. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., 1997, *J. Mol. Biol.* 273:927-948; and Martin et al., 1989, *Proc. Natl. Acad. Sci. USA* 86:9268-9272. Public databases are also available for identifying CDR sequences within an antibody.

The present invention also provides an antibody-fusion protein or fragment thereof further comprising an apelin peptide. Certain non-limiting, exemplary antibody-fusion proteins of the invention comprise heavy and light chain variable region (HCVR/LCVR) sequences selected from the group consisting of SEQ ID NO: 2/10, 18/26, 34/42, 50/58, 66/74, 82/90, 98/106, 114/122, 130/138, 146/154, 162/170, 178/186, 194/202, 210/218, 287/295, 303/311, 319/327, 335/343, 351/359, and 367/375; and further comprise an apelin peptide sequence, e.g. a fragment or analogue of SEQ ID NO: 227, SEQ ID NO: 228, SEQ ID NO: 229 or SEQ ID NO: 230. In certain embodiments, the apelin peptide sequence, or fragment or analogue thereof, comprises the amino acid sequence selected from the group consisting of SEQ ID NO: 227, SEQ ID NO: 228, SEQ ID NO: 229, SEQ ID NO: 230, SEQ ID NO: 262, SEQ ID NO: 269, SEQ ID NO: 270, SEQ ID NO: 271, SEQ ID NO: 272, SEQ ID NO: 273, SEQ ID NO: 283, SEQ ID NO: 284, and SEQ ID NO: 285.

The present invention provides antibody-fusion proteins or antigen-binding fragments thereof comprising a heavy chain (HC) having an amino acid sequence selected from the group consisting of SEQ ID NO: 239, 241, 243, 245, 247, 253, 255, 257, 259, 274, 275, 276, 277, 278, 279, 280, 281, and 282, or a substantially similar sequence thereof having at least 90%, at least 95%, at least 98% or at least 99% sequence identity.

The present invention also provides an antibody-fusion protein or antigen-binding fragment of an antibody-fusion protein comprising a light chain (LC) having an amino acid sequence selected from the group consisting of SEQ ID NO: 235, 237, 249, and 251, or a substantially similar sequence thereof having at least 90%, at least 95%, at least 98% or at least 99% sequence identity.

The present invention also provides an antibody-fusion protein or antigen-binding fragment thereof comprising a HC and LC (HC/LC) amino acid sequence pair selected from the group consisting of SEQ ID NO: 130/235, 130/237, 239/138, 241/138, 243/138, 245/138, 247/122, 114/249, 114/251, 253/26, 255/26, 257/26, 259/26, 274/138, 275/138, 276/138, 277/138, 278/138, 279/26, 280/26, 281/26, and 282/26.

Certain non-limiting, exemplary antibody-fusion proteins comprise (i) an immunoglobulin (Ig) molecule and (ii) an apelin peptide, or analogue thereof. In some embodiments, the IgG molecule is an anti-APLNR antibody as described herein. In further embodiments, the apelin peptide comprises the amino acid sequence selected from the group consisting of SEQ ID NO: 227, SEQ ID NO: 228, SEQ ID NO: 229 or SEQ ID NO: 230, or comprises a fragment or analogue of the amino acid sequence selected from the group consisting of SEQ ID NO: 227, SEQ ID NO: 228, SEQ ID NO: 229 or SEQ ID NO: 230.

Another aspect of the invention provides a protein comprising N'-P1-X1(n)-Al-C' or N'-Al-X1 (n)-P1-C', wherein N' is the N-terminus and C' is the C-terminus of the polypeptide; P1 comprises an amino acid sequence selected from the group consisting of an HCVR, an LCVR, a heavy chain, a light chain, and an HCVR/LCVR ScFv sequence; Al comprises an apelin peptide, or an analogue thereof; and X1 is a peptide linker; wherein n=0 to 10.

In some embodiments, the apelin peptide, or analogue thereof comprises apelin40-77 (apelin-38), apelin42-77 (apelin-36), apelin43-77 (apelin-35), apelin47-77 (apelin-31), apelin59-77 (apelin-19), apelin61-77 (apelin-17), apelin63-77 (apelin-15), apelin64-77 (apelin-14), apelin65-77 (apelin-13), apelin66-77 (apelin-12, or Al2), apelin67-77 (apelin-11), apelin68-77 (apelin-10), apelin73-77 (apelin-5), apelin61-76 (apelin-K16P), apelin61-75 (apelin-K15M), apelin61-74 (apelin-K14P), or [Pyr1]Apelin-13.

According to certain embodiments, the antibody-fusion protein or antigen-binding fragment thereof comprises the heavy and light chain sequences encoded by the amino acid sequences of SEQ ID NOs: 130 and 235 (e.g. H4H9093P-1-NVK3), 130 and 237 (e.g. H4H9093P-2-CVK3), 239 and 138 (e.g. H4H9093P-3-NVH3), 241 and 138 (e.g. H4H9093P-4-NVH0), 243 and 138 (e.g. H4H9093P-5-NVH1), 245 and 138 (e.g. H4H9093P-6-NVH2), 247 and 122 (e.g. H4H9092P-1-NVH3), 114 and 249 (e.g. H4H9092P-2-NVK3), 114 and 251 (e.g. H4H9092P-3-CVK3), 253 and 26 (e.g. H4H9209N-1-NVH0), 255 and 26 (e.g. H4H9209N-2-NVH1), 257 and 26 (e.g. H4H9209N-3-NVH2), 259 and 26 (e.g. H4H9209N-4-NVH3), 274 and 138 (e.g. H4H9093P-APN9-(G4S)3), 275 and 138 (e.g. H4H9093P-APN10-(G4S)3), 276 and 138 (e.g. H4H9093P-APN11-(G4S)3), 277 and 138 (e.g. H4H9093P-APN11+S-(G4S)3), 278 and 138 (e.g. H4H9093P-APNV5-11-(G4S)3), 279 and 26 (e.g. H4H9209N-APN9-(G4S)3), 280 and 26 (e.g. H4H9209N-APN10-(G4S)3), 281 and 26 (e.g. H4H9209N-APN11-(G4S)3), or 282 and 26 (e.g. H4H9209N-APN11+S-(G4S)3).

In another aspect, the invention provides nucleic acid molecules encoding anti-APLNR antibodies, antibody-fusion proteins or antigen-binding fragments thereof. Recombinant expression vectors carrying the nucleic acids of the invention, and host cells into which such vectors have been introduced, are also encompassed by the invention, as are methods of producing the antibodies or antibody-fusion proteins by culturing the host cells under conditions permitting production of the antibodies, and recovering the antibodies or antibody-fusion proteins produced.

In one embodiment, the invention provides an antibody, antibody-fusion protein or antigen-binding fragment thereof comprising a HCVR encoded by a nucleic acid sequence selected from the group consisting of SEQ ID NO: 1, 17, 33, 49, 65, 81, 97, 113, 129, 145, 161, 177, 193, 209, 286, 302, 318, 334, 350, and 366, or a substantially identical sequence having at least 90%, at least 95%, at least 98%, or at least 99% homology thereof.

The present invention also provides an antibody, antibody-fusion protein or antigen-binding fragment thereof comprising a LCVR encoded by a nucleic acid sequence selected from the group consisting of SEQ ID NO: 9, 25, 41, 57, 73, 89, 105, 121, 137, 153, 169, 185, 201, 217, 294, 310, 326, 342, 358, and 374, or a substantially identical sequence having at least 90%, at least 95%, at least 98%, or at least 99% homology thereof.

The present invention also provides an antibody, antibody-fusion protein or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 292, 308, 324, 340, 356, and 372, or a substantially identical sequence having at least 90%, at least 95%, at least 98%, or at least 99% homology thereof; and a LCDR3 domain encoded by a nucleotide sequence selected from the group consisting of SEQ ID NO: 15, 31, 47, 63, 79, 95, 111, 127, 143, 159, 175, 191, 207, 223, 300, 316, 332, 348, 364, and 380, or a substantially identical sequence having at least 90%, at least 95%, at least 98%, or at least 99% homology thereof.

The present invention also provides an antibody, antibody-fusion protein or antigen-binding fragment thereof which further comprises a HCDR1 domain encoded by a nucleotide sequence selected from the group consisting of SEQ ID NO: 3, 19, 35, 51, 67, 83, 99, 115, 131, 147, 163, 179, 195, 211, 288, 304, 320, 336, 352 and 368, or a substantially identical sequence having at least 90%, at least 95%, at least 98%, or at least 99% homology thereof; a HCDR2 domain encoded by a nucleotide sequence selected from the group consisting of SEQ ID NO: 5, 21, 37, 53, 69, 85, 101, 117, 133, 149, 165, 181, 197, 213, 290, 306, 322, 338, 354, and 370, or a substantially identical sequence having at least 90%, at least 95%, at least 98%, or at least 99% homology thereof; a LCDR1 domain encoded by a nucleotide sequence selected from the group consisting of SEQ ID NO: 11, 27, 43, 59, 75, 91, 107, 123, 139, 155, 171, 187, 203, 219, 296, 312, 328, 344, 360, and 376, or a substantially identical sequence having at least 90%, at least 95%, at least 98%, or at least 99% homology thereof; and a LCDR2 domain encoded by a nucleotide sequence selected from the group consisting of SEQ ID NO: 13, 29, 45, 61, 77, 93, 109, 125, 141, 157, 173, 189, 205, 221, 298, 314, 330, 346, 362, and 378, or a substantially identical sequence having at least 90%, at least 95%, at least 98%, or at least 99% homology thereof.

According to certain embodiments, the antibody, antibody-fusion protein or antigen-binding fragment thereof comprises the heavy and light chain CDR sequences encoded by the nucleic acid sequences of SEQ ID NOs: 1 and 9 (e.g. H1M9207N), 17 and 25 (e.g. H2aM9209N), 33 and 41 (e.g. H2aM9222N), 49 and 57 (e.g. H2aM9227N), 65 and 73 (e.g. H2aM9228N), 81 and 89 (e.g. H2aM9230N), 97 and 105 (e.g. H2aM9232N), 113 and 121 (e.g. H4H9092P), 129 and 137 (e.g. H4H9093P), 145 and 153 (e.g. H4H9101P), 161 and 169 (e.g. H4H9103P), 177 and 185 (e.g. H4H9104P), 193 and 201 (e.g. H4H9112P), 209 and 217 (e.g. H4H9113P), 286 and 294 (e.g. H2M9221N), 302 and 310 (e.g. H2M9223N), 318 and 326 (e.g. H2M9226N), 334 and 342 (e.g. H2M9229N), 350 and 358 (e.g. H2M9224N), or 366 and 374 (e.g. H2M9225N).

In one embodiment, the invention provides an antibody-fusion protein or antigen-binding fragment thereof comprising a heavy chain (HC) encoded by a nucleic acid sequence selected from the group consisting of SEQ ID NO: 238, 240, 242, 244, 246, 252, 254, 256, and 258, or a substantially identical sequence having at least 90%, at least 95%, at least 98%, or at least 99% homology thereof.

The present invention also provides an antibody-fusion protein or antigen-binding fragment thereof comprising a light chain (LC) encoded by a nucleic acid sequence selected from the group consisting of SEQ ID NO: 234, 236, 248, and 250, or a substantially identical sequence having at least 90%, at least 95%, at least 98%, or at least 99% homology thereof.

According to certain embodiments, the antibody-fusion protein or antigen-binding fragment thereof comprises the heavy and light chain sequences encoded by the nucleic acid sequences of SEQ ID NOs: 129 and 234 (e.g. H4H9093P-1-NVK3), 129 and 236 (e.g. H4H9093P-2-CVK3), 238 and 137 (e.g. H4H9093P-3-NVH3), 240 and 137 (e.g. H4H9093P-4-NVH0), 242 and 137 (e.g. H4H9093P-5-NVH1), 244 and 137 (e.g. H4H9093P-6-NVH2), 246 and 121 (e.g. H4H9092P-1-NVH3), 113 and 248 (e.g. H4H9092P-2-NVK3), 113 and 250 (e.g. H4H9092P-3-CVK3), 252 and 25 (e.g. H4H9209N-1-NVH0), 254 and 25 (e.g. H4H9209N-2-NVH1), 256 and 25 (e.g. H4H9209N-3-NVH2), or 258 and 25 (e.g. H4H9209N-4-NVH3).

In other embodiments, the antibody-fusion protein comprises nucleic acid molecules encoding the heavy and light chain amino acid pairs selected from the group consisting of SEQ ID NOs: 130 and 235 (e.g. H4H9093P-1-NVK3), 130 and 237 (e.g. H4H9093P-2-CVK3), 239 and 138 (e.g. H4H9093P-3-NVH3), 241 and 138 (e.g. H4H9093P-4-NVH0), 243 and 138 (e.g. H4H9093P-5-NVH1), 245 and 138 (e.g. H4H9093P-6-NVH2), 247 and 122 (e.g. H4H9092P-1-NVH3), 114 and 249 (e.g. H4H9092P-2-NVK3), 114 and 251 (e.g. H4H9092P-3-CVK3), 253 and 26 (e.g. H4H9209N-1-NVH0), 255 and 26 (e.g. H4H9209N-2-NVH1), 257 and 26 (e.g. H4H9209N-3-NVH2), 259 and 26 (e.g. H4H9209N-4-NVH3), 274 and 138 (e.g. H4H9093P-APN9-(G4S)3), 275 and 138 (e.g. H4H9093P-APN10-(G4S)3), 276 and 138 (e.g. H4H9093P-APN11-(G4S)3), 277 and 138 (e.g. H4H9093P-APN11+S-(G4S)3), 278 and 138 (e.g. H4H9093P-APNV5-11-(G4S)3), 279 and 26 (e.g. H4H9209N-APN9-(G4S)3), 280 and 26 (e.g. H4H9209N-APN10-(G4S)3), 281 and 26 (e.g. H4H9209N-APN11-(G4S)3), or 282 and 26 (e.g. H4H9209N-APN11+S-(G4S) 3).

According to other embodiments, the invention provides a first polynucleotide and a second polynucleotide which together encode an antibody-fusion protein. The invention further provides a cell comprising a first polynucleotide and a second polynucleotide which together encode an antibody-fusion protein. In some embodiments, the first and second polynucleotides are a part of the same nucleic acid molecule or different nucleic acid molecules in the cell.

In certain examples, the first polynucleotide encodes a polypeptide comprising (i) a heavy chain variable region (HCVR) having an amino acid sequence selected from the group consisting of SEQ ID NOs: 2, 18, 34, 50, 66, 82, 98, 114, 130, 146, 162, 178, 194, 210, 287, 303, 319, 335, 351, and 367, and (ii) an apelin peptide which is a fragment or analogue of the preproapelin polypeptide having an amino acid sequence of SEQ ID NO: 227; and the second polynucleotide encodes a polypeptide comprising a light chain variable region (LCVR) having an amino acid sequence selected from the group consisting of SEQ ID NOs: 10, 26, 42, 58, 74, 90, 106, 122, 138, 154, 170, 186, 202, 218, 295, 311, 327, 343, 359, and 375.

In other embodiments, the first polynucleotide encodes a polypeptide comprising a heavy chain variable region (HCVR) having an amino acid sequence selected from the group consisting of SEQ ID NOs: 2, 18, 34, 50, 66, 82, 98, 114, 130, 146, 162, 178, 194, 210, 287, 303, 319, 335, 351, and 367, and the second polynucleotide encodes a polypeptide comprising (i) a light chain variable region (LCVR) having an amino acid sequence selected from the group consisting of SEQ ID NOs: 10, 26, 42, 58, 74, 90, 106, 122, 138, 154, 170, 186, 202, 218, 295, 311, 327, 343, 359, and 375, and (ii) an apelin peptide which is a fragment or analogue of the preproapelin polypeptide having an amino acid sequence of SEQ ID NO: 227.

The present invention includes anti-APLNR antibodies and antibody-fusion proteins having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al., 2002, JBC 277:26733). In other applications, modification of galactosylation can be made in order to modify complement dependent cytotoxicity (CDC).

In another aspect, the invention provides a pharmaceutical composition comprising a recombinant human antibody, antibody-fusion protein or fragment thereof which specifically binds APLNR and a pharmaceutically acceptable carrier. In a related aspect, the invention features a composition which is a combination of an anti-APLNR antibody or antibody-fusion protein and a second therapeutic agent. In one embodiment, the second therapeutic agent is any agent that is advantageously combined with an anti-APLNR antibody or antibody-fusion protein. Exemplary agents that may be advantageously combined with an anti-APLNR antibody include, without limitation, other agents that inhibit APLNR activity (including other antibodies or antigen-binding fragments thereof, fusion proteins, peptide agonists or antagonists, small molecules, etc.) and/or agents which do not directly bind APLNR but nonetheless interfere with, block or attenuate APLNR-mediated signaling. Exemplary agents that may be advantageously combined with an antibody-fusion protein include, without limitation, other agents that activate APLNR activity (including other fusion proteins, antibodies or antigen-binding fragments thereof, peptide agonists or antagonists, small molecules, etc.) and/or agents which activate APLNR signaling or downstream cellular effects. Additional combination therapies and co-formulations involving the antibodies and antibody-fusion proteins of the present invention are disclosed elsewhere herein. As such, a pharmaceutical composition is provided comprising any one or more of the antibodies, antibody-fusion proteins or antigen-binding fragments thereof, in accordance with the invention.

In yet another aspect, the invention provides therapeutic methods for inhibiting APLNR activity using an APLNR modulator of the invention, wherein the therapeutic methods comprise administering a therapeutically effective amount of a pharmaceutical composition comprising an antibody, antibody-fusion protein or antigen-binding fragment of an antibody of the invention. The disorder treated is any disease or condition which is improved, ameliorated, inhibited or prevented by removal, inhibition or reduction of APLNR activity or signaling. The anti-APLNR antibodies, antibody-fusion proteins or antibody fragments of the invention may function to block the interaction between APLNR and an APLNR binding partner (e.g., an APLNR receptor ligand such as an apelin peptide), or otherwise inhibit the signaling activity of APLNR.

In still another aspect, the invention provides therapeutic methods for activating APLNR activity using an APLNR modulator of the invention, wherein the therapeutic methods comprise administering a therapeutically effective amount of a pharmaceutical composition comprising an antibody, antibody-fusion protein or antigen-binding fragment thereof of the invention. The disorder treated is any disease or condition which is improved, ameliorated, inhibited or prevented by activation, stimulation, or amplification of APLNR activity or signaling. The anti-APLNR antibodies, antibody-fusion proteins or antibody fragments of the invention may function to enhance the interaction between APLNR and an APLNR binding partner (e.g., an APLNR receptor ligand such as an apelin peptide), or otherwise activate or augment the signaling activity of APLNR.

The present invention also includes the use of an anti-APLNR antibody, antibody-fusion protein or antigen-binding portion of an antibody of the invention in the manufacture of a medicament for the treatment of a disease or disorder related to or caused by APLNR activity in a patient. The invention further provides an antibody composition for use in the manufacture of a medicament for the treatment of a disease or disorder related to or caused by APLNR activity in a patient, such disease or disorder selected from the group consisting of cardiovascular disease, acute decompensated heart failure, congestive heart failure, myocardial infarction, cardiomyopathy, ischemia, ischemia/reperfusion injury, pulmonary hypertension, diabetes, neuronal injury, neurodegeneration, hot flash symptoms, fluid homeostasis, HIV infection, obesity, cancer, metastatic disease, retinopathy, fibrosis, and pathological angiogenesis.

The invention further provides a method for treating cardiovascular disease, acute decompensated heart failure, congestive heart failure, myocardial infarction, cardiomyopathy, ischemia, ischemia/reperfusion injury, pulmonary hypertension, diabetes, neuronal injury, neurodegeneration, hot flash symptoms, fluid homeostasis, HIV infection, obesity, cancer, metastatic disease, retinopathy, fibrosis, or pathological angiogenesis, the method comprising administering a pharmaceutical composition comprising any of the antibodies, antibody-fusion proteins or antigen-binding fragments thereof, according to the invention, to a subject in need thereof.

In one aspect, the invention provides an isolated antibody, antibody-fusion protein or antigen-binding fragment, wherein the antibody, antibody-fusion protein or antigen-binding fragment thereof comprises complementarity determining regions HCDR1-HCDR2-HCDR3-LCDR1-LCDR2-LCDR3 having the amino acid sequences of SEQ ID NOs: 382-383-384-377-385-386, respectively, and wherein the antibody, antibody-fusion protein or antigen-binding fragment thereof activates APLNR-mediated inhibition of cAMP accumulation with at least 39% of maximum apelin dose response activation. In some cases, the isolated antibody, antibody-fusion protein or antigen-binding fragment thereof activates APLNR-mediated inhibition of cAMP accumulation with at least 60% of maximum apelin dose response activation.

The isolated antibody, antibody-fusion protein or antigen-binding fragment thereof may comprise HCDR1-HCDR2-HCDR3-LCDR1-LCDR2-LCDR3 domains, respectively, selected from the group consisting of: SEQ ID NOs: 289-291-293-297-299-301; 305-307-309-313-315-317; 321-323-325-329-331-333; 337-339-341-345-347-349; 353-355-357-361-363-365; and 369-371-373-377-379-381. In some cases, the antibody, antibody-fusion protein or antigen-binding fragment comprises: (a) a heavy chain variable region (HCVR) having an amino acid sequence selected from the group consisting of SEQ ID NOs: 287, 303, 319, 335, 351, and 367; and (b) a light chain variable region (LCVR) having an amino acid sequence selected from the group consisting of SEQ ID NOs: 295, 311, 327, 343, 359, and 375. In some embodiments, the antibody, antibody-fusion protein or antigen-binding fragment comprises a HCVR/LCVR amino acid sequence pair selected from the group consisting of: SEQ ID NOs: 287/295, 303/311, 319/327, 335/343, 351/359, and 367/375.

In some embodiments in which the isolated antibody, antibody-fusion protein or antigen-binding fragment thereof activates APLNR-mediated inhibition of cAMP accumulation with at least 60% of maximum apelin dose response activation, the antibody, antibody-fusion protein or antigen-binding fragment comprises a HCVR/LCVR amino acid sequence pair selected from the group consisting of: SEQ ID NOs: 287/295, 319/327, 335/343, 351/359, and 367/375.

In one aspect, the invention provides an antibody, antibody-fusion protein or antigen-binding fragment that competes for binding to human apelin receptor (APLNR) with a reference antibody comprising an HCVR/LCVR sequence pair selected from the group consisting of SEQ ID NOs: 287/295, 303/311, 319/327, 335/343, 351/359, and 367/375.

In one aspect, the invention provides an antibody, antibody-fusion protein or antigen-binding fragment thereof that binds to the same epitope on APLNR as a reference antibody comprising an HCVR/LCVR sequence pair selected from the group consisting of SEQ ID NOs: 287/295, 303/311, 319/327, 335/343, 351/359, and 367/375.

In one aspect, the invention provides an isolated antibody, antibody-fusion protein or antigen-binding fragment thereof that comprises complementarity determining regions HCDR1-HCDR2-HCDR3-LCDR1-LCDR2-LCDR3 having the amino acid sequences of SEQ ID NOs: 382-383-384-377-385-386, respectively, wherein X=N in SEQ ID NO:386, and wherein the antibody, antibody-fusion protein or antigen-binding fragment thereof activates APLNR-mediated inhibition of cAMP accumulation with at least 60% of maximum apelin dose response activation.

In one aspect, the invention provides a pharmaceutical composition comprising the antibody, antibody-fusion protein or antigen-binding fragment thereof as discussed in the preceding paragraphs or herein, and a pharmaceutically acceptable carrier or diluent.

In one aspect, the invention provides a method for inducing vasodilation and/or angiogenesis in a subject, in which the method comprises administering the pharmaceutical composition discussed above to a subject in need thereof.

In one aspect, the invention provides a method for treating an ischemic-reperfusion injury, in which the method comprises administering the pharmaceutical composition discussed above to a subject in need thereof.

In one aspect, the invention provides a method for improving cardiac function, in which the method comprises administering the pharmaceutical composition discussed above to a subject in need thereof. In some cases, the subject suffers from a condition selected from congestive heart failure, myocardial infarction, or cardiomyopathy.

In one aspect, the invention provides an isolated antibody, antibody-fusion protein or antigen-binding fragment thereof that comprises complementarity determining regions HCDR1-HCDR2-HCDR3-LCDR1-LCDR2-LCDR3 having the amino acid sequences of SEQ ID NOs: 382-383-387-377-385-386, respectively, and wherein the antibody, antibody-fusion protein or antigen-binding fragment thereof activates APLNR-mediated inhibition of cAMP accumulation with at least 20% of maximum apelin dose response activation. In some cases, the isolated antibody, antibody-fusion protein or antigen-binding fragment thereof activates APLNR-mediated inhibition of cAMP accumulation with at least 21% of maximum apelin dose response activation.

The isolated antibody, antibody-fusion protein or antigen-binding fragment thereof may comprise HCDR1-HCDR2-HCDR3-LCDR1-LCDR2-LCDR3 domains, respectively, selected from the group consisting of: SEQ ID NOs: 36-38-40-44-46-48; 68-70-72-76-78-80; 84-86-88-92-94-96; 289-291-293-297-299-301; 305-307-309-313-315-317; 321-323-325-329-331-333; 337-339-341-345-347-349; 353-355-357-361-363-365; and 369-371-373-377-379-381. In some cases, the antibody, antibody-fusion protein or antigen-binding fragment comprises: (a) a heavy chain variable region (HCVR) having an amino acid sequence selected from the group consisting of SEQ ID NOs: 34, 66, 82, 287, 303, 319, 335, 351, and 367; and (b) a light chain variable region (LCVR) having an amino acid sequence selected from the group consisting of SEQ ID NOs: 42, 74, 90, 295, 311, 327, 343, 359, and 375. In some embodiments, the antibody, antibody-fusion protein or antigen-binding fragment comprises a HCVR/LCVR amino acid sequence pair selected from the group consisting of: SEQ ID NOs: 34/42, 66/74, 82/90, 287/295, 303/311, 319/327, 335/343, 351/359, and 367/375.

In one aspect, the invention provides an isolated antibody, antibody-fusion protein or antigen-binding fragment thereof that comprises one or more of the consensus CDR sequences set forth in SEQ ID NOs: 382, 383, 384, 385, 386 and 387.

Other embodiments will become apparent from a review of the ensuing detailed description.

DETAILED DESCRIPTION

Figure 1:
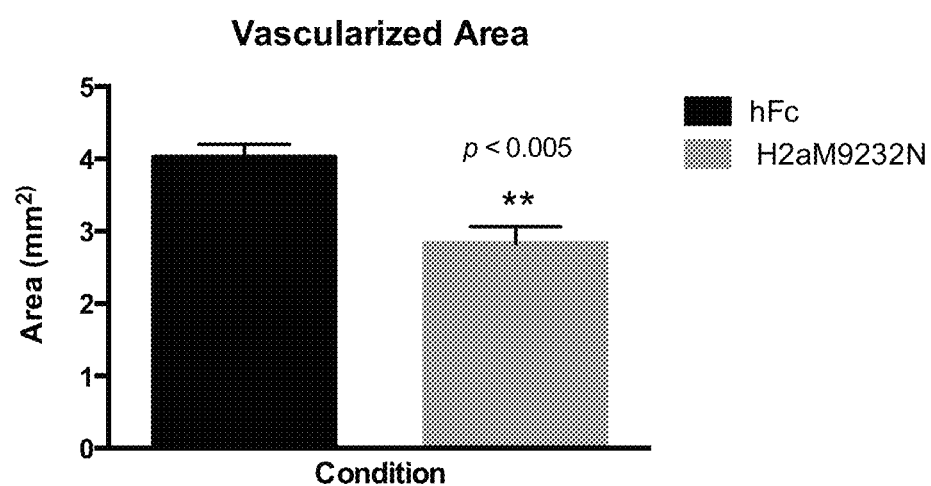
FIG. 1 depicts the statistical analysis of the effects of anti-APLNR antibody in an RVD model. An antagonistic anti-APLNR antibody, H2aM9232N, produced a statistically significant mean reduction of approximately 30% in retinal blood vessel outgrowth compared to control (hFc) in the developing mouse retina, indicating that APLNR blockade has a significant anti-angiogenic effect (**p<0.005; two-tailed p value=0.0014; t=4.123, df=12).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expressions "apelin receptor," "APLNR," "APJ receptor," and the like, as used herein, refer to a human APLNR protein having the amino acid sequence of SEQ ID NO: 225, or a substantially similar amino acid sequence to SEQ ID NO: 225. All references to proteins, polypeptides and protein fragments herein are intended to refer to the human version of the respective protein, polypeptide or protein fragment unless explicitly specified as being from a non-human species (e.g., "mouse APLNR," "monkey APLNR," etc.).

As used herein, "an antibody or antibody-fusion protein that binds APLNR" or an "anti-APLNR antibody" includes immunoglobulin molecules, antibodies, antibody-fusion proteins and antigen-binding fragments thereof that bind a soluble fragment of an APLNR protein. Soluble APLNR molecules include natural APLNR proteins as well as recombinant APLNR protein variants such as, e.g., monomeric and dimeric APLNR constructs.

The term "immunoglobulin" (Ig) refers to a class of structurally related glycoproteins consisting of two pairs of polypeptide chains, one pair of light (L) chains and one pair of heavy (H) chains, which may all four be inter-connected by disulfide bonds. The structure of immunoglobulins has been well characterized. See for instance Fundamental Immunology Ch. 7 (Paul, W., ed., 2nd ed. Raven Press, N. Y. (1989)). The proteins of the invention comprise amino acid sequences that may be derived from an immunoglobulin molecule, such as derived from any immunoglobulin region or domain.

The term "antibody", as used herein, means any antigen-binding molecule or molecular complex comprising at least one complementarity determining region (CDR) that specifically binds to or interacts with a particular antigen (e.g., APLNR). The term "antibody" includes immunoglobulin molecules comprising four polypeptide chains, two heavy (H) chains and two light (L) chains inter-connected by disulfide bonds, as well as multimers thereof (e.g., IgM), as well as immunoglobulin molecules including a fragment of one or more heavy chains or a fragment of one or more light chains, (e.g. Fab, F(ab')$_2$ or scFv fragments), as described herein. Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-APLNR antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc. Such techniques may also be employed to synthesize any antibody-fusion molecule containing an antigen-binding fragment derived from a full antibody molecule.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$—$V_L$ or $V_L$—$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; $V_H$-$C_H2$-$C_H3$; $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The phrase "antibody-fusion proteins" includes recombinant polypeptides and proteins derived from antibodies of the invention that have been engineered to contain an antibody or antigen-binding fragment as described herein. For example, an "antibody-apelin fusion protein" includes a chimeric protein comprising an amino acid sequence derived from an anti-APLNR antibody fused to an amino acid sequence of an apelin peptide or analogue. The apelin peptide component may be fused to the anti-APLNR antibody or antigen-binding fragment either at the N-terminus or the C-terminus of the antibody light chain or heavy chain, with or without peptide linkers. The phrase "fused to", as used herein, means (but is not limited to) a polypeptide formed by expression of a chimeric gene made by combining more than one sequence, typically by cloning one gene into an expression vector in frame with a second gene such that the two genes are encoding one continuous polypeptide. Recombinant cloning techniques, such as polymerase chain reaction (PCR) and restriction endonuclease cloning, are well-known in the art. In addition to being made by recombinant technology, parts of a polypeptide can be "fused to" each other by means of chemical reaction, or other means known in the art for making custom polypeptides.

In some embodiments, the components or amino acids of an antibody-fusion protein are separated by a linker (or "spacer") peptide. Such peptide linkers are well known in the art (e.g., polyglycine or Gly-Ser linkers) and typically allow for proper folding of one or both of the components of the antibody-fusion protein. The linker provides a flexible junction region of the component of the fusion protein, allowing the two ends of the molecule to move independently, and may play an important role in retaining each of the two moieties' appropriate functions. Therefore, the junction region acts in some cases as both a linker, which combines the two parts together, and as a spacer, which allows each of the two parts to form its own biological structure and not interfere with the other part. Furthermore, the junction region should create an epitope that will not be recognized by the subject's immune system as foreign, in other words, will not be considered immunogenic. Linker selection may also have an effect on binding activity, and thus the bioactivity, of the fusion protein. (See Huston, et al, 1988, *PNAS*, 85:16:5879-83; Robinson & Bates, 1998, *PNAS* 95(11):5929-34; and Arai, et al. 2001, *PEDS*, 14(8): 529-32; Chen, X. et al., 2013, *Advanced Drug Delivery Reviews* 65:1357-1369.) In one embodiment, the apelin peptide is connected to the C-terminus or to the N-terminus of the light chain or heavy chain of the antibody or antigen-binding fragment thereof, via one or more peptide linkers.

The antibodies and antibody-fusion proteins of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al., 1998, *Proc. Natl. Acad. Sci.* (*USA*) 95:652-656). The constant region of an antibody or antibody-fusion protein is important in the ability of an antibody to fix complement and mediate cell-dependent cytotoxicity. Thus, the isotype of an antibody may be selected on the basis of whether it is desirable for the antibody to mediate cytotoxicity.

In another aspect, the antibody or antibody-fusion protein may be engineered at its Fc domain to activate all, some, or none of the normal Fc effector functions, without affecting the antibody's desired pharmacokinetic properties. Therefore, antibodies or antibody-fusion proteins with engineered Fc domains that have altered Fc receptor binding may have reduced side effects. Thus, in one embodiment, the protein comprises a chimeric or otherwise modified Fc domain. For an example of a chimeric Fc domain, see PCT International Publication No. WO/2014/121087 A1, published Aug. 7, 2014, which is herein incorporated by reference in its entirety.

In certain embodiments of the invention, the anti-APLNR antibodies and antibody-fusion proteins of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies and antibody-fusion proteins of the invention may, in some embodiments, be recombinant human antibodies. The term "recombinant human antibody", as used herein, is intended to include all human antibodies and fusion proteins thereof that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al., 1992, *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angel et al., 1993, *Molecular Immunology* 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies and antibody-fusion proteins of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention includes neutralizing and/or blocking anti-APLNR antibodies and antibody-fusion proteins. A "neutralizing" or "blocking" antibody, as used herein, is intended to refer to an antibody whose binding to APLNR: (i) interferes with the interaction between APLNR or an APLNR fragment and an APLNR receptor component (e.g., apelin peptide, etc.); and/or (ii) results in inhibition of at least one biological function of APLNR. The inhibition caused by an APLNR neutralizing or blocking antibody need not be complete so long as it is detectable using an appropriate assay.

The term "antagonist", as used herein, refers to a moiety that binds to the receptor at the same site or near the same site as an agonist (for example, the endogenous ligand), but which does not activate the intracellular response typically initiated by the active form of the receptor, and thereby inhibits or neutralizes the intracellular response by an agonist or partial agonist. In some cases, antagonists do not diminish the baseline intracellular response in the absence of an agonist or partial agonist. An antagonist does not necessarily have to function as a competitive binding inhibitor, but may work by sequestering an agonist, or indirectly modulating a downstream effect.

The present invention includes anti-APLNR antibodies and antibody-fusion proteins that activate APLNR, however to a lesser extent than the activation exhibited by a full agonist of the APLNR, such as an apelin peptide. For example, such an "activating" antibody, as used herein, is intended to refer to an antibody whose binding to APLNR: (i) augments the interaction between APLNR or an APLNR fragment and an APLNR ligand (e.g., apelin peptide, etc.); and/or (ii) results in activation of at least one biological function of APLNR. The activation caused by an anti-APLNR antibody need not be complete so long as it is detectable using an appropriate assay. To this end, an activating antibody may function as a partial or inverse agonist of the APLNR.

The term "agonist", as used herein, refers to a moiety that interacts with (directly or indirectly binds) and activates the receptor and initiates a physiological or pharmacological response characteristic of that receptor, such as when bound to its endogenous ligand. For example, upon binding to APLNR, apelin activates the receptor which internalizes the receptor. Also, APLNR-apelin binding activates APLNR which decreases adenylyl cyclase activity and therefore inhibits cAMP accumulation in the cell.

The term "$EC_{50}$" or "EC50", as used herein, refers to the half maximal effective concentration, which includes the concentration of a ligand that induces a response, for example a cellular response, halfway between the baseline and maximum after a specified exposure time. The $EC_{50}$ essentially represents the concentration of a ligand where 50% of its maximal effect is observed. Thus, with regard to cellular signaling, increased receptor activity is observed with a decreased $EC_{50}$ value, i.e. half maximal effective concentration value (less ligand needed to produce a greater response).

The term "$IC_{50}$" or "IC50", as used herein, refers to the half maximal inhibitory concentration of a cellular response. In other words, the measure of the effectiveness of a particular moiety (e.g. protein, compound, or molecule) in inhibiting biological or biochemical receptor function, wherein an assay quantitates the amount of such moiety needed to inhibit a given biological process. Thus, with regard to cellular signaling, a greater inhibitory activity is observed with a decreased $IC_{50}$ value.

Exemplary assays for detecting APLNR activation and inhibition are described in the working Examples herein.

The anti-APLNR antibodies and antibody-fusion proteins disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies and antibody-fusion proteins of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies, and antibody-fusion proteins and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies, and antibody-fusion proteins and antigen-binding fragments obtained in this general manner are encompassed within the present invention.

The present invention also includes anti-APLNR antibodies and antibody-fusion proteins comprising variants of any of the HCVR, LCVR, and/or CDR amino acid sequences disclosed herein having one or more conservative substitutions. For example, the present invention includes anti-APLNR antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, 1994, *Methods Mol. Biol.* 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al., 1992, *Science* 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson, 1994, supra). Another preferred algorithm when comparing a sequence of the invention to a database containing a large number of sequences from different organisms is the computer program BLAST, especially BLASTP or TBLASTN, using default parameters. See, e.g., Altschul et al., 1990, *J. Mol. Biol.* 215:403-410 and Altschul et al., 1997, *Nucleic Acids Res.* 25:3389-402, each herein incorporated by reference.

Biological Characteristics of the APLNR Modulators

The present invention includes anti-APLNR antibodies and antigen-binding fragments thereof that bind human APLNR and inhibit or attenuate APLNR-mediated signaling. An anti-APLNR antibody is deemed to "inhibit or attenuate APLNR-mediated signaling" if, e.g., the antibody exhibits one or more properties selected from the group consisting of: (1) inhibition of APLNR-mediated signaling in a cell-based bioassay, such as increased accumulation of cAMP; (2) inhibition of APLNR-induced phosphorylation of ERKs; and (3) inhibition of APLNR-mediated β-arrestin interaction, including blocking internalization.

The present invention includes antibody-fusion proteins that bind human APLNR and activate APLNR-mediated signaling. An antibody-fusion protein is deemed to "activate APLNR-mediated signaling" if, e.g., the antibody exhibits one or more properties selected from the group consisting of: (1) activation or detection of APLNR-mediated signaling in a cell-based bioassay, such as inhibition of cAMP; (2) activation of APLNR-induced phosphorylation of ERKs; and (3) activation of APLNR-mediated β-arrestin interaction, including internalization.

Inhibition or activation of APLNR-mediated signaling in a cell-based bioassay means that an anti-APLNR antibody, antibody fusion protein or antigen-binding fragment thereof modifies the signal produced in cells that express an APLNR receptor and a reporter element that produces a detectable signal in response to APLNR binding, e.g., using the assay formats described herein, or a substantially similar assay meant to measure the APLNR cellular signaling. APLNR is a G protein-coupled receptor, specifically a Gi/o-coupled receptor, whereas stimulation of the receptor results in inhibition of adenylate cyclase activity which in turn effects the accumulation of cyclic AMP (cAMP) or other cell signaling events.

For example, the present invention includes APLNR modulators thereof that block or inhibit apelin-mediated signaling in cells expressing human APLNR, with an $IC_{50}$ of less than about 20 nM, less than about 10 nM, less than about 2 nM, less than about 1 nM, less than about 900 pM, less than about 800 pM, less than about 700 pM, less than about 600 pM, less than about 500 pM, less than about 400 pM, less than about 350 pM, less than about 300 pM, less than about 250 pM, less than about 200 pM, less than about 150 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM, as measured in a cell-based blocking or inhibition bioassay, e.g., using the assay format as defined in Examples 5, 8, 9 or 11 herein, or a substantially similar assay.

Inhibition of APLNR-induced phosphorylated ERK1/2 (pERK assay) in transfected cells means that an APLNR modulator inhibits or reduces the ratio of pERK1/2 to total ERK in cells expressing human APLNR in the presence of human apelin, e.g., as measured using the assay system of Examples 6 or 10, or a substantially similar assay. For example, the present invention includes APLNR modulators that inhibit APLNR-mediated ratio of pERK, in the presence of apelin, with an $IC_{50}$ of less than about 50 nM, less than about 25 nM, less than about 20 nM, less than about 15 nM, less than about 10 nM, less than about 5 nM, less than about 1 nM, less than about 900 pM, less than about 800 pM, less than about 700 pM, less than about 600 pM, less than about 500 pM, less than about 400 pM or less than about 300 pM, as measured in an APLNR-induced pERK assay, e.g., using the assay format as defined in Example 6 or 10 herein, or a substantially similar assay.

In other embodiments, however, certain APLNR modulators of the present invention, despite having the ability to inhibit or attenuate APLNR-mediated signaling, do not block or only partially block the interaction of APLNR and apelin. Such antibodies, antibody-fusion proteins and antigen-binding fragments thereof, may be referred to herein as "indirect blockers." Without being bound by theory, it is believed that the indirect blockers of the invention function by binding to APLNR at an epitope that does overlap, or overlaps only partially, with the N-terminal ligand binding domain of APLNR, but nonetheless interferes with APLNR-mediated signaling without blocking the APLNR/apelin interaction directly.

In another embodiment of the invention, the APLNR modulator is a partial agonist or an inverse agonist. Full agonists activate the receptor to a maximal extent. Compounds having a lower effect than a full agonist are called partial agonists, since they stimulate signal transduction but to a lesser extent than a full agonist. Inverse agonists reduce the basal level of the measurable or detectable signal upon binding to the receptor, indicative of interference with or blocking endogenous activity. In other words, some inverse agonists reduce the activity of certain receptors by inhibiting their constitutive activity.

In certain embodiments, the present invention includes APLNR modulators thereof that activate or increase signaling in cells expressing human APLNR, with an EC50 of less than about 100 nM, less than about 75 nM, less than about 50 nM, less than about 25 nM, less than about 10 nM, less than about 1 nM, less than about 900 pM, less than about 800 pM, less than about 700 pM, less than about 600 pM, less than about 500 pM, less than about 400 pM, less than about 350 pM, less than about 300 pM, less than about 250 pM, less than about 200 pM, less than about 150 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM, as measured in a cell-based APLNR activation bioassay, e.g., using the assay format as defined in Examples 5, 8, 9 or 11 herein, or a substantially similar assay.

Activation of APLNR-mediated phosphorylated ERK1/2 (pERK) in transfected cells means that an APLNR modulator increases the ratio of pERK1/2 to total ERK in cells expressing human APLNR, e.g., as measured using the assay system of Examples 6 or 10, or a substantially similar assay. For example, the present invention includes APLNR modulators that increase APLNR-mediated ratio of pERK, in the presence of apelin, with an EC50 of less than about 100 nM, less than about 75 nM, less than about 50 nM, less than about 25 nM, less than about 20 nM, less than about 15 nM, less than about 10 nM, less than about 5 nM, less than about 1 nM, less than about 900 pM, less than about 800 pM, less than about 700 pM, less than about 600 pM, less than about 500 pM, less than about 400 pM or less than about 300 pM, as measured in an APLNR-induced pERK assay, e.g., using the assay format as defined in Examples 6 or 10 herein, or a substantially similar assay.

The present invention includes APLNR modulators that bind soluble APLNR molecules with high affinity and/or specificity. For example, the present invention includes antibodies and antigen-binding fragments of antibodies that bind APLNR with a binding ratio of greater than about 20 as measured by a fluorescent activated cell sorting (FACS) assay, e.g., using the assay format as defined in Example 4 herein. In certain embodiments, the antibodies or antigen-binding fragments of the present invention bind APLNR with a binding ratio of greater than about 15, greater than about 20, greater than about 100, greater than about 200, greater than about 300, greater than about 400, greater than about 500, greater than about 1000, greater than about 1500, or greater than about 2000, as measured by e.g., FACS, or a substantially similar assay.

The present invention also includes anti-APLNR antibodies and antigen-binding fragments thereof that specifically bind to APLNR with a dissociative half-life (t %) of greater than about 10 minutes as measured by surface plasmon resonance at 25° C. or 37° C., e.g., using the well-known BIAcore™ assay format, or a substantially similar assay.

The antibodies of the present invention may possess one or more of the aforementioned biological characteristics, or any combinations thereof. Other biological characteristics of the antibodies of the present invention will be evident to a person of ordinary skill in the art from a review of the present disclosure including the working Examples herein.

Receptor Assays

The cell signaling pathway of a Gi/o-coupled receptor, such as APLNR, may be measured by a variety of bioassays. Phosphorylation of ERK 1/2 provides a direct physiological functional readout of activation of Gi/o-coupled GPCRs. A common method of testing for activation of a Gi/o-coupled GPCR is inhibition of adenylate cyclase activity which requires measuring the reduction of forskolin-stimulation of cAMP levels that accumulate in the cell.

Activation of Gi/o-coupled receptors results in decreased adenylyl cyclase activity and therefore inhibition of cAMP in the cell, via the G alpha subunits Gi or Go. To maximize the inhibition signal, forskolin (a direct activator of adenylate cyclase) is typically utilized to stimulate adenylyl cyclase in the assay, and thus cAMP, thereby rendering the inhibition signal more easily detectable. Radiometric GE Healthcare SPA™ (Piscataway, N.J., USA) and Perkin Elmer Flash-Plate™ cAMP assays are available, as well as fluorescence or luminescence-based homogenous assays (e.g. PerkinElmer AlphaScreen™, DiscoveRx HitHunter™ (Fremont, Calif., USA), and Molecular Devices FLIPR® (Sunnyvale, Calif., USA)) to measure accumulation of intracellular cAMP.

The [$^{35}$S]GTPγS assay is generally useful for Gi/o-coupled receptors because Gi/o is the most abundant G protein in most cells and has a faster GDP-GTP exchange rate than other G proteins (Milligan G., 2003, Trends Pharmacol Sci, 2003, 24:87-90). APLNR-mediated guanine nucleotide exchange is monitored by measuring [$^{35}$S]GTPγS binding to plasma membranes prepared from cells expressing APLNR. Commercially available Scintillation Proximity Assay (SPA™) kits allow measurement of desired [$^{35}$S] GTPγS-bound a subunit (PerkinElmer, Waltham, Mass., USA).

The action of GPCRs that modulate cAMP levels, like APLNR, may be linked to luciferase transcription in a cell by a cAMP response element (CRE). A CRE-luc construct (CRE-responsive luciferase) encodes a luciferase reporter gene under the control of a promoter and tandem repeats of the CRE transcriptional response element (TRE). Following activation of the receptor, cAMP accumulation in the cell is measured by the amount of luciferase expressed in the cell following addition of chemiluminescent detection reagents. For APLNR, and other Gi-coupled receptors, forskolin is added to induce cAMP and a decrease in CRE activity (chemiluminescence) indicates GPCR activation. Various commercial kits are available, such as from Promega (Madison, Wis., USA), SABiosciences (A Qiagen Company, Valencia, Calif., USA), etc.

Phosphorylated ERK (pERK) may be measured in cell lysates from cells expressing APLNR receptors to determine APLNR activation. Endogenous extracellular signal-regulated kinase 1 and 2 (ERK1 and ERK2), belong to a conserved family of serine/threonine protein kinases and are involved cellular signaling events associated with a range of stimuli. The kinase activity of ERK proteins is regulated by dual phosphorylation at Threonine 202/Tyrosine 204 in ERK1, and Threonine 185/Tyrosine 187 in ERK2. MEK1 and MEK2 are the primary upstream kinases responsible for ERK 1/2 in this pathway. Many downstream targets of ERK 1/2 have been identified, including other kinases, and transcription factors. In one example, the pERK 1/2 assay utilizes an enzyme-linked immunosorbent assay (ELISA) method to measure specific phosphorylation of ERK 1 in cellular lysates of cell cultures expressing recombinant or endogenous receptors. In another example, the pERK 1/2 assay uses a primary (non-conjugated) antibody which recognizes phosphorylated Thr202/Tyr204 in ERK1 or phos-Thr185/Tyr187 in ERK2 and a secondary conjugated antibody that recognizes the primary antibody, whereas the secondary conjugated mAb provides a method of detection such as a conjugate reacts with an exogenously added substrate. Various commercial kits are available, such as AlphaScreen® SureFire™ (PerkinElmer), ThermoScientific (Waltham, Mass., USA), Sigma Aldrich (St. Louis, Mo., USA) etc.).

In some instances, agonist binding to the receptor may initiate arrestin-mediated signaling, without triggering G protein-mediated signaling or slow down G protein-mediated signaling. Beta-arrestin (β-arrestin) interaction with GPCRs at the cell-surface can uncouple heterotrimeric G proteins to the receptor and lead to other cell signaling cascades. β-arrestin is known to trigger endocytosis and activation of the ERK pathway. In one example assay, bioluminescence resonance energy transfer or BRET has been used to study the interaction of GPCRs fused to Renilla luciferase (Rlu) with β-arrestin fused to green fluorescent protein (GFP). In this example, BRET is based on the transfer of energy between recombinant expressed GPCR-Rlu and β-arrestin-GFP when they are in close proximity after the addition of the luciferase substrate coelentcrazine, thus allowing measurement of real-time evaluation of these protein—protein interactions in whole cells.

Other assays have been developed, such as PathHunter® GPCR assays (DiscoveRx Corp., Fremont, Calif., USA) that directly measure GPCR activity by detecting β-arrestin interaction with the activated GPCR. Briefly, the GPCR is fused in frame with the small enzyme fragment ProLink™ and co-expressed in cells stably expressing a fusion protein of β-arrestin and a deletion mutant of β-galactosidase (i.e. β-gal, an enzyme acceptor, or EA). Activation of the GPCR stimulates binding of β-arrestin to the ProLink-tagged GPCR and the complementation of the two enzyme fragments results in formation of an active β-gal enzyme. An increase in enzyme activity (i.e. GPCR activation) can be measured using chemiluminescent detection reagents.

β-arrestin molecules have been shown to regulate GPCR internalization (i.e. endocytosis) following activation of GPCRs, such as APLNR. Agonist-activation of GPCRs leads to conformational changes, phosphorylation of the receptor, and activation of β-arrestin, or other pathways, to mediate receptor sequestration from the cell surface. The sequestration mechanism may be a means of desensitization (i.e. receptor is degraded following internalization) or resensitization (i.e. receptor is recycled back to the cell surface). See, e.g., Claing, A., et al. 2002, Progress in Neurobiology 66: 61-79, for review.

APLNR antagonists may block internalization of the receptor. APLNR agonists may induce internalization and/or resensitization of the APLNR (Lee, D K, et al. 2010, *BBRC*, 395:185-189). In some embodiments, the APLNR agonist exhibits or induces increased APLNR resensitization, as measured by an internalization assay. In other embodiments, the APLNR agonist exhibits or induces increased cell-surface receptor copy of the APLNR, as measured in an internalization assay. Measuring the extent (such as an increase) of receptor internalization in any internalization assay is done by determining the difference between the noninternalized measurement (i.e., cells without prior exposure to agonist) and the measurement obtained with agonist in the assay.

Apelin receptor sequestration, and thus apelin receptor copy, may be measured by a number of methods well-known in the art. APLNR agonist stimulation may result in increased or decreased receptor copy on the surface of a particular cell. For example, an apelin receptor agonist induces APLNR internalization may have an effect of blood pressure. Receptor internalization assays are routinely done employing, for example, fluorescently-labeled or radiolabeled ligands, or immunofluorescent labels (fluorescentlytagged anti-receptor antibodies), followed by microscopy and digital imaging techniques (see, e.g., El Messari et al. 2004, *J Neurochem,* 90:1290-1301; Evans, N., 2004, Methods of Measuring Internalization of G Protein—Coupled Receptors. *Current Protocols in Pharmacology.* 24: 12.6.1-12.6.22).

Apelin Peptides

Apelin is produced as a prepropeptide of 77 amino acids which is cleaved to yield several shorter biologically active fragments, or apelin peptides. As described herein, anti-APLNR antibodies may block or interfere with the binding of apelin peptides to the APLNR. Antibody-fusion proteins comprising an apelin peptide may activate APLNR or augment APLNR activity. Any apelin peptides may be derived from the preproapelin polypeptide (SEQ ID NO: 227) and fused to the anti-APLNR antibodies of the invention. Apelin peptides includes fragments of apelin peptides having C-terminal deletions, some of which have been found to retain their cellular activities (Messari et al. 2004, *J Neurochem,* 90:1290-1301). Apelin peptides also include substituted and/or modified amino acids as described herein which confer altered activity compared to the endogenous activity of apelin. As such, apelin analogues may include substituted or modified amino acid(s) that remove potential cleavage sites or otherwise stabilize the protein. As such, deletion or addition of one or more C-terminal amino acids to the apelin peptide of an apelin-Fc-fusion protein may confer increased stability, such as resistance to degradation. Such modification of apelin peptides does not alter their ability to activate the APLNR. Exemplary modified apelin peptides are included in Tables 9 and 10A-D, e.g. SEQ ID NO: 261, SEQ ID NO: 262, SEQ ID NO: 270, SEQ ID NO: 271, SEQ ID NO: 272, and SEQ ID NO: 273. Exemplary apelin fusion proteins of the invention that comprise such modified apelin peptides are included in this invention.

In some embodiments, the apelin peptide comprises a fragment or analogue of the preproapelin polypeptide (SEQ ID NO: 227). An "apelin peptide" as used herein includes non-limiting exemplary apelin fragments and analogues known in the art, e.g., an apelin peptide comprising amino acids 6-77, 40-77, 42-77, 43-77, 47-77, 59-77, 61-77, 63-77, 64-77, 65-77, 66-77, 67-77, 73-77, 1-25, 6-25, 42-64, 61-64, 61-74, 61-75, 61-76, 65-76, 65-75, 66-76, 67-76, 66-75, 67-75, 42-58, 42-57, 42-56, 42-55, 42-54, 42-53, or pyro-glutamylated apelin65-77 ([Pyr$^1$]Apelin-13), of the preproapelin polypeptide (SEQ ID NO: 227). See e.g. U.S. Pat. No. 6,492,324, issued on Dec. 10, 2002, and Messari et al. 2004, supra, both of which are herein incorporated by reference.

In some embodiments, the apelin peptide is selected from the group consisting of apelin40-77 (apelin-38), apelin42-77 (apelin-36), apelin43-77 (apelin-35), apelin47-77 (apelin-31), apelin59-77 (apelin-19), apelin6l-77 (apelin-17), apelin63-77 (apelin-15), apelin64-77 (apelin-14), apelin65-77 (apelin-13), apelin66-77 (apelin-12, or Al2), apelin67-77 (apelin-11), apelin68-77 (apelin-10), apelin73-77 (apelin-5), apelin61-76 (apelin-K16P), apelin61-75 (apelin-K15M), apelin61-74 (apelin-K14P), and [Pyr$^1$]Apelin-13. Certain apelin peptides are cleavage products of the preproapelin polypeptide (SEQ ID NO: 227) yielding various lengths of the C-terminus of preproapelin. As such, the apelin peptide consisting of amino acids 42-77 of SEQ ID NO: 227 is referred to as apelin-36; the apelin peptide consisting of amino acids 61-77 of SEQ ID NO: 227 is referred to as apelin-17; the apelin peptide consisting of amino acids 65-77 of SEQ ID NO: 227 is referred to as apelin-13; the apelin peptide consisting of amino acids 67-77 of SEQ ID NO: 227 is referred to as apelin-11; and so on.

In some embodiments, the apelin peptide, or analogue thereof, is selected from the group consisting of apelin-36 (SEQ ID NO: 230), apelin-17 (SEQ ID NO: 229), apelin-13 (SEQ ID NO: 228) and [Pyr1]Apelin-13. In another embodiment, the apelin peptide comprises apelin-13 (SEQ ID NO: 228), or a fragment or analogue thereof.

Further modification of apelin peptides at the C-terminus of preproapelin polypeptide may eliminate or interfere with enzymatic cleavage of the peptide, for example ACE2 cleavage. In some embodiments, the apelin peptide is modified to minimize degradation and to enhance serum stability. In certain embodiments, the modified apelin peptide is selected from the group consisting of SEQ ID NO: 270 (apelin-Cter9), SEQ ID NO: 271 (apelin-Cter10), SEQ ID NO: 262 (apelin-Cter11), SEQ ID NO: 272 (apelin-Cter11+S), SEQ ID NO: 273 (apelin-V5-11), SEQ ID NO: 269 (apelin-13+5G), SEQ ID NO: 283 (apelin-13+R), SEQ ID NO: 284 (apelin-13+S), and SEQ ID NO: 285 (apelin-13+H). The Apelin-antibody fusions of the invention may be tethered to any of these modified peptides, particularly at the N-terminus of the antibody heavy or light chain(s).

Apelin peptides are rapidly cleared from the circulation and have a short plasma half-life of no more than eight minutes (Japp, et al, 2008, *J of Amer College Cardiolog,* 52(11):908-13). Apelin fusion proteins of the invention have increased half-life compared to apelin peptides.

In other embodiments, the apelin peptide, or fragment or analogue thereof, is fused to the 5' (N-terminal) end or the 3' (C-terminal) end of one or both heavy chains of the antibody. In still other embodiments, the apelin peptide, or analogue thereof, is fused to the 5' (N-terminal) end or the 3' (C-terminal) end of one or both light chains of the antibody.

In still other embodiments, the apelin peptide, or fragment or analogue thereof, is fused to the 5' (N-terminal) end or the 3' (C-terminal) end of an immunoglobulin molecule, including an antigen-binding fragment such as an APLNR-binding fragment, selected from the group consisting of a Fab fragment, a F(ab')2 fragment, an Fd fragment, an Fv fragment, an single-chain Fv (scFv) fragment, a dAb fragment, and an isolated complementarity determining region (CDR).

Included in the invention are analogues of apelin modified to include non-standard amino acids or modified amino acids. Such peptides containing non-natural, or natural but non-coded, amino acids may be synthesized by an artificially modified genetic code in which one or mode codons is assigned to encode an amino acid which is not one of the standard amino acids. For example, the genetic code encodes 20 standard amino acids, however, three additional proteinogenic amino acids occur in nature under particular circumstances: selenocysteine, pyrrolysine and N-Formyl-methionine (Ambrogelly, et al. 2007, *Nature Chemical Biology,* 3:29-35; Bock, A. et al, 1991, *TIBS,* 16 (12): 463-467; and Théobald-Dietrich, A., et al., 2005, *Biochimie,* 87(9-10):813-817). Post-translationally modified amino acids, such as carboxyglutamic acid (γ-carboxyglutamate), hydroxyproline, and hypusine, are also included. Other non-standard amino acids include, but are not limited to, citrulline, 4-benzoylphenylalanine, aminobenzoic acid, aminohexanoic acid, Nα-methylarginine, α-Amino-n-butyric acid, norvaline, norleucine, alloisoleucine, t-leucine, α-Amino-n-heptanoic acid, pipecolic acid, α,β-diaminopropionic acid, α,γ-diaminobutyric acid, ornithine, allothreonine, homoalanine, homoarginine, homoasparagine, homoaspartic acid, homocysteine, homoglutamic acid, homoglutamine, homoisoleucine, homoleucine, homomethionine, homophenylalanine, homoserine, homotyrosine, homovaline, isonipecotic acid, β-Alanine, β-Amino-n-butyric acid, β-Aminoisobutyric acid, γ-Aminobutyric acid, α-aminoisobutyric acid, isovaline, sarcosine, naphthylalanine, nipecotic acid, N-ethyl glycine, N-propyl glycine, N-isopropyl glycine, N-methyl alanine, N-ethyl alanine, N-methyl β-alanine, N-ethyl β-alanine, octahydroindole-2-carboxylic acid, penicillamine, pyroglutamic acid, sarcosine, t-butylglycine, tetrahydro-isoquinoline-3-carboxylic acid, isoserine, and α-hydroxy-γ-aminobutyric acid. A variety of formats to expand the genetic code are known in the art and may be employed in the practice of the invention. (See e.g. Wolfson, W., 2006, Chem Biol, 13(10): 1011-12.)

Apelin analogues incorporating such non-standard amino acids or post-translational modifications can be synthesized by known methods. Exemplary apelin analogues include Nα-methylarginine-apelin-A12 analogue, [Nle75, Tyr]apelin-36, [G1p65N1e75,Tyr77]apelin-13, (Pyr1)[Met(O)11]-apelin-13, (Pyr1)-apelin-13, [d-Ala12]-A12, and N-alpha-acetyl-nona-D-arginine amide acetate.

Also included in the invention are analogues of the apelin component of an antibody-fusion protein modified to be resistant to cleavage, for example cleavage by angiotensin converting enzyme 2 (ACE2). Such apelin analogues have been shown to have a marked increase in efficacy compared to unmodified apelin ligands in in vivo models of myocardial response to ischemia (Wang, et al. Jul. 1, 2013, *J Am Heart Assoc.* 2: e000249).

Such cleavage-protected antibody-fusion proteins comprise apelin peptides that are modified to include substitution variants, i.e. variants made by the exchange of one amino acid for another at one or more cleavage sites within the protein. Such amino acid substitutions are envisioned to confer increased stability without the loss of other functions or properties of the protein. Other cleavage-protected antibody-fusion proteins comprise apelin peptides modified to include terminal amide or acetyl groups. In some embodiments, cleavage-protected antibody-fusion proteins comprise proteinogenic amino acids, non-standard amino acids or post-translationally modified amino acids. Some modified apelin peptides are modified to delete and/or add one or more C-terminal amino acids without altering their ability to activate the APLNR. Exemplary apelin fusion proteins of the invention include SEQ ID NO: 270 (apelin-Cter9), SEQ ID NO: 271 (apelin-Cter10), SEQ ID NO: 262 (apelin-Cter11), SEQ ID NO: 272 (apelin-Cter11+S), SEQ ID NO: 269 (apelin-13+5G), SEQ ID NO: 283 (apelin-13+R), SEQ ID NO: 284 (apelin-13+S), and SEQ ID NO: 285 (apelin-13+H). See also, PCT International Publication No. WO2014/152955 A1, published on Sep. 25, 2014, which is hereby incorporated by reference.

Antibody-Fusion Proteins

The present invention also provides an antibody-fusion protein or fragment thereof comprising an anti-APLNR antibody fused to an apelin peptide sequence. Any apelin peptides or analogues described herein and known in the art may be derived from the preproapelin polypeptide (SEQ ID NO: 227). Apelin peptides may be modified using ordinary molecular biological techniques and synthetic chemistry so as to improve their resistance to proteolytic cleavage or resistance to metal ion-related cleavage. Analogues of such polypeptides include substitution variants made by the exchange of one amino acid for another or substitution with residues other than naturally occurring L-amino acids, e.g. D-amino acids or non-naturally occurring synthetic amino acids.

Certain non-limiting, exemplary antibody-fusion proteins of the invention comprise heavy and light chain variable region (HCVR/LCVR) sequences selected from the group consisting of SEQ ID NO: 2/10, 18/26, 34/42, 50/58, 66/74, 82/90, 98/106, 114/122, 130/138, 146/154, 162/170, 178/186, 194/202, 210/218, 287/295, 303/311, 319/327, 335/343, 351/359, and 367/375; and further comprise an apelin peptide sequence, e.g. a fragment or analogue of SEQ ID NO: 227, SEQ ID NO: 228, SEQ ID NO: 229 or SEQ ID NO: 230.

In one aspect the invention, an apelin receptor (APNLR) modulator comprises an apelin peptide component and an Ig molecule, such as an IgG molecule. As such, the apelin peptide component may be fused in-frame to the N-terminus or C-terminus of the heavy chain of the Ig molecule. The antibody-apelin fusion proteins (otherwise known as antibody-apelin fusions) may comprise a homodimer comprising two identical heavy chain domains and an apelin peptide component fused in-frame to the N-terminus or C-terminus of one or both heavy chains of the antibody. In other instances, the antibody-apelin fusion protein may be a homodimer comprising two identical heavy chain domains and an apelin peptide component fused in-frame to the N-terminus or C-terminus of one or both light chains of the antibody. In some embodiments, the Ig molecule is an anti-APLNR antibody, thus the heavy and light chain variable regions (HCVR/LCVR) are capable of binding to the APLNR. Exemplary antibody-fusion proteins of the invention comprise heavy and light chain variable region (HCVR/LCVR) sequences selected from the group consisting of SEQ ID NO: 2/10, 18/26, 34/42, 50/58, 66/74, 82/90, 98/106, 114/122, 130/138, 146/154, 162/170, 178/186, 194/202, 210/218, 287/295, 303/311, 319/327, 335/343, 351/359, and 367/375. In other embodiments, the antibody-apelin fusions may comprise antigen-binding fragments including, for example, the variable regions recited herein fused to an apelin peptide or analogue. As such, the antibody-apelin fusions comprise a Fab, F(ab')2 or scFv fragment. A person of ordinary skill in the art, starting with the heavy and light chain variable region sequences disclosed herein, can easily produce various antibody-apelin fusions which comprise one or more apelin peptides thereof.

As with antibody molecules, antibody-apelin fusions may be monospecific or multispecific (e.g., bispecific). A multispecific antibody-apelin fusion will typically comprise at least two different variable domains, wherein one variable domain is capable of specifically binding to APLNR, and a second variable domain may capable of binding to a different epitope on the same antigen (i.e. APLNR) or binding to a different antigen, such as apelin. Any multispecific antibody format may be adapted for use in the context of an antibody-fusion protein of the present invention using routine techniques available in the art.

In some embodiments, the components or peptides of an antibody-fusion protein are separated by a linker (or "spacer") peptide. Such peptide linkers are well known in the art (e.g., polyglycine) and typically allow for proper folding of one or both of the components of the fusion protein. The linker provides a flexible junction region of the component of the fusion protein, allowing the two ends of the molecule to move independently, and may play an important role in retaining each of the two moieties' appropriate functions. Therefore, the junction region acts in some cases as both a linker, which combines the two parts together, and as a spacer, which allows each of the two parts to form its own biological structure and not interfere with the other part. Furthermore, the junction region should create an epitope that will not be recognized by the subject's immune system as foreign, in other words, will not be considered immunogenic. Linker selection may also have an effect on binding activity of the fusion molecule. (See Huston, et al, 1988, *PNAS,* 85:16:5879-83; Robinson & Bates, 1998, *PNAS* 95(11):5929-34; Arai, et al. 2001, *PEDS,* 14(8):529-32; and Chen, X. et al., 2013, *Advanced Drug Delivery Reviews* 65:1357-1369.) In one embodiment, the apelin peptide is connected to the N-terminus or to the C-terminus of the antibody-fusion polypeptide, or fragment thereof, via one or more peptide linkers.

The length of the linker chain may be 2, 3, 4, 5, 6, 7, 8, 9, 10, 11, 12, 13, 14 15 or more amino acid residues, but typically is between 5 and 25 residues. Examples of linkers include polyGlycine linkers, such as Gly-Gly (2Gly), Gly-Gly-Gly (3Gly), 4Gly, 5Gly, 6Gly, 7Gly, 8Gly or 9Gly. Examples of linkers also include Gly-Ser peptide linkers such as Ser-Gly (SG), Gly-Ser (GS), Gly-Gly-Ser (G2S), Ser-Gly-Gly (SG2), G3S, SG3, G4S, SG4, G5S, SG5, G6S, SG6, (G4S)n, (S4G)n, wherein n=1 to 10. (Gly-Gly-Gly-Gly-Ser)3 is also known as (G4S)3 (SEQ ID NO: 233), wherein n=3 indicating that the particular sequence is repeated 3 times. Any one of the linkers described herein may be repeated to lengthen the linker as needed.

In one such embodiment of the invention, the apelin peptide is connected to the N-terminus or to the C-terminus of the antibody-fusion protein, or fragment thereof, via one or more Gly-Ser peptide linkers.

In some embodiments, the peptide linker is selected from the group consisting of (Gly-Gly-Gly-Gly-Ser)1 (SEQ ID NO: 231), (Gly-Gly-Gly-Gly-Ser)2 (SEQ ID NO: 232), and (Gly-Gly-Gly-Gly-Ser)3 (SEQ ID NO: 233).

In other embodiments, a signal peptide is encoded upstream of the antibody-fusion protein in an expression vector. In certain embodiments, a linker or spacer is fused in-frame between the C-terminus of the signal peptide and N-terminus of the antibody-fusion protein. Such signal peptides are known in the art and may be employed to direct the polypeptide into a cell's secretory pathway.

Exemplary apelin fusion proteins of the invention are more stable than apelin peptides alone. Some apelin fusion proteins of the invention are resistant to enzymatic degradation. Exemplary antibody-fusion proteins of the invention comprise heavy and light chain variable region (HCVR/LCVR) sequences fused to apelin peptides and optionally fused to a linker, and are selected from the group consisting of SEQ ID NO: 130/235, 130/237, 239/138, 241/138, 243/138, 245/138, 247/122, 114/249, 114/251, 253/26, 255/26, 257/26, 259/26, 274/138, 275/138, 276/138, 277/138, 278/138, 279/26, 280/26, 281/26, and 282/26.

Epitope Mapping and Related Technologies

The present invention includes anti-APLNR antibodies and antibody-fusion proteins which interact with one or more amino acids of APLNR. For example, the present invention includes anti-APLNR antibodies that interact with one or more amino acids located within an extracellular or transmembrane domain of APLNR. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids of APLNR. Alternatively, the epitope may consist of a plurality of non-contiguous amino acids (or amino acid sequences) of APLNR.

Various techniques known to persons of ordinary skill in the art can be used to determine whether an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., N.Y.), alanine scanning mutational analysis, peptide blots analysis (Reineke, 2004, *Methods Mol Biol* 248:443-463), and peptide cleavage analysis. In addition, methods such as epitope excision, epitope extraction and chemical modification of antigens can be employed (Tomer, 2000, *Protein Science* 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present invention further includes anti-APLNR antibodies that bind to the same epitope as any of the specific exemplary antibodies described herein (e.g. H1M9207N, H2aM9209N, H2aM9222N, H2aM9227N, H2aM9227N, H2aM9228N, H2aM9230N, H2aM9232N, H4H9092P, H4H9093P, H4H9101P, H4H9103P, H4H9104P, H4H9112P, H4H9113P, etc.). Likewise, the present invention also includes anti-APLNR antibodies that compete for binding to APLNR with any of the specific exemplary antibodies described herein (e.g. H1M9207N, H2aM9209N, H2aM9222N, H2aM9227N, H2aM9227N, H2aM9228N, H2aM9230N, H2aM9232N, H4H9092P, H4H9093P, H4H9101P, H4H9103P, H4H9104P, H4H9112P, H4H9113P, etc.). The present invention further includes anti-APLNR antibodies that bind to the same epitope as activating antibodies described herein (e.g. H2aM9228N, H2aM9230N, H2aM9221N, H2aM9223N, H2aM9226N, H2aM9229N, H2aM9224N, and H2aM9225N).

One can easily determine whether an antibody binds to the same epitope as, or competes for binding with, a reference anti-APLNR antibody by using routine methods known in the art and exemplified herein. For example, to determine if a test antibody binds to the same epitope as a reference anti-APLNR antibody of the invention, the reference antibody is allowed to bind to an APLNR protein. Next, the ability of a test antibody to bind to the APLNR molecule is assessed. If the test antibody is able to bind to APLNR following saturation binding with the reference anti-APLNR antibody, it can be concluded that the test antibody binds to a different epitope than the reference anti-APLNR antibody. On the other hand, if the test antibody is not able to bind to the APLNR molecule following saturation binding with the reference anti-APLNR antibody, then the test antibody may bind to the same epitope as the epitope bound by the reference anti-APLNR antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, BIAcore™, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., 1990, Cancer Res. 50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-APLNR antibody, the above-described binding methodology is performed in two orientations: In a first orientation, the reference antibody is allowed to bind to an APLNR protein under saturating conditions followed by assessment of binding of the test antibody to the APLNR molecule. In a second orientation, the test antibody is allowed to bind to an APLNR molecule under saturating conditions followed by assessment of binding of the reference antibody to the APLNR molecule. If, in both orientations, only the first (saturating) antibody is capable of binding to the APLNR molecule, then it is concluded that the test antibody and the reference antibody compete for binding to APLNR. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

Methods for generating monoclonal antibodies, including fully human monoclonal antibodies are known in the art. Any such known methods can be used in the context of the present invention to make human antibodies that specifically bind to human APLNR.

Using VELOCIMMUNE™ technology, for example, or any other known method for generating fully human monoclonal antibodies, high affinity chimeric antibodies to APLNR are initially isolated having a human variable region and a mouse constant region. As in the experimental section below, the antibodies are characterized and selected for desirable characteristics, including affinity, selectivity, epitope, etc. If necessary, mouse constant regions are replaced with a desired human constant region, for example wild-type or modified IgG1, IgG2 or IgG4, to generate a fully human anti-APLNR antibody. While the constant region selected may vary according to specific use, high affinity antigen-binding and target specificity characteristics reside in the variable region. In certain instances, fully human anti-APLNR antibodies are isolated directly from antigen-positive B cells.

Bioequivalents

The anti-APLNR antibodies and antibody fragments of the present invention encompass proteins having amino acid sequences that vary from those of the described antibodies but that retain the ability to bind human APLNR. Such variant antibodies and antibody fragments comprise one or more additions, deletions, or substitutions of amino acids when compared to parent sequence, but exhibit biological activity that is essentially equivalent to that of the described antibodies. Likewise, the anti-APLNR antibody-encoding DNA sequences of the present invention encompass sequences that comprise one or more additions, deletions, or substitutions of nucleotides when compared to the disclosed sequence, but that encode an anti-APLNR antibody or antibody fragment that is essentially bioequivalent to an anti-APLNR antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-APLNR antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-APLNR antibody variants comprising amino acid changes which modify the glycosylation characteristics of the antibodies, e.g., mutations which eliminate or remove glycosylation.

Species Selectivity and Species Cross-Reactivity

The present invention, according to certain embodiments, provides anti-APLNR antibodies that bind to human APLNR but not to APLNR from other species. The present invention also includes anti-APLNR antibodies that bind to human APLNR and to APLNR from one or more non-human species. For example, the anti-APLNR antibodies of the invention may bind to human APLNR and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee APLNR. According to certain exemplary embodiments of the present invention, anti-APLNR antibodies are provided which specifically bind human APLNR (SEQ ID NO: 225) and cynomolgus monkey (e.g., *Macaca fascicularis*) APLNR (SEQ ID NO: 226).

Immunoconjugates

The invention encompasses anti-APLNR monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Multispecific Antibodies

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, *J. Immunol.* 147:60-69; Kufer et al., 2004, *Trends Biotechnol.* 22:238-244. The anti-APLNR antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for human APLNR or a fragment thereof, and the other arm of the immunoglobulin is specific for a second therapeutic target or is conjugated to a therapeutic moiety.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention. See, e.g., U.S. Application Publication No. US20100331527A1, published Dec. 30, 2010, which is herein incorporate by reference.

In some aspects, the antibody, antibody-fusion protein or antigen-binding fragment is a bispecific antibody wherein each antigen-binding fragment of such molecule or antibody comprises a HCVR paired with a LCVR region. In certain embodiments, the bispecific antibody comprises a first antigen-binding fragment and a second antigen binding fragment each comprising different, distinct HCVRs paired with a LCVR region. In some embodiments, the bispecific antibodies are constructed comprising a first antigen-binding fragment that specifically binds a first antigen, wherein the first antigen-binding fragment comprises an HCVR/LCVR pair derived from a first antibody directed against the first antigen, and a second antigen-binding fragment that specifically binds a second antigen, wherein the second antigen-binding fragment comprises an HCVR derived from a second antibody directed against a second antigen paired with an LCVR derived from the first antibody (e.g., the same LCVR that is included in the antigen-binding fragment of the first antibody). In some embodiments, the heavy chain of at least one of the antibodies, i.e. the first antibody or the second antibody or both antibodies, in a bispecific antibody comprises a modified heavy chain constant region In some aspects of the invention, two antibodies, or two heavy chains, having different specificity use the same light chain in a bispecific antibody. In some embodiments, at least one of the heavy chains is modified in the $C_H3$ domain resulting in a differential affinity between each heavy chain of the bispecific antibody and an affinity reagent, such as Protein A, for ease of isolation. In another embodiment, at least one of the heavy chains in such bispecific antibody comprises an amino acid modification at i) 95R or ii) 95R and 96F in the IMGT numbering system (95R and 96F correspond to 435R and 436F in the EU numbering system).

In still other aspects, the antibody is a bispecific antibody wherein the bispecific antibody comprises: (a) a first heavy chain comprising an antigen-binding fragment capable of recognizing and binding to a first target antigen, (b) a second heavy chain comprising an antigen-binding fragment capable of recognizing and binding to a second target antigen, (c) a common light chain antigen-binding fragment capable of recognizing and binding to the first or second target antigen. In another aspect, at least one of the heavy chains of (a) or (b) in such bispecific antibody hereinabove comprises an amino acid modification (i)95R or (ii) 95R and 96F in the IMGT numbering system [(i) 435R or (ii) 435R and 436F (EU numbering)].

Exemplary bispecific formats may be used in the context of the invention comprising any of the HCVR and/or LCVR sequences described herein. In some embodiments, the first antigen is a first epitope on hAPLNR, and the second antigen is a second epitope on hAPLNR. In other embodiments, the first antigen is APLNR and the second antigen is apelin. In certain embodiments, the first antibody comprises an anti-APLNR antigen-binding fragment described herein. In other embodiments, the second antibody comprises an anti-apelin antigen-binding fragment. Such anti-apelin antigen-binding fragments are known in the art (see, e.g. PCT International Publication No. WO2013/012855, published Jan. 24, 2013, which is herein incorporated by reference).

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, *mAbs* 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al. 2013, *J. Am. Chem. Soc.* 9; 135(1):340-6 [Epub: Dec. 21, 2012]).

Further exemplary multispecific formats can be used in the context of the present invention include, without limitation, e.g., involving a first antigen-binding domain that specifically binds a target molecule, and a second antigen-binding domain that specifically binds an internalizing effector protein, wherein such second antigen-binding domains are capable of activating and internalizing the APLNR. (See U.S. Application Publication No. 2013/0243775A1, published on Sep. 19, 2013, which is incorporated by reference.)

pH-Dependent Binding

The present invention provides antibodies, antibody-fusion proteins and antigen-binding fragments thereof that bind APLNR in a pH-dependent manner. For example, an anti-APLNR antibody of the invention may exhibit reduced binding to APLNR at acidic pH as compared to neutral pH. Alternatively, an anti-APLNR antibody of the invention may exhibit enhanced binding to its antigen at acidic pH as compared to neutral pH.

In certain instances, "reduced binding to APLNR at acidic pH as compared to neutral pH" is expressed in terms of a binding quotient of the binding ratio of the antibody to cells expressing APLNR at acidic pH to the binding ratio of the antibody to cells expressing APLNR at neutral pH (or vice versa). For example, an antibody or antigen-binding fragment thereof may be regarded as exhibiting "reduced binding to APLNR at acidic pH as compared to neutral pH" for purposes of the present invention if the antibody or antigen-binding fragment thereof exhibits an acidic/neutral binding quotient of about 3.0 or greater. In certain embodiments, the acidic/neutral binding quotient for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Alternatively, "reduced binding to APLNR at acidic pH as compared to neutral pH" is expressed in terms of a ratio of the $K_D$ value of the antibody binding to APLNR at acidic pH to the $K_D$ value of the antibody binding to APLNR at neutral pH (or vice versa). The term "$K_D$" (M), as used herein, refers to the dissociation equilibrium constant of a particular ligand-receptor interaction. There is an inverse relationship between $K_D$ and binding affinity, therefore the smaller the $K_D$ value, the higher the affinity. Thus, the term "lower affinity" relates to a lower ability to form an interaction and therefore a larger $K_D$ value. For example, an antibody or antigen-binding fragment thereof may be regarded as exhibiting "reduced binding to APLNR at acidic pH as compared to neutral pH" for purposes of the present invention if the antibody or antigen-binding fragment thereof exhibits an acidic/neutral $K_D$ ratio of about 3.0 or greater. In certain embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of about 6.0 or less, about 5.5 or less, or about 5.0 or less. The expression "acidic pH" includes pH values of about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

Therapeutic Formulation and Administration

The invention provides pharmaceutical compositions comprising the anti-APLNR antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA, 1998, *J Pharm Sci Technol* 52:238-311.

The dose of antibody administered to a patient may vary depending upon the age and the size of the patient, target disease, conditions, route of administration, and the like. The preferred dose is typically calculated according to body weight or body surface area. When an antibody of the present invention is used for treating a condition or disease associated with APLNR activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-APLNR antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

Experiments using mouse model systems, such as conducted by the present inventors, have contributed to the identification of various diseases and conditions that can be treated, prevented and/or ameliorated by APLNR antagonism. For example, Apelin(−/−) knockout mice exhibit an obvious impairment of normal developmental angiogenesis in the eye. In addition, APLNR(−/−) mice have altered fluid homeostasis and an altered response to osmotic stress (Roberts, Em et al. 2009, J Endocrinol 202:453-462; Roberts, E M, et al. 2010, J Endocrinol 22:301-308). In another example, APLNR$^{-/-}$ mice showed normal baseline blood pressure and heart rate, but lack the hypotensive response to apelin (Charo, et al. 2009, Am J Physiol Heart Circ Physiol 297: H1904-H1913 [Epub on Sep. 18, 2009]). Furthermore, exemplary anti-APLNR antibodies are antagonists of the receptor and exhibit an APLNR-mediated anti-angiogenic effect in the eye vasculature as measured in a retinal vascular development (RVD) model.

Antagonists of the receptor, such as the functional antagonist derived by modifying apelin-13 at its C-terminal phenylalanine (F) to alanine (A) (i.e. apelin-13(F13A)), were shown to block the hypotensive action of the APLNR (Lee, et al. Endocrinol 2005, 146(1):231-236).

Apelin peptide may promote obesity through adipose tissue expansion. Apelin is induced by hypoxia and drives angiogenesis within the hypoxic interior of expanding adipose tissue. (Kunduzova O, et al., 2008, FASEB J, 22:4146-4153). Anti-APLNR antibodies act as inhibiting agents of this mechanism, in a tissue-specific manner, and can promote weight loss or treat obesity. Therefore, Anti-APLNR antibodies may be administered to treat obesity and to promote weight loss.

Pathological angiogenesis, involved in promoting tumor growth or neovascularization in the retina may be responsive to apelin or APLNR antagonist. (Kojima, Y. and Quertermous, T., 2008, Arterioscler Thromb Vasc Biol, 28:1687-1688; Rayalam, S. et al. 2011, Recent Pat Anticancer Drug Discov 6(3):367-72). As such, anti-APLNR antibodies may be administered to slow tumor growth or metastasis, or to treat cancer and metastatic disease.

Apelin may associate with a progressive overexpression of VEGF and GFAP, suggesting a role for apelin-mediated signaling in the progression of diabetic retinopathy (DR) to a proliferative phase. Anti-APLNR antibodies may be administered for early prevention and treatment of DR (Lu, Q. et al, 2013, *PLoS One* 8(7):e69703).

APLNR antagonists may also reduce angiogenesis and improve function, such as in fibrotic tissues, by ameliorating the effects of an overactive apelin system caused by a pathogenic disease (Principe, et al., 2008, *Hepatology*, 48(4):1193-1201; Reichenbach, et al., 2012, *JPET* 340(3): 629-637). Without being bound by any one theory, blocking the apelin system may slow the formation of excess fibrous connective tissue in an organ or tissue in a reparative or reactive process, such as in a pathological condition like cirrhosis. As such, anti-APLNR antibodies may be used as inhibiting agents administered to slow or prevent the progression of fibrosis, or to treat fibrosis.

The antibodies of the invention are useful, inter alia, for the treatment, prevention and/or amelioration of any disease or disorder associated with or mediated by APLNR expression, signaling, or activity, or treatable by blocking the interaction between APLNR and a APLNR ligand (e.g., apelin) or otherwise inhibiting APLNR activity and/or signaling. For example, the present invention provides methods for treating a disease or disorder selected from the group consisting of obesity, cancer, metastatic disease, retinopathy, fibrosis, and pathological angiogenesis. In one embodiment, the APLNR modulator promotes weight loss. In another embodiment, the APLNR modulator decreases pathological angiogenesis or neovascularization. In other embodiments, the APLNR modulator decreases or inhibits tumor growth.

In other circumstances, including experiments using animal model systems, treatment of various diseases and conditions has been shown effective by APLNR agonism or partial agonism. Agonists of APLNR, such as apelin, have been administered for the management of cardiovascular conditions, such as inotropic agents, specifically positive inotropic agents. Without being bound to a particular theory, positive inotropic agents increase myocardial contractility, and are used to support cardiac function in conditions such as congestive heart failure, myocardial infarction, cardiomyopathy, and others. (See Dai, et al., 2006, *Eur J Pharmacol* 553(1-3): 222-228; Maguire, et al, *Hypertension*. 2009; 54:598-604; and Berry, M., et al., 2004 *Circulation*, 110:11187-11193.) Apelin-induced vasodilation may be protective in ischemia-reperfusion injury. It has been shown that partial agonism of APLNR (with respect to cAMP production) correlates with vasorelaxation in an ex vivo precontracted rat aorta as seen with treatment with the small molecule agonist E339-3D6 (Iturrioz, X, et al., 2010 FASEB 24(5):1506-1517). Promotion of angiogenesis and induction of larger nonleaky vessels by apelin peptides also contributed to functional recovery from ischemia. (Eyries M, et al., 2008, *Circ Res* 103:432-440; Kidoya H, et al., 2010, *Blood* 115:3166-3174).

Apelin receptor agonists are considered pro-angiogenic agents which are administered to increase cardiac output, improve cardiac function, stabilize cardiac function, limit a decrease in cardiac function, or promote new blood vessel growth in an ischemic or damaged area of the heart or other tissue. Thus, agonistic APLNR modulators of the invention are useful to promote angiogenesis and therefore treat ischemia, restore bloodflow to ischemic organs and tissues, for example to treat limb ischemia, peripheral ischemia, renal ischemia, ocular ischemia, cerebral ischemia, or any ischemic disease.

Apelin has also been shown to improve glucose tolerance and enhance glucose utilization, by muscle tissue, in obese insulin-resistant mice (Dray et al., 2008, *Cell Metab* 8:437-445). Apelin KO mice have diminished insulin sensitivity (Yue at al., 2010, *Am J Physiol Endocrinol Metab* 298:E59-E67). As such, agonistic Antibody-Apelin fusion proteins may improve glucose-tolerance in the treatment of insulin-resistant diabetes, and thus may be administered for the management of metabolic conditions related to diabetes.

Changes in muscle apelin mRNA levels are also correlative with whole-body insulin sensitivity improvements (Besse-Patin, A. et al., 2013 Aug. 27, Int J Obes (Lond). doi: 10.1038/ijo.2013.158, [Epub ahead of print]). Due to such metabolic improvements in muscle tissue, and apelin-induced vasodilation, agonistic Antibody-Apelin fusion proteins may also be administered to stimulate muscle growth and endurance.

It has been shown that primary HIV-1 isolates can also use APLNR as a coreceptor and synthetic apelin peptides inhibited HIV-1 entry into CD4-APLNR-expressing cells (Cayabyab, M., et al., 2000, *J. Virol.*, 74: 11972-11976). Agonistic Antibody-Apelin fusion proteins may also treat HIV infection. Apelin-neuroprotection is also seen where apelin peptides act through signaling pathways to promote neuronal survival (Cheng, B, et al., 2012, *Peptides*, 37(1):171-3). Thus, Antibody-Apelin fusion proteins may promote or increase survival of neurons, or treat neuronal injury or neurodegeneration. Apelin receptor agonists have been described as hot flash suppressants. (See WO2012/133825, published Oct. 4, 2012), therefore Antibody-Apelin fusion proteins of the invention may also be administered to treat, improve or suppress hot flash symptoms in a subject.

The antibody-fusion proteins of the invention are useful, inter alia, for the treatment, prevention and/or amelioration of any disease or disorder associated with or mediated by activating or stimulating APLNR expression, signaling, or activity. For example, the present invention provides methods for treating a disease or disorder selected from the group consisting of cardiovascular disease, acute decompensated heart failure, congestive heart failure, myocardial infarction, cardiomyopathy, ischemia, ischemia/reperfusion injury, pulmonary hypertension, diabetes, neuronal injury, neurodegeneration, hot flash symptoms, fluid homeostasis, and HIV infection. In some embodiments, the APLNR modulator is useful to treat or alleviate ischemia and reperfusion injury, such as to limit ischemia/reperfusion (I/R) injury or delay the onset of necrosis of the heart tissue, or to provide preventive treatment, for example, to protect the heart from ischemia/reperfusion (I/R) injury, improve cardiac function, or limit the development myocardial infarction.

In the context of the methods of treatment described herein, the APLNR modulator may be administered as a monotherapy (i.e., as the only therapeutic agent) or in combination with one or more additional therapeutic agents (examples of which are described elsewhere herein).

Combination Therapies and Formulations

The present invention includes compositions and therapeutic formulations comprising any of the APLNR modulators described herein in combination with one or more additional therapeutically active components, and methods of treatment comprising administering such combinations to subjects in need thereof.

The APLNR modulators of the present invention may be co-formulated with and/or administered in combination with, e.g., VEGF inhibitors, including small-molecule angiogenic inhibitors, and antibodies that bind to cytokines such as IL-1, IL-2, IL-3, IL-4, IL-5, IL-6, IL-8, IL-9, IL-11, IL-12, IL-13, IL-17, IL-18, IL-21, IL-23, IL-26, or antagonists of their respective receptors. Other additional therapeutically active components may include blood pressure medication, calcium channel blockers, digitalis, anti-arrhythmics, ACE inhibitors, anti-coagulants, immunosuppressants, pain relievers, vasodilators, etc.

The additional therapeutically active component(s) may be administered just prior to, concurrent with, or shortly after the administration of an APLNR modulator of the present invention; (for purposes of the present disclosure, such administration regimens are considered the administration of an APLNR modulator "in combination with" an additional therapeutically active component). The present invention includes pharmaceutical compositions in which an APLNR modulator of the present invention is co-formulated with one or more of the additional therapeutically active component(s) as described elsewhere herein.

Administration Regimens

According to certain embodiments of the present invention, multiple doses of an APLNR modulator (or a pharmaceutical composition comprising a combination of an APLNR modulator and any of the additional therapeutically active agents mentioned herein) may be administered to a subject over a defined time course. The methods according to this aspect of the invention comprise sequentially administering to a subject multiple doses of an APLNR modulator of the invention. As used herein, "sequentially administering" means that each dose of APLNR modulator is administered to the subject at a different point in time, e.g., on different days separated by a predetermined interval (e.g., hours, days, weeks or months). The present invention includes methods which comprise sequentially administering to the patient a single initial dose of an APLNR modulator, followed by one or more secondary doses of the APLNR modulator, and optionally followed by one or more tertiary doses of the APLNR modulator.

The terms "initial dose," "secondary doses," and "tertiary doses," refer to the temporal sequence of administration of the APLNR modulator of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of APLNR modulator, but generally may differ from one another in terms of frequency of administration. In certain embodiments, however, the amount of APLNR modulator contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of APLNR modulator which is administered to a patient prior to the administration of the very next dose in the sequence with no intervening doses.

The methods according to this aspect of the invention may comprise administering to a patient any number of secondary and/or tertiary doses of an APLNR modulator. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of once a month, then the maintenance doses may be administered to the patient once every six weeks, once every two months, once every three months, etc.).

Diagnostic Uses of the Antibodies

The anti-APLNR antibodies of the present invention may also be used to detect and/or measure APLNR, or APLNR-expressing cells in a sample, e.g., for diagnostic purposes. For example, an anti-APLNR antibody, or fragment thereof, may be used to diagnose a condition or disease characterized by aberrant expression (e.g., over-expression, under-expression, lack of expression, etc.) of APLNR. Exemplary diagnostic assays for APLNR may comprise, e.g., contacting a sample, obtained from a patient, with an anti-APLNR antibody of the invention, wherein the anti-APLNR antibody is labeled with a detectable label or reporter molecule. Antibody-fusion proteins of the invention may be employed in such an assay, wherein the apelin fusion component or the antibody component is labeled with a detectable label or reporter molecule. Alternatively, an unlabeled anti-APLNR antibody can be used in diagnostic applications in combination with a secondary antibody which is itself detectably labeled. The detectable label or reporter molecule can be a radioisotope, such as $^3H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure APLNR in a sample include enzyme-linked immunosorbent assay (ELISA), radioimmunoassay (RIA), and fluorescence-activated cell sorting (FACS).

Samples that can be used in APLNR diagnostic assays according to the present invention include any tissue or fluid sample obtainable from a patient which contains detectable quantities of APLNR protein, or fragments thereof, under normal or pathological conditions. Generally, levels of APLNR in a particular sample obtained from a healthy patient (e.g., a patient not afflicted with a disease or condition associated with abnormal APLNR levels or activity) will be measured to initially establish a baseline, or standard, level of APLNR. This baseline level of APLNR can then be compared against the levels of APLNR measured in samples obtained from individuals suspected of having an APLNR related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Human Antibodies to Human APLNR

An immunogen comprising human APLNR was administered directly, with an adjuvant to stimulate the immune response, to a VELOCIMMUNE® mouse comprising DNA encoding human Immunoglobulin heavy and kappa light chain variable regions. The antibody immune response was monitored by an anti-APLNR immunoassay. When a desired immune response was achieved splenocytes were harvested and fused with mouse myeloma cells to preserve their viability and form hybridoma cell lines. The hybridoma cell lines were screened and selected to identify cell lines that produce anti-APLNR antibodies. Using this technique several anti-APLNR chimeric antibodies (i.e., antibodies possessing human variable domains and mouse constant domains) were obtained; exemplary antibodies generated in this manner were designated as follows: H1M9207N, H2aM9230N, and H2aM9232N. The human variable domains from the chimeric antibodies were subsequently cloned onto human constant domains to make fully human anti-APLNR antibodies as described herein.

Anti-APLNR antibodies were also isolated directly from antigen-positive B cells without fusion to myeloma cells, as described in US Patent Application Publication No. 2007/0280945A1, published on Dec. 6, 2007. Using this method, several fully human anti-APLNR antibodies (i.e., antibodies possessing human variable domains and human constant domains) were obtained; exemplary antibodies generated in this manner were designated as follows: H4H9092P, H4H9093P, H4H9101P, H4H9103P, H4H9104P, H4H9112P, and H4H9113P.

Certain biological properties of the exemplary anti-APLNR antibodies generated in accordance with the methods of this Example are described in detail in the Examples set forth below.

Example 2. Heavy and Light Chain Variable Region Amino Acid Sequences

Table 1 sets forth the heavy and light chain variable region amino acid sequence pairs, and CDR sequences, of selected anti-APLNR antibodies and their corresponding antibody identifiers.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1M9207N | 2 | 4 | 6 | 8 | 10 | 12 | 14 | 16 |
| H2aM9209N | 18 | 20 | 22 | 24 | 26 | 28 | 30 | 32 |
| H2aM9222N | 34 | 36 | 38 | 40 | 42 | 44 | 46 | 48 |
| H2aM9227N | 50 | 52 | 54 | 56 | 58 | 60 | 62 | 64 |
| H2aM9228N | 66 | 68 | 70 | 72 | 74 | 76 | 78 | 80 |
| H2aM9230N | 82 | 84 | 86 | 88 | 90 | 92 | 94 | 96 |
| H2aM9232N | 98 | 100 | 102 | 104 | 106 | 108 | 110 | 112 |
| H4H9092P | 114 | 116 | 118 | 120 | 122 | 124 | 126 | 128 |
| H4H9093P | 130 | 132 | 134 | 136 | 138 | 140 | 142 | 144 |
| H4H9101P | 146 | 148 | 150 | 152 | 154 | 156 | 158 | 160 |
| H4H9103P | 162 | 164 | 166 | 168 | 170 | 172 | 174 | 176 |
| H4H9104P | 178 | 180 | 182 | 184 | 186 | 188 | 190 | 192 |
| H4H9112P | 194 | 196 | 198 | 200 | 202 | 204 | 206 | 208 |
| H4H9113P | 210 | 212 | 214 | 216 | 218 | 220 | 222 | 224 |
| H2aM9221N | 287 | 289 | 291 | 293 | 295 | 297 | 299 | 301 |
| H2aM9223N | 303 | 305 | 307 | 309 | 311 | 313 | 315 | 317 |
| H2aM9226N | 319 | 321 | 323 | 325 | 327 | 329 | 331 | 333 |
| H2aM9229N | 335 | 337 | 339 | 341 | 343 | 345 | 347 | 349 |
| H2aM9224N | 351 | 353 | 355 | 357 | 359 | 361 | 363 | 365 |
| H2aM9225N | 367 | 369 | 371 | 373 | 375 | 377 | 379 | 381 |

Antibodies are typically referred to herein according to the following nomenclature: Fc prefix (e.g. "H1M," or "H4H"), followed by a numerical identifier (e.g. "9207," "9209," or "9230" as shown in Table 1), followed by a "P," or "N" suffix. Thus, according to this nomenclature, an antibody may be referred to herein as, e.g., "H1M9207N," "H2aM9209N," "H4H9113P," etc. The H2aM, and H4H prefixes on the antibody designations used herein indicate the particular Fc region isotype of the antibody. For example, an "I-11M" antibody has a mouse IgG1 Fc, and "H2aM" antibody has a mouse IgG2a Fc, whereas an "H4H" antibody has a human IgG4 Fc. As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1—will remain the same, and the binding properties are expected to be identical or substantially similar regardless of the nature of the Fc domain. In one example, the antibody designated H2aM9209N was engineered to have a human IgG4 Fc domain. Thus, the antibody designated herein as H4H9209N has a human IgG4 domain and has the same heavy chains (HC) or light chains (LC), and thus substantially the same binding and cellular activity characteristics as antibody H2aM9209N.

Example 3. Generation of Antibody-Fusion Proteins

To manufacture the nucleic acid encoding the antibody fusion proteins of the invention, the heavy and light chain variable region amino acid sequence pairs, and CDR sequences, of selected anti-APLNR antibodies were amplified via polymerase chain reaction and either the heavy chain (HC) or light chain (LC) was ligated to sequence encoding apelin-13 (SEQ ID NO: 228), or to modified apelin peptides, such as the C-terminal truncated apelin-Cter9 (SEQ ID NO: 270), apelin-Cter10 (SEQ ID NO: 271), or apelin-Cter11 (SEQ ID NO: 262). Contiguous nucleic acid sequences that encode the apelin-containing antibody-fusion proteins of Table 2A and Table 2B were cloned into expression vectors using standard PCR and restriction endonuclease cloning techniques.

Table 2A identifies heavy and light chain variable region amino acid sequence pairs, heavy chain Fc regions, and apelin fusion pattern of selected antibody-fusion proteins and their corresponding antibody-fusion nomenclature. In some exemplified antibody-fusion proteins, the apelin peptide is fused to the heavy chain variable region (HCVR), and in other examples, the apelin peptide is fused to the light chain variable region (LCVR) or the light chain (which may or may not include a light chain constant region). In some examples, the apelin peptide is fused to the polypeptide via a linker. Table 2B indicates certain exemplified sequence pairs, for example either the heavy or light chain sequence is fused to an apelin sequence (fusion).

TABLE 2A

| Antibody- Fusion Designation | HCVR SEQ ID NO: | HC constant region | LCVR SEQ ID NO: | Apelin-13 (SEQ ID NO: 228) fused to: LC or HC |
|---|---|---|---|---|
| H4H9093P-1-NVK3 | 130 | human IgG4 Fc | 138 | N-terminal end LC with (G4S)3 linker |
| H4H9093P-2-CVK3 | 130 | human IgG4 Fc | 138 | C-terminal end LC with (G4S)3 linker |
| H4H9093P-3-NVH3 | 130 | human IgG4 Fc | 138 | N-terminal end HC with (G4S)3 linker |
| H4H9093P-4-NVH0 | 130 | human IgG4 Fc | 138 | N-terminal end HC with no linker |
| H4H9093P-5-NVH1 | 130 | human IgG4 Fc | 138 | N-terminal end HC with G4S linker |
| H4H9093P-6-NVH2 | 130 | human IgG4 Fc | 138 | N-terminal end HC with (G4S)2 linker |
| H4H9092P-1-NVH3 | 114 | human IgG4 Fc | 122 | N-terminal end HC with (G4S)3 linker |
| H4H9092P-2-NVK3 | 114 | human IgG4 Fc | 122 | N-terminal end LC with (G4S)3 linker |
| H4H9092P-3-CVK3 | 114 | human IgG4 Fc | 122 | C-terminal end LC with (G4S)3 linker |
| H4H9209N-1-NVH0 | 18 | human IgG4 Fc | 26 | N-terminal end HC with no linker |
| H4H9209N-2-NVH1 | 18 | human IgG4 Fc | 26 | N-terminal end LC with G4S linker |
| H4H9209N-3-NVH2 | 18 | human IgG4 Fc | 26 | N-terminal end HC with (G4S)2 linker |
| H4H9209N-4-NVH3 | 18 | human IgG4 Fc | 26 | N-terminal end HC with (G4S)3 linker |

| Antibody- Fusion Designation | HCVR SEQ ID NO: | HC constant region | LCVR SEQ ID NO: | Modified Apelin fused to HC |
|---|---|---|---|---|
| H4H9093P-APN9-(G4S)3 | 130 | human IgG4 Fc | 138 | Apelin-Cter9 (SEQ ID NO: 270) N-terminal end HC fusion with (G4S)3 linker |
| H4H9093P-APN10-(G4S)3 | 130 | human IgG4 Fc | 138 | Apelin-Cter10 (SEQ ID NO: 271) N-terminal end HC fusion with (G4S)3 linker |
| H4H9093P-APN11-(G4S)3 | 130 | human IgG4 Fc | 138 | Apelin-Cter11 (SEQ ID NO: 262) N-terminal end HC fusion with (G4S)3 linker |
| H4H9093P-APN11 + S -(G4S)3 | 130 | human IgG4 Fc | 138 | Apelin-Cter11 + S (SEQ ID NO: 272) N-terminal end HC fusion with (G4S)3 linker |
| H4H9093P-APNV5-11-(G4S)3 | 130 | human IgG4 Fc | 138 | Apelin-V5linker-Cter11 (SEQ ID NO: 273) N-terminal end HC fusion with (G4S)3 linker |
| H4H9209N-APN9-(G4S)3 | 18 | human IgG4 Fc | 26 | Apelin-Cter9 (SEQ ID NO: 270) N-terminal end HC fusion with (G4S)3 linker |

TABLE 2A-continued

| | | | | |
|---|---|---|---|---|
| H4H9209N-APN10-(G4S)3 | 18 | human IgG4 Fc | 26 | Apelin-Cter10 (SEQ ID NO: 271) N-terminal end HC fusion with (G4S)3 linker |
| H4H9209N-APN11-(G4S)3 | 18 | human IgG4 Fc | 26 | Apelin-Cter11 (SEQ ID NO: 262) N-terminal end HC fusion with (G4S)3 linker |
| H4H9209N-APN11 + S -(G4S)3 | 18 | human IgG4 Fc | 26 | Apelin-Cter11 + S (SEQ ID NO: 272) N-terminal end HC fusion with (G4S)3 linker |

TABLE 2B

| | Amino acid sequence pairs | |
|---|---|---|
| Antibody- Fusion Designation | HCVR fusion or HCVR SEQ ID NO: | LC fusion, LCVR fusion or LCVR SEQ ID NO: |
| H4H9093P-1-NVK3 | 130 (HCVR) | 235 (LCVR fusion) |
| H4H9093P-2-CVK3 | 130 (HCVR) | 237 (LC fusion) |
| H4H9093P-3-NVH3 | 239 (HCVR fusion) | 138 (LCVR) |
| H4H9093P-4-NVH0 | 241 (HCVR fusion) | 138 (LCVR) |
| H4H9093P-5-NVH1 | 243 (HCVR fusion) | 138 (LCVR) |
| H4H9093P-6-NVH2 | 245 (HCVR fusion) | 138 (LCVR) |
| H4H9092P-1-NVH3 | 247 (HCVR fusion) | 122 (LCVR) |
| H4H9092P-2-NVK3 | 114 (HCVR) | 249 (LCVR fusion) |
| H4H9092P-3-CVK3 | 114 (HCVR) | 251 (LC fusion) |
| H4H9209N-1-NVH0 | 253 (HCVR fusion) | 26 (LCVR) |
| H4H9209N-2- NVH1 | 255 (HCVR fusion) | 26 (LCVR) |
| H4H9209N-3- NVH2 | 257 (HCVR fusion) | 26 (LCVR) |
| H4H9209N-4- NVH3 | 259 (HCVR fusion) | 26 (LCVR) |
| H4H9093P-APN9-(G4S)3 | 274 (HCVR fusion) | 138 (LCVR) |
| H4H9093P-APN10-(G4S)3 | 275 (HCVR fusion) | 138 (LCVR) |
| H4H9093P-APN11-(G4S)3 | 276 (HCVR fusion) | 138 (LCVR) |
| H4H9093P-APN11 + S -(G4S)3 | 277 (HCVR fusion) | 138 (LCVR) |
| H4H9093P-APNV5-11-(G4S)3 | 278 (HCVR fusion) | 138 (LCVR) |
| H4H9209N-APN9-(G4S)3 | 279 (HCVR fusion) | 26 (LCVR) |
| H4H9209N-APN10-(G4S)3 | 280 (HCVR fusion) | 26 (LCVR) |
| H4H9209N-APN11-(G4S)3 | 281 (HCVR fusion) | 26 (LCVR) |
| H4H9209N-APN11 + S-(G4S)3 | 282 (HCVR fusion) | 26 (LCVR) |

Certain biological properties of the exemplary antibody-fusion proteins generated in accordance with these methods are described in detail in the Examples set forth below.

Example 4. Antibody and Antibody-Fusion Protein Binding to Human APLNR as Determined by FACS Analysis Binding ratios for human APLNR binding to purified anti-APLNR monoclonal antibodies were determined by a fluorescence-activated cell sorting (FACS) binding assay. HEK293 cell lines stably expressing the full-length human APLNR (hAPLNR; SEQ ID NO: 225) or the full length cynomolgus APLNR (MfAPLNR; SEQ ID NO: 226) along with a luciferase reporter [cAMP response element (CRE, 4X)-luciferase-IRES-GFP] were generated by well-known methods. The resulting stable cell lines, HEK293/CRE-luc/hAPLNR and HEK293/CRE-luc/MfAPLNR, were maintained in DMEM containing 10% FBS, NEAA, and penicillin/streptomycin with either 100 pg/mL Hygromycin B for hAPLNR cells or 500 µg/mL G418 for MfAPLNR cells.

For the FACS analysis, HEK293 parental, HEK293/CRE-luc/hAPLNR, and, HEK293/CRE-luc/mfAPLNR cells were dissociated using Enzyme Free Dissociation reagent (#S-004, Millipore, Billerica, Mass., USA) and $10^6$ cells/well were plated onto 96-well v-bottom plates in PBS containing 1% FBS. The cells were then incubated with 10 µg/mL of anti-APLNR antibodies or negative isotype control antibodies for 30 minutes at 4° C., followed by washing with PBS containing 1% FBS and incubation with 4 µg/mL of either anti-mouse IgG antibody conjugated with Alexa 647 (#115-607-003, Jackson ImmunoResearch, West Grove, Pa., USA) or anti-human IgG antibody conjugated with Alexa 488 (#109-547-003, Jackson ImmunoResearch) for 30 minutes at 4° C. Cells were then filtered and analyzed on Accuri Flow Cytometer (BD Biosciences, San Jose, Calif., USA). Unstained and secondary antibody alone controls were also tested for binding to all cell lines. The results were analyzed using FlowJo version 9.52 software (Tree Star, Inc., Ashland, Oreg., USA) and geometric mean of fluorescence for viable cells was determined. Geometric mean (Geom. mean) of fluorescence for each antibody was then normalized to geometric mean of unstained cells to obtain relative binding of antibody (binding ratios) per each cell type: HEK293 (parental), HEK293/CRE-luc/hAPLNR and HEK293/CRE-luc/MfAPLNR.

Binding ratios for different anti-APLNR monoclonal antibodies are shown in Tables 3 and 4. As shown in Table 3, seven anti-APLNR antibodies bound to HEK293/CRE-luc/hAPLNR cells with binding ratios ranging from 452 to 4098 fold and to HEK293/CRE-luc/MfAPLNR cells with binding ratios ranging from 31 to 1438 fold. The anti-APLNR antibodies tested bound to HEK293 parental cells with binding ratios ranging from 2 to 9 fold. The anti-mouse IgG secondary antibody alone and mouse IgG (mIgG) control antibody bound to cells with binding ratios ranging from 1 to 7 fold. As shown in Table 4, 7 additional anti-APLNR antibodies bound to HEK293/CRE-luc/hAPLNR cells with binding ratios ranging from 2 to 61 fold and to HEK293/CRE-luc/MfAPLNR cells with binding ratios ranging from 1 to 31 fold. The anti-APLNR antibodies tested bound to HEK293 parental cells with binding ratios ranging from 1 to 3 fold. The anti-human IgG secondary antibody alone and isotype control antibody bound to cells with binding ratios ranging from 1 to 2 fold.

TABLE 3

Binding of anti-APLNR antibodies to HEK293, HEK293/CRE-luc/hAPLNR and HEK293/CRE-luc/MfAPLNR cell lines.

| | Binding Ratio of Geom. Mean to Unstained Cells | | |
|---|---|---|---|
| Antibody | HEK293 Parental | 293/Cre-luc/hAPLNR | 293/Cre-luc/MfAPLNR |
| H1M9207N | 4 | 2179 | 1307 |
| H2aM9209N | 9 | 1643 | 818 |
| H2aM9222N | 2 | 452 | 31 |
| H2aM9227N | 4 | 4098 | 1438 |
| H2aM9228N | 3 | 1491 | 108 |
| H2aM9230N | 3 | 2938 | 658 |
| H2aM9232N | 6 | 2857 | 678 |
| mIgG control | 2 | 7 | 6 |
| Secondary Antibody alone | 2 | 4 | 3 |
| Unstained | 1 | 1 | 1 |

TABLE 4

Binding of anti-APLNR antibodies to HEK293, HEK293/CRE-luc/hAPLNR and HEK293/CRE-luc/MfAPLNR cell lines.

| | Binding Ratio of Geom. Mean to Unstained Cells | | |
|---|---|---|---|
| Antibody | HEK293 Parental | 293/Cre-luc/hAPLNR | 293/Cre-luc/MfAPLNR |
| H4H9092P | 3 | 37 | 20 |
| H4H9093P | 3 | 61 | 31 |
| H4H9101P | 1 | 3 | 2 |
| H4H9103P | 2 | 3 | 2 |
| H4H9104P | 1 | 2 | 1 |
| H4H9112P | 1 | 2 | 2 |
| H4H9113P | 1 | 2 | 1 |
| Isotype control | 1 | 2 | 2 |
| Secondary Antibody alone | 1 | 2 | 2 |
| Unstained | 1 | 1 | 1 |

As shown in Tables 3 and 4, several anti-APLNR antibodies of the present invention bind with specificity to the APLNR.

In addition, 13 antibodies with Apelin fused at their N- or C-terminus were tested for their ability to bind HEK293/CRE-luc/hAPLNR and HEK293/CRE-luc/MfAPLNR cells. As shown in Table 5, H4H9093P with Apelin fused to its N- or C-terminus demonstrated binding to HEK293/CRE-luc/hAPLNR cells with binding ratios ranging from 31 to 151 fold and to HEK293/CRE-luc/MfAPLNR cells binding ratios ranging from 16 to 54 fold, while the parental antibody, H4H9093P, bound HEK293/CRE-luc/hAPLNR cells with a binding ratio of 61 fold and HEK293/CRE-luc/MfAPLNR cells with a binding ratio of 31 fold. As shown in Table 5, H4H9092P with Apelin fused to its N- or C-terminus demonstrated binding to HEK293/CRE-luc/hAPLNR cells with binding ratios ranging from 16 to 79 fold and to HEK293/CRE-luc/MfAPLNR cells with binding ratios ranging from 6 to 31 fold, while the parental antibody, H4H9092P, bound HEK293/CRE-luc/hAPLNR cells with a binding ration of 37 fold and HEK293/CRE-luc/MfAPLNR cells with a binding ratio of 20 fold. As shown in Table 5, H4H9209N with Apelin fused to its N-terminus demonstrated binding to HEK293/CRE-luc/hAPLNR cells with binding ratios ranging from 106 to 121 fold and to HEK293/CRE-luc/MfAPLNR cells with binding ratios ranging from 43 to 52 fold, while the parental antibody, H4H9209N, bound HEK293/CRE-luc/hAPLNR cells with a binding ratio of 82 fold and HEK293/CRE-luc/MfAPLNR cells with a binding ratio of 42 fold.

The antibody-apelin fusions and control antibodies demonstrated binding to HEK293 parental cells in this assay with binding ratios ranging from 2 to 16 fold. Anti-human IgG secondary antibody alone, anti-myc antibody fused to Apelin at the N-terminus, and the isotype control antibody bound to cells with binding ratio ratios ranging from 1 to 12 fold.

TABLE 5

Binding of antibody-fusion proteins to HEK293, HEK293/CRE-luc/hAPLNR and HEK293/CRE-luc/MfAPLNR cell lines.

| | | Binding Ratio of Geom. Mean to Unstained Cells | | |
|---|---|---|---|---|
| Parental Antibody | Description of Modification | HEK293 Parental | 293/Cre-luc/hAPLNR | 293/Cre-luc/MfAPLNR |
| H4H9093P | No modification | 3 | 61 | 31 |
| H4H9093P-1-NVK3 | Nter Vk fusion with (G4S)3 linker | 2 | 31 | 16 |
| H4H9093P-2-CVK3 | Cter Vk fusion with (G4S)3 linker | 3 | 60 | 28 |
| H4H9093P-3-NVH3 | Nter VH fusion with (G4S)3 linker | 3 | 130 | 49 |
| H4H9093P-4-NVH0 | Nter VH fusion with no linker | 4 | 140 | 52 |
| H4H9093P-5-NVH1 | Nter VH fusion with G4S linker | 3 | 151 | 54 |
| H4H9093P-6-NVH2 | Nter VH fusion with (G4S)2 linker | 3 | 139 | 47 |
| H4H9092P | No modification | 3 | 37 | 20 |
| H4H9092P-1-NVH3 | Nter VH fusion with (G4S)3 linker | 2 | 79 | 31 |
| H4H9092P-2-NVK3 | Nter Vk fusion with (G4S)3 linker | 2 | 16 | 6 |
| H4H9092P-3-CVK3 | Cter Vk fusion with (G4S)3 linker | 2 | 31 | 15 |
| H4H9209N | No modification | 16 | 82 | 42 |
| H4H9209N-1-NVH0 | Nter VH fusion with no linker | 9 | 106 | 43 |
| H4H9209N-2-NVH1 | Nter VH fusion with G4S linker | 15 | 107 | 51 |
| H4H9209N-3-NVH2 | Nter VH fusion with (G4S)2 linker | 12 | 121 | 52 |
| H4H9209N-4-NVH3 | Nter VH fusion with (G4S)3 linker | 14 | 121 | 51 |
| Anti-myc 9E10 | Nter VH fusion with (G4S)3 linker | 1 | 12 | 3 |
| Isotype control | | 1 | 2 | 2 |
| Secondary Antibody alone | | 1 | 2 | 2 |
| Unstained | | 1 | 1 | 1 |

As shown in Table 5, several antibody-fusion proteins of the present invention bind with specificity to the APLNR.

Example 5. Anti-APLNR Antibodies Modulate Cell Signaling Through APLNR

The ability of anti-APLNR antibodies to activate hAPLNR-mediated cell signaling was measured using a cyclic AMP assay. The hAPLNR is a 7-transmembrane G-protein coupled receptor (GPCR). When activated by its endogenous ligand, Apelin, it inhibits cAMP production suggesting that it is coupled to inhibitory G-proteins ($G_i$) (Pitkin et al, 2010, Pharmacol. Rev. 62(3):331-342). Apelin is processed into a number of isoforms from a prepropeptide, and pyroglutamyl Apelin-13, (Pyr$^1$)Apelin-13 (referred to in this Example as 'Apelin') is one of the more potent isoforms known to activate hAPLNR.

A HEK293 cell line was transfected to stably express the full-length human hAPLNR (amino acids 1-380 of accession number NP_005152.1; SEQ ID NO: 225), along with a luciferase reporter [cAMP response element (CRE,4X)-luciferase-IRES-GFP]. The resulting cell line, HEK293/CRE-luc/hAPLNR, was maintained in DMEM containing 10% FBS, NEAA, pencillin/streptomycin, and 100 μg/mL Hygromycin B.

To test the $G_i$-coupled activation by hAPLNR, HEK293/CRE-luc/hAPLNR cells are seeded onto 96-well assay plates at 20,000 cells/well in OPTIMEM (Invitrogen, #31985-070) containing 0.1% FBS, pencillin/streptomycin, and L-glutamine and incubated at 37° C. in 5% $CO_2$ overnight. The next morning, in order to measure hAPLNR activation via inhibition of Forskolin-induced cAMP, Apelin ((Pyr1)Apelin-13, Bachem, #H-4568) was serially diluted (1:3) from 100 nM to 0.002 nM (including a control sample containing no Apelin), added to cells with 5 μM, 7.5 μM, or 10 μM Forskolin (Sigma, #F6886). To measure the ability of antibodies or Apelin-antibody fusions (see also Example 9) to activate hAPLNR, antibodies were serially diluted either 1:3 from 500 nM to 0.03 nM, 1:3 from 100 nM to 0.002 nM, 1:4 from 100 nM to 0.0001 nM, or 1:4 from 10 nM to 0.00001 nM, then mixed with 5 μM, 7.5 μM or 10 μM Forskolin, and added to the cells without exogenous Apelin. Testing of antibodies included a no antibody control. To measure the ability of antibodies or Apelin-antibody fusions to inhibit hAPLNR, antibodies were serially diluted at either 1:3 from 500 nM to 0.03 nM or from 100 nM to 0.002 nM, 1:4 from 100 nM to 0.0001 nM, or 1:4 from 10 nM to 0.00001 nM, including a no antibody control and incubated with cells for 1 hour at room temperature. After incubation, a mixture with 5 μM Forskolin and 100 pM Apelin was added to cells. Luciferase activity was detected after 5.5 hours of incubation at 37° C. and in 5% $CO_2$ followed by addition of OneGlo substrate (Promega, #E6051) on a Victor X instrument (Perkin Elmer).

The results of all assays were analyzed using nonlinear regression (4-parameter logistics) within Prism 5 software (GraphPad). Activation by the antibodies was calculated as a percentage of the maximum activation seen in the Apelin dose response. Inhibition by the antibodies was calculated as the difference between the maximum and minimum RLU values for each antibody as a percentage of the RLU range of 0-100 pM Apelin.

Unmodified anti-APLNR antibodies were tested for their ability to activate the hAPLNR by measuring the regulation of Forskolin activation in HEK293/CRE-luc/hAPLNR cells. As shown in Table 6A, 13 out of 14 unmodified anti-APLNR antibodies, when tested without Apelin, did not demonstrate activation of hAPLNR at 100 nM, the highest antibody dose tested, while one antibody, H2aM9227N, demonstrated 12% of maximum Apelin activation at 100 nM. As shown in Table 6B, 11 out of 12 unmodified anti-APLNR antibodies, when tested without Apelin, demonstrated activation of hAPLNR with 21 to 69% of maximum Apelin activation at 500 nM, the highest antibody dose tested, while one antibody, H2aM9232N, did not demonstrate any measurable activation of hAPLNR at any concentration tested. Apelin alone activated hAPLNR with $EC_{50}$ values ranging from 35 pM to 44 pM, as shown in Tables 6A and 6B. None of the isotype control antibodies demonstrated any activation of hAPLNR.

Unmodified anti-APLNR antibodies were tested for their ability to inhibit hAPLNR by measuring the regulation of Forskolin activation in HEK293/CRE-luc/hAPLNR cells in the presence of 100 pM Apelin. As shown in Tables 6C and 6D, several unmodified anti-APLNR antibodies, when tested in the presence of Apelin, demonstrated inhibition of 26 to 98% of 100 pM Apelin activation ($IC_{50}$ values ranging from 2.4 nM to >100 nM). Some of these antibodies also behave as partial agonists (see Table 6B). Three antibodies tested, H2aM9209N, H2aM9222N, and H4H9093P demonstrated weak maximum blockade of Apelin ranging from 6 to 11%, but $IC_{50}$ values could not be determined. Six antibodies tested (H4H9092P, H4H9101P, H4H9103P, H4H9104P, H4H9112P, and H4H9113P) did not demonstrate any measurable blockade of hAPLNR signaling. Apelin alone activated hAPLNR with $EC_{50}$ values ranging from 41 pM to 44 pM, as shown in Tables 6C and 6D. None of the isotype control antibodies demonstrated any inhibition of hAPLNR.

TABLE 6A

Activation of hAPLNR by 100 nM of unmodified anti-APLNR antibodies

| $EC_{50}$ of Apelin with Forskolin(M) Antibody tested | 3.5E−11 (at 10 uM Forskolin) % Activation at 100 nM mAb (at 10 uM Forskolin) | 4.4E−11 (at 5 uM Forskolin) % Activation at 100 nM mAb (at 5 uM Forskolin) |
|---|---|---|
| H1M9207N | No Activation | Not tested |
| H2aM9209N | No Activation | Not tested |
| H2aM9222N | No Activation | Not tested |
| H2aM9227N | 12% | Not tested |
| H2aM9228N | No Activation | Not tested |
| H2aM9230N | No Activation | Not tested |
| H2aM9232N | No Activation | Not tested |
| H4H9092P | Not tested | No Activation |
| H4H9093P | Not tested | No Activation |
| H4H9101P | Not tested | No Activation |
| H4H9103P | Not tested | No Activation |
| H4H9104P | Not tested | No Activation |
| H4H9112P | Not tested | No Activation |
| H4H9113P | Not tested | No Activation |
| Isotype control 1 | No Activation | Not tested |
| Isotype control 2 | Not tested | No Activation |

TABLE 6B

Activation of hAPLNR by 500 nM of unmodified anti-APLNR antibodies

| $EC_{50}$ of Apelin with Forskolin (M) Antibody tested | 6.3E−12 (at 7.5 uM Forskolin) % Activation at 500 nM mAb (at 7.5 uM Forskolin) |
|---|---|
| H2aM9222N | 21% |
| H2aM9227N | 45% |
| H2aM9228N | 49% |
| H2aM9230N | 52% |
| H2aM9232N | No Activation |
| H2aM9221N | 64% |
| H2aM9223N | 39% |
| H2aM9224N | 67% |
| H2aM9225N | 69% |
| H2aM9226N | 61% |
| H2aM9229N | 66% |
| Isotype control 1 | No Activation |

TABLE 6C

Inhibition of hAPLNR by unmodified anti-APLNR antibodies

| Antibody tested | $EC_{50}$ of Apelin with Forskolin (M) 4.1E-11 (at 5 uM Forskolin) | % Inhibition at 100 nM antibody ($IC_{50}$ [M]), in the presence of 100 pM Apelin (at 5 μM Forskolin) |
|---|---|---|
| H1M9207N | 83% | (3.0E-09) |
| H2aM9209N | 7% | (IC) |
| H2aM9222N | 11% | (IC) |
| H2aM9227N | 33% | (4.3E-09) |
| H2aM9228N | 26% | (>1.0E-07) |
| H2aM9230N | 49% | (2.4E-09) |
| H2aM9232N | 98% | (4.2E-09) |
| H2aM9221N | 28% | (5.0E-09) |
| H2aM9223N | 33% | (1.2E-08) |
| H2aM9224N | 29% | (3.6E-09) |
| H2aM9225N | 28% | (3.5E-09) |
| H2aM9226N | 30% | (2.9E-09) |
| H2aM9229N | 38% | (3.5E-09) |
| Isotype control 1 | No Inhibition | |

IC = $IC_{50}$ value could not be determined

TABLE 6D

Inhibition of hAPLNR by unmodified anti-APLNR antibodies

| Antibody tested | $EC_{50}$ of Apelin with Forskolin (M) 4.4E-11 (at 5 uM Forskolin) | % Inhibition at 100 nM antibody, in the presence of 100 pM Apelin (at 5 μM Forskolin) |
|---|---|---|
| H4H9092P | | No Inhibition |
| H4H9093P | | 6% |
| H4H9101P | | No Inhibition |
| H4H9103P | | No Inhibition |
| H4H9104P | | No Inhibition |
| H4H9112P | | No Inhibition |
| H4H9113P | | No Inhibition |
| Isotype control 2 | | No Inhibition |

Example 6. APLNR-Mediated Receptor Signaling by Anti-APLNR Antibodies as Measured in the pERK Assay To further measure the effect of anti-APLNR antibodies of the invention on the APLNR signaling pathway, an assay was used to quantify the amount of phosphorylated ERK1/2 (pERK1/2) and total ERK from an APLNR expressing cell line (herein referred to as a "pERK assay"). A Chinese hamster ovary (CHO) cell line was transfected to stably express the full-length human APLNR (hAPLNR; SEQ ID NO: 225). The resulting cell line, CHO/hAPLNR, was maintained in Ham's F12 containing 10% FBS, penicillin/streptomycin, L-glutamine, and 250 pg/mL Hygromycin B.

For the assay, CHO/hAPLNR cells were seeded onto 96 well assay plates at 10,000 cells/well in Ham's F12 containing 10% FBS, penicillin/streptomycin, L-glutamine, and 250 pg/mL Hygromycin B. The next day, to induce expression of the APLNR and prepare the cells for the pERK assay, plates were washed and then incubated overnight in Ham's F12 containing 1% BSA, 0.1% FBS, penicillin/streptomycin, L-glutamine and 0.5 μg/ml doxycycline. After incubation, cells were washed again, and then serial dilutions ranging from $1\times10^{-6}$ to $1\times10^{-13}$ M of anti-APLNR antibodies, Apelin-13 peptide (Celtek Peptides custom synthesis, Lot #110712), or an isotype control antibody were added to the cells. Cells were incubated at 37° C. in 5% $CO_2$ for 15 minutes. Cells were then washed and ELISAOne lysis buffer mix (Cat. #EBF001, TGR BioSciences, Adelaide, Australia) was added to the plates and incubated at room temperature for 10 minutes while shaking at 300 rpm. Forty μL (40 μL) of cell lysate was then transferred to each ELISA plate, one to measure pERK1/2 and one to measure total ERK. The ELISAs to detect pERK1/2 (ELISAOne #EKT001, TGR BioSciences) and to detect total ERK (ELISAOne #EKT011, TGR BioSciences) were performed as per the manufacturer's specifications. The fluorescence signals were then measured using a Spectramax plate reader (Molecular Devices, Sunnyvale, Calif., USA). The ratio of measured pERK1/2 to measured total ERK was calculated and the results were analyzed using GraphPad Prism software.

As shown in Table 7, two (2) anti-APLNR antibodies tested, H2aM9222N and H2aM9228N, increased the ratio of pERK1/2 to total ERK1/2 with $EC_{50}$ values of 47.61 nM and 64.12 nM, respectively, while Apelin-13 alone increased the ratio of pERK1/2 to total ERK1/2 with an $EC_{50}$ value 38.86 pM. The maximum increase in the ratio of pERK1/2 to total ERK1/2 for the 2 antibodies was less than that of Apelin-13. One anti-APLNR antibody, H2aM9232N, decreased the ratio of pERK1/2 to total ERK with an $IC_{50}$ value of 208.7 nM.

TABLE 7

Activity of anti-APLNR antibodies and Apelin-13 peptide in pERK/total ERK assays

| Antibody tested | Activating $EC_{50}$ (M) | Inhibiting $IC_{50}$ (M) |
|---|---|---|
| H2aM9222N | 4.7861E-08 | — |
| H2aM9228N | 6.412E-08 | — |
| H2aM9232N | — | 2.087E-07 |
| Apelin-13 | 3.886E-11 | — |

Example 7. Effect of Systemic Administration of an Anti-APLNR Antagonist Antibody (50 mg/kg) in a Blinded Retinal Vascular Development (RVD) Model To assess the in vivo characteristics of select anti-APLNR antibodies of the invention, their ability to block APLNR-mediated angiogenesis in the eye vasculature was measured.

A retinal vascular development (RVD) model was used to evaluate the effects of an antagonistic anti-APLNR antibody on blood vessel outgrowth in the normal developing retina of mouse pups that were of a mixed background strain (75% C57BL6 and 25% Sv129) and homozygous for expression of human APLNR in place of mouse APLNR (humanized APLNR mice). Pups were subcutaneously injected on postnatal day 2 (P2) with either 50 mg/kg of an anti-APLNR antagonist antibody, H2aM9232N, or an irrelevant human Fc (hFc) control. Reagents were masked and labeled as Solution A and Solution B to prevent experimenter bias. At postnatal day 5, tissue samples were collected and then fixed in PBS containing 4% paraformaldehyde. Fixed tissue samples were washed with PBS three times for 15 minutes, and subsequently stained with GS Lectin I (Vector Laboratories, #FL-1101) diluted 1:200 in 1x PBS containing 1% BSA in 0.25% Triton-X 100 overnight at 25° C. to visualize retinal vasculature. The following day, stained samples were rinsed with PBS three times for 15 minutes each, flatmounted onto slides, and coverslips were subsequently mounted using Prolong Gold (Invitrogen, #P36930). Images were taken at 20 times magnification using an epi-fluorescent microscope (Nikon Eclipse 80). The vascularized areas in the retina were measured from acquired images from this assay using Adobe Photoshop CS6 extended. Statistical differences between the results obtained from the IgG control antibody and H2aM9232N treated samples were assessed using a two tailed, unpaired Student T-test (**, p<0.001). Only after retinal vasculature area measurements and statistical analysis were completed, the sample identities were unmasked.

TABLE 8

Analysis of the effects of an anti-APLNR antibody in RVD model

| Antibody | Animal # | Eye | Retinal blood vessel outgrowth (mm$^2$) |
|---|---|---|---|
| IgG control antibody | Mouse 1 | OD | 4.09 |
| | Mouse 1 | OS | 4.44 |
| | Mouse 2 | OD | 3.80 |
| | Mouse 2 | OS | 3.66 |
| | Mouse 3 | OD | 3.87 |
| | Mouse 3 | OS | 4.11 |
| | Mouse 4 | OD | 4.95 |
| | Mouse 4 | OS | 3.24 |
| | | MEAN | 4.02 |
| | | SEM | 0.18 |
| H2aM9232N | Mouse 5 | OD | 2.49 |
| | Mouse 5 | OS | 3.04 |
| | Mouse 6 | OD | 3.57 |
| | Mouse 6 | OS | 3.32 |
| | Mouse 7 | OD | 2.23 |
| | Mouse 8 | OD | 2.36 |
| | | MEAN | 2.84 |
| | | SEM | 0.23 |

As shown in FIG. 1, a single subcutaneous injection of the antagonistic anti-APLNR antibody, H2aM9232N, produced a statistically significant mean reduction of approximately 30% in retinal blood vessel outgrowth in the developing mouse retina, indicating that APLNR blockade has a significant anti-angiogenic effect at postnatal day 5.

As shown in Table 8, eyes harvested from mice injected with the antagonistic anti-APLNR antibody, H2aM9232N, demonstrated retinal blood vessel growth ranging from approximately 2.23 to 3.57 mm$^2$. In contrast, eyes harvested from mice injected with human Fc demonstrated retinal blood vessel growth ranging from approximately 3.24 to 4.95 mm$^2$.

Example 8—Potency and Efficacy of Modified Apelin Peptides in a CRE Assay

Modified Apelin-13 peptides, such as Apelin-13 peptides having one or more amino acid(s) deleted from or added to the N-terminus or C-terminus, were tested for their relative potencies with respect to APLNR activation in a bioassay that was developed to detect the activation of hAPLNR. (See also PCT International Publication No. WO2014/152955 A1, published on Sep. 25, 2014, which is hereby incorporated by reference.) Various antibody fusion proteins having Apelin-13, or modified Apelin peptides, tethered to the N-terminus or C-terminus of select anti-APLNR antibodies were also made and tested for activation as shown in Example 9 hereinbelow.

Briefly, an HEK293 cell line was transfected to stably express the full-length human hAPLNR (amino acids 1-380 of accession number NP_005152.1), along with a luciferase reporter [cAMP response element (CRE,4X)-luciferase]. The resulting cell line, HEK293/CRE-luc/hAPLNR, was maintained in DMEM containing 10% FBS, NEAA, penicillin/streptomycin, and 100 µg/mL hygromycin B. For the bioassay, HEK293/CRE-luc/hAPLNR cells were seeded onto 96-well assay plates at 20,000 cells/well in 80 µL of OPTIMEM supplemented with 0.1% FBS and penicillin/streptomycin/L-glutamine and incubated for 16 hours at 37° C. in 5% CO2. The next morning, to measure inhibition of forskolin-induced cAMP production via hAPLNR activation, unmodified apelin peptide and modified apelin peptides (see Table 9) were serially diluted (1:3) then mixed with forskolin (Sigma, #F6886) in assay buffer (5 µM final forskolin concentration), and added to the cells. After 5 hours of incubation at 37° C. in 5% CO2, luminescence was measured following the addition of One Glo reagent (Promega, #E6051) using a Victor X instrument (Perkin Elmer). The data were fit by nonlinear regression to a 4-parameter logistic equation with Prism 5 software (GraphPad).

As shown in Table 9, apelin-13 can tolerate deletions of amino acids from both the N-terminus and C-terminus while still retaining full efficacy in the CRE assay, and displaying different degrees of reduced potency compared to apelin-13. Furthermore, apelin-13 can tolerate the addition of amino acid residues to its C-terminus, such as five glycine residues (e.g. apelin-13+5G), and still retain full efficacy but with reduced potency, relative to apelin-13.

TABLE 9

Modified Apelin Peptides Tested in CRE Assay

| Apelin Peptide | Amino Acid Sequence | EC$_{50}$ (M) |
|---|---|---|
| Apelin-13 | QRPRLSHKGPMPF (SEQ ID NO: 228) | 1.403e-013 |
| Apelin-F13A | QRPRLSHKGPMPA (SEQ ID NO: 260) | 1.027e-010 |
| Apelin65-76/ Apelin-Cter12 | QRPRLSHKGPMP (SEQ ID NO: 261) | 5.713e-011 |
| Apelin65-75/ Apelin-Cter11 | QRPRLSHKGPM (SEQ ID NO: 262) | 3.604e-012 |
| Apelin-12 | RPRLSHKGPMPF (SEQ ID NO: 263) | 8.704e-013 |
| Apelin-11 | PRLSHKGPMPF (SEQ ID NO: 264) | 4.379e-010 |
| Apelin66-76 | RPRLSHKGPMP (SEQ ID NO: 265) | 5.194e-012 |
| Apelin67-76 | PRLSHKGPMP (SEQ ID NO: 266) | 1.137e-013 |
| Apelin66-75 | RPRLSHKGPM (SEQ ID NO: 267) | 2.174e-012 |
| Apelin67-75 | PRLSHKGPM (SEQ ID NO: 268) | 3.738e-007 |
| Apelin-13 + 5G | QRPRLSHKGPMPFGGGGG (SEQ ID NO: 269) | 1.469e-010 |

Example 9. Antibody-Fusion Proteins Activate APLNR

The ability of antibody-apelin fusions to activate hAPLNR-mediated cell signaling was measured using a cyclic AMP assay, similarly to the assay described hereinabove in Example 5. Apelin peptides of various lengths fused to three different anti-APLNR antibodies (H4H9092P, H4H9093P and H4H9209N) at the N- or C-terminus of the antibodies, and Apelin fused to the N-terminus of a control antibody (anti-myc), were tested for their ability to activate hAPLNR by measuring the regulation of Forskolin activation in HEK293/CRE-luc/hAPLNR cells. Several Apelin-antibody fusions demonstrated activation of hAPLNR with a level of activation similar to that of Apelin. The Apelin-antibody fusions had $EC_{50}$ values ranging from 27 pM to 29 nM with 10 μM or 7.5 μM Forskolin, as shown in Tables 10A and 10B, respectively. Apelin alone activated hAPLNR with $EC_{50}$ values of 25 pM with 10 μM Forskolin and 39 μM with 7.5 μM Forskolin. Two Apelin-antibody fusions, without any linkers, did not demonstrate any measurable activation of hAPLNR. Furthermore, apelin-cter11, as well as apelin-cter11+serine, fusions induced full activation (tested with 7.5 μM Forskolin). However, activation tended to decrease when Apelin peptide was truncated at the C-terminus to 10 amino acids, and no activation was seen when Apelin length was decreased at its C-terminus to 9 amino acids. Apelin fused to an irrelevant antibody (anti-myc antibody) demonstrated activation of 37% and 53% at 100 nM in separate experiments, indicating that Apelin fused to an irrelevant antibody activates, but weakly compared with Apelin alone or Apelin fused to anti-APLNR antibodies.

Apelin-antibody fusions were also tested for their ability to inhibit hAPLNR by measuring the regulation of Forskolin activation in HEK293/CRE-luc/hAPLNR cells. See Tables 10C and 10D. Five Apelin-antibody fusions demonstrated weak blockade of hAPLNR between 13 to 29% at the highest concentration tested. Apelin fused to the N-terminus of an irrelevant antibody (anti-myc antibody) and an isotype control did not demonstrate any measureable inhibition of hAPLNR.

TABLE 10A

Activation of hAPLNR by Antibody-Apelin fusions (10 μM Forskolin) in the HEK293/CRE-luc/hAPLNR cell line

| Antibody (-fusion) tested | Modification (Fusion) Description | Apelin Length (Sequence) | $EC_{50}$ of Apelin 2.5E−11 (10 μM Forskolin) | |
|---|---|---|---|---|
| | | | $EC_{50}$ [M] | % Activation at 100 nM mAb (10 μM Forskolin) |
| H4H9093P | No modification | No Apelin | No Activation | No Activation |
| H4H9093P-1-NVK3 | Nter Vk fusion with (G4S)3 linker | 13 | 7.7E−09 | 100% |
| H4H9093P-2-CVK3 | Cter Vk fusion with (G4S)3 linker | 13 | 9.2E−11 | 100% |
| H4H9093P-3-NVH3 | Nter VH fusion with (G4S)3 linker | 13 | 5.9E−11 | 100% |
| H4H9093P-4-NVH0 | Nter VH fusion with no linker | 13 | No Activation | No Activation |
| H4H9093P-5-NVH1 | Nter VH fusion with G4S linker | 13 | 4.6E−10 | 100% |
| H4H9093P-6-NVH2 | Nter VH fusion with (G4S)2 linker | 13 | 8.7E−11 | 100% |
| H4H9093P-APN9-(G4S)3 | Nter VH fusion with (G4S)3 linker | 9 (SEQ ID NO: 270) | Not tested | Not tested |
| H4H9093P-APN10-(G4S)3 | Nter VH fusion with (G4S)3 linker | 10 (SEQ ID NO: 271) | Not tested | Not tested |
| H4H9093P-APN11-(G4S)3 | Nter VH fusion with (G4S)3 linker | 11 (SEQ ID NO: 262) | Not tested | Not tested |
| H4H9093P-APN11 + S - (G4S)3 | Nter VH fusion with (G4S)3 linker | 11 + S (SEQ ID NO: 272) | Not tested | Not tested |
| H4H9093P-APNV5-11-(G4S)3 | Nter VH fusion with (G4S)3 linker | V5-11 (SEQ ID NO: 273) | Not tested | Not tested |
| H4H9092P | No modification | No Apelin | No Activation | No Activation |
| H4H9092P-1-NVH3 | Nter VH fusion with (G4S)3 linker | 13 | 7.3E−11 | 100% |
| H4H9092P-2-NVK3 | Nter Vk fusion with (G4S)3 linker | 13 | 2.9E−08 | 100% |
| H4H9092P-3-CVK3 | Cter Vk fusion with (G4S)3 linker | 13 | 7.5E−10 | 100% |
| H4H9209N | No modification | No Apelin | No Activation | No Activation |
| H4H9209N-1-NVH0 | Nter VH fusion with no linker | 13 | No Activation | No Activation |
| H4H9209N-2-NVH1 | Nter VH fusion with G4S linker | 13 | 2.9E−09 | 100% |
| H4H9209N-3-NVH2 | Nter VH fusion with (G4S)2 linker | 13 | 6.5E−11 | 100% |
| H4H9209N-4-NVH3 | Nter VH fusion with (G4S)3 linker | 13 | 2.8E−11 | 100% |

TABLE 10A-continued

Activation of hAPLNR by Antibody-Apelin fusions (10 μM Forskolin) in the HEK293/CRE-luc/hAPLNR cell line

| Antibody (-fusion) tested | Modification (Fusion) Description | Apelin Length (Sequence) | EC$_{50}$ of Apelin EC$_{50}$ [M] | 2.5E−11 (10 μM Forskolin) % Activation at 100 nM mAb (10 μM Forskolin) |
|---|---|---|---|---|
| H4H9209N-APN9-(G4S)3 | Nter VH fusion with (G4S)3 linker | 9 (SEQ ID NO: 270) | Not tested | Not tested |
| H4H9209N-APN10-(G4S)3 | Nter VH fusion with (G4S)3 linker | 10 (SEQ ID NO: 271) | Not tested | Not tested |
| H4H9209N-APN11-(G4S)3 | Nter VH fusion with (G4S)3 linker | 11 (SEQ ID NO: 262) | Not tested | Not tested |
| H4H9209N-APN11 + S-(G4S)3 | Nter VH fusion with (G4S)3 linker | 11 + S (SEQ ID NO: 272) | Not tested | Not tested |
| Anti-myc 9E10 | Nter VH fusion with (G4S)3 linker | 13 | >1.0E−07 | 37% |
| Isotype control 3 | No modification | No Apelin | No Activation | No Activation |

TABLE 10B

Activation of hAPLNR by Antibody-Apelin fusions (7.5 μM Forskolin) in the HEK293/CRE-luc/hAPLNR cell line

| Antibody (-fusion) tested | Modification (Fusion) Description | Apelin Length (Sequence) | EC$_{50}$ of Apelin EC$_{50}$ [M] | 3.9E−11 (7.5 μM Forskolin) % Activation at 100 nM mAb (7.5 μM Forskolin) |
|---|---|---|---|---|
| H4H9093P | No modification | No Apelin | No Activation | No Activation |
| H4H9093P-1-NVK3 | Nter Vk fusion with (G4S)3 linker | 13 | Not tested | Not tested |
| H4H9093P-2-CVK3 | Cter Vk fusion with (G4S)3 linker | 13 | Not tested | Not tested |
| H4H9093P-3-NVH3 | Nter VH fusion with (G4S)3 linker | 13 | 8.7E−11 | 100% |
| H4H9093P-4-NVH0 | Nter VH fusion with no linker | 13 | Not tested | Not tested |
| H4H9093P-5-NVH1 | Nter VH fusion with G4S linker | 13 | Not tested | Not tested |
| H4H9093P-6-NVH2 | Nter VH fusion with (G4S)2 linker | 13 | Not tested | Not tested |
| H4H9093P-APN9-(G4S)3 | Nter VH fusion with (G4S)3 linker | 9 (SEQ ID NO: 270) | No Activation | No Activation |
| H4H9093P-APN10-(G4S)3 | Nter VH fusion with (G4S)3 linker | 10 (SEQ ID NO: 271) | 1.4E−09 | 50% |
| H4H9093P-APN11-(G4S)3 | Nter VH fusion with (G4S)3 linker | 11 (SEQ ID NO: 262) | 1.6E−10 | 100% |
| H4H9093P-APN11 + S-(G4S)3 | Nter VH fusion with (G4S)3 linker | 11 + S (SEQ ID NO: 272) | 9.2E−11 | 100% |
| H4H9093P-APNV5-11-(G4S)3 | Nter VH fusion with (G4S)3 linker | V5-11 (SEQ ID NO: 273) | 5.8E−09 | 100% |
| H4H9092P | No modification | No Apelin | Not tested | Not tested |
| H4H9092P-1-NVH3 | Nter VH fusion with (G4S)3 linker | 13 | Not tested | Not tested |
| H4H9092P-2-NVK3 | Nter Vk fusion with (G4S)3 linker | 13 | Not tested | Not tested |
| H4H9092P-3-CVK3 | Cter Vk fusion with (G4S)3 linker | 13 | Not tested | Not tested |
| H4H9209N | No modification | No Apelin | No Activation | No Activation |

TABLE 10B-continued

Activation of hAPLNR by Antibody-Apelin fusions (7.5 μM Forskolin) in the HEK293/CRE-luc/hAPLNR cell line

| | | | EC$_{50}$ of Apelin | 3.9E−11 (7.5 μM Forskolin) |
|---|---|---|---|---|
| Antibody (-fusion) tested | Modification (Fusion) Description | Apelin Length (Sequence) | EC$_{50}$ [M] | % Activation at 100 nM mAb (7.5 μM Forskolin) |
| H4H9209N-1-NVH0 | Nter VH fusion with no linker | 13 | Not tested | Not tested |
| H4H9209N-2-NVH1 | Nter VH fusion with G4S linker | 13 | Not tested | Not tested |
| H4H9209N-3-NVH2 | Nter VH fusion with (G4S)2 linker | 13 | Not tested | Not tested |
| H4H9209N-4-NVH3 | Nter VH fusion with (G4S)3 linker | 13 | 2.4E−11 | 100% |
| H4H9209N-APN9-(G4S)3 | Nter VH fusion with (G4S)3 linker | 9 (SEQ ID NO: 270) | No Activation | No Activation |
| H4H9209N-APN10-(G4S)3 | Nter VH fusion with (G4S)3 linker | 10 (SEQ ID NO: 271) | 1.2E−09 | 38% |
| H4H9209N-APN11-(G4S)3 | Nter VH fusion with (G4S)3 linker | 11 (SEQ ID NO: 262) | 2.7E−11 | 100% |
| H4H9209N-APN11 + S-(G4S)3 | Nter VH fusion with (G4S)3 linker | 11 + S (SEQ ID NO: 272) | 1.1E−10 | 100% |
| Anti-myc 9E10 | (G4S)3 linker | 13 | 1.1E−08 | 53% |
| Isotype control 3 | No modification | No Apelin | No Activation | No Activation |

TABLE 10C

Inhibition of hAPLNR by Antibody-Apelin fusions (10 μM Forskolin) in the HEK293/CRE-luc/hAPLNR cell line

| | | | EC$_{50}$ of Apelin | 2.5E−11 (10 μM Forskolin) |
|---|---|---|---|---|
| Antibody (-fusion) tested | Modification (Fusion) Description | Apelin Length (Sequence) | IC$_{50}$ [M] | % Inhibition at 100 nM mAb, in the presence of 100 pM Apelin (at 10 μM Forskolin) |
| H4H9093P | No modification | No Apelin | IC | 16% |
| H4H9093P-1-NVK3 | Nter Vk fusion with (G4S)3 linker | 13 | No Inhibition | No Inhibition |
| H4H9093P-2-CVK3 | Cter Vk fusion with (G4S)3 linker | 13 | No Inhibition | No Inhibition |
| H4H9093P-3-NVH3 | Nter VH fusion with (G4S)3 linker | 13 | No Inhibition | No Inhibition |
| H4H9093P-4-NVH0 | Nter VH fusion with no linker | 13 | IC | 29% |
| H4H9093P-5-NVH1 | Nter VH fusion with G4S linker | 13 | No Inhibition | No Inhibition |
| H4H9093P-6-NVH2 | Nter VH fusion with (G4S)2 linker | 13 | No Inhibition | No Inhibition |
| H4H9093P-APN9-(G4S)3 | Nter VH fusion with (G4S)3 linker | 9 (SEQ ID NO: 270) | Not tested | Not tested |
| H4H9093P-APN10-(G4S)3 | Nter VH fusion with (G4S)3 linker | 10 (SEQ ID NO: 271) | Not tested | Not tested |
| H4H9093P-APN11-(G4S)3 | Nter VH fusion with (G4S)3 linker | 11 (SEQ ID NO: 262) | Not tested | Not tested |
| H4H9093P-APN11 + S-(G4S)3 | Nter VH fusion with (G4S)3 linker | 11 + S (SEQ ID NO: 272) | Not tested | Not tested |
| H4H9093P-APNV5-11-(G4S)3 | Nter VH fusion with (G4S)3 linker | V5-11 (SEQ ID NO: 273) | Not tested | Not tested |

TABLE 10C-continued

Inhibition of hAPLNR by Antibody-Apelin fusions (10 μM Forskolin) in the HEK293/CRE-luc/hAPLNR cell line

| Antibody (-fusion) tested | Modification (Fusion) Description | Apelin Length (Sequence) | EC$_{50}$ of Apelin IC$_{50}$ [M] | 2.5E−11 (10 μM Forskolin) % Inhibition at 100 nM mAb, in the presence of 100 pM Apelin (at 10 μM Forskolin) |
|---|---|---|---|---|
| H4H9092P | No modification | No Apelin | IC | 5% |
| H4H9092P-1-NVH3 | Nter VH fusion with (G4S)3 linker | 13 | No Inhibition | No Inhibition |
| H4H9092P-2-NVK3 | Nter Vk fusion with (G4S)3 linker | 13 | No Inhibition | No Inhibition |
| H4H9092P-3-CVK3 | Cter Vk fusion with (G4S)3 linker | 13 | No Inhibition | No Inhibition |
| H4H9209N | No modification | No Apelin | 5.9E−09 | 16% |
| H4H9209N-1-NVH0 | Nter VH fusion with no linker | 13 | IC | 13% |
| H4H9209N-2-NVH1 | Nter VH fusion with G4S linker | 13 | No Inhibition | No Inhibition |
| H4H9209N-3-NVH2 | Nter VH fusion with (G4S)2 linker | 13 | No Inhibition | No Inhibition |
| H4H9209N-4-NVH3 | Nter VH fusion with (G4S)3 linker | 13 | No Inhibition | No Inhibition |
| H4H9209N-APN9-(G4S)3 | Nter VH fusion with (G4S)3 linker | 9 (SEQ ID NO: 270) | Not tested | Not tested |
| H4H9209N - APN10-(G4S)3 | Nter VH fusion with (G4S)3 linker | 10 (SEQ ID NO: 271) | Not tested | Not tested |
| H4H9209N - APN11-(G4S)3 | Nter VH fusion with (G4S)3 linker | 11 (SEQ ID NO: 262) | Not tested | Not tested |
| H4H9209N - APN11 + S - (G4S)3 | Nter VH fusion with (G4S)3 linker | 11 + S (SEQ ID NO: 272) | Not tested | Not tested |
| Anti-myc 9E10 | Nter VH fusion with (G4S)3 linker | 13 | No Inhibition | No Inhibition |
| Isotype control 3 | No modification | No Apelin | No Inhibition | No Inhibition |

IC = IC$_{50}$ value could not be determined

TABLE 10D

Inhibition of hAPLNR by Antibody-Apelin fusions (7.5 uM Forskolin) in the HEK293/CRE-luc/hAPLNR cell line

| Antibody (-fusion) tested | Modification (Fusion) Description | Apelin Length (Sequence) | EC$_{50}$ of Apelin IC$_{50}$ [M] | 3.9E−11 (7.5 μM Forskolin) % Inhibition at 100 nM mAb, in the presence of 100 pM Apelin (at 7.5 μM Forskolin) |
|---|---|---|---|---|
| H4H9093P | No modification | No Apelin | IC | 3% |
| H4H9093P-1-NVK3 | Nter Vk fusion with (G4S)3 linker | 13 | Not tested | Not tested |
| H4H9093P-2-CVK3 | Cter Vk fusion with (G4S)3 linker | 13 | Not tested | Not tested |
| H4H9093P-3-NVH3 | Nter VH fusion with (G4S)3 linker | 13 | No inhibition | No inhibition |
| H4H9093P-4-NVH0 | Nter VH fusion with no linker | 13 | Not tested | Not tested |
| H4H9093P-5-NVH1 | Nter VH fusion with G4S linker | 13 | Not tested | Not tested |
| H4H9093P-6-NVH2 | Nter VH fusion with (G4S)2 linker | 13 | Not tested | Not tested |
| H4H9093P-APN9-(G4S)3 | Nter VH fusion with (G4S)3 linker | 9 (SEQ ID NO: 270) | 1.3E−08 | 27% |

TABLE 10D-continued

Inhibition of hAPLNR by Antibody-Apelin fusions (7.5 uM Forskolin) in the HEK293/CRE-luc/hAPLNR cell line

|  |  |  | 3.9E−11 (7.5 µM Forskolin) | |
|---|---|---|---|---|
|  | EC$_{50}$ of Apelin | | | % Inhibition at 100 nM mAb, in |
| Antibody (-fusion) tested | Modification (Fusion) Description | Apelin Length (Sequence) | IC$_{50}$ [M] | the presence of 100 pM Apelin (at 7.5 µM Forskolin) |
| H4H9093P-APN10-(G4S)3 | Nter VH fusion with (G4S)3 linker | 10 (SEQ ID NO: 271) | 3.2E−08 | 15% |
| H4H9093P-APN11-(G4S)3 | Nter VH fusion with (G4S)3 linker | 11 (SEQ ID NO: 262) | No inhibition | No inhibition |
| H4H9093P-APN11 + S - (G4S)3 | Nter VH fusion with (G4S)3 linker | 11 + S (SEQ ID NO: 272) | No inhibition | No inhibition |
| H4H9093P-APNV5-11-(G4S)3 | Nter VH fusion with (G4S)3 linker | V5-11 (SEQ ID NO: 273) | No inhibition | No inhibition |
| H4H9092P | No modification | No Apelin | Not tested | Not tested |
| H4H9092P-1-NVH3 | Nter VH fusion with (G4S)3 linker | 13 | Not tested | Not tested |
| H4H9092P-2-NVK3 | Nter Vk fusion with (G4S)3 linker | 13 | Not tested | Not tested |
| H4H9092P-3-CVK3 | Cter Vk fusion with (G4S)3 linker | 13 | Not tested | Not tested |
| H4H9209N | No modification | No Apelin | No inhibition | No inhibition |
| H4H9209N-1-NVH0 | Nter VH fusion with no linker | 13 | Not tested | Not tested |
| H4H9209N-2-NVH1 | Nter VH fusion with G4S linker | 13 | Not tested | Not tested |
| H4H9209N-3-NVH2 | Nter VH fusion with (G4S)2 linker | 13 | Not tested | Not tested |
| H4H9209N-4-NVH3 | Nter VH fusion with (G4S)3 linker | 13 | No Inhibition | No Inhibition |
| H4H9209N-APN9-(G4S)3 | Nter VH fusion with (G4S)3 linker | 9 (SEQ ID NO: 270) | 9.3E−09 | 14% |
| H4H9209N - APN10-(G4S)3 | Nter VH fusion with (G4S)3 linker | 10 (SEQ ID NO: 271) | No Inhibition | No Inhibition |
| H4H9209N - APN11-(G4S)3 | Nter VH fusion with (G4S)3 linker | 11 (SEQ ID NO: 262) | No inhibition | No inhibition |
| H4H9209N - APN11 + S - (G4S)3 | Nter VH fusion with (G4S)3 linker | 11 + S (SEQ ID NO: 272) | No inhibition | No inhibition |
| Anti-myc 9E10 | Nter VH fusion with (G4S)3 linker | 13 | No inhibition | No inhibition |
| Isotype control 3 | No modification | No Apelin | No Inhibition | No Inhibition |

Example 10: Activation of APLNR-Mediated Receptor Signaling by Antibody-Fusion Proteins in the pERK Assay Experiments were done as essentially shown in Example 6, described hereinabove. As shown in Table 11, two (2) antibody-Apelin fusions of the invention increased the ratio of pERK1/2 to total ERK1/2 with EC50 values of 542.2 pM and 271.4 pM, while Apelin-13 increased the ratio of pERK1/2 to total ERK1/2 with an EC50 value of 32.48 pM.

TABLE 11

Activity of antibody-Apelin fusions and Apelin-13 peptide in pERK/total ERK assays

| Sample tested | Activating EC$_{50}$ (M) |
|---|---|
| H4H9093P Nter VH fusion with (G4S)3 linker (H4H9093P-3-NVH3) | 5.422E−10 |
| H4H9209N Nter VH fusion with (G4S)3 linker (H4H9209N-4-NVH3) | 2.714E−10 |
| Apelin-13 (no fusion) | 3.248E−11 |

Example 11: Activation of APLNR-Mediated Receptor Signaling by Antibody-Fusion Proteins in a β-Arrestin Assay A PathHunter® eXpress AGTRL1 CHO-K1 β-Arrestin GPCR cell based assay (DiscoverX, #93-0250E2) was used to assess signaling through recruitment of β-Arrestin by the activated human Apelin receptor (hAPLNR). To test the β-arrestin recruitment upon hAPLNR activation, PathHunter® eXpress AGTRL1 CHO-K1 β-Arrestin cells were seeded onto 96-well assay plates at 8500 cells/well according to the manufacturer's protocol and incubated at 37° C. in 5% $CO_2$ for two nights. On the day of the assay, Apelin, pyroglutamyl Apelin-13, (Bachem, #H-4568) was serially diluted (1:3) from 500 nM to 0.08 nM (including a control sample containing no Apelin) and added to the cells.

To measure the ability of Apelin-antibody fusions and antibodies to activate hAPLNR, Apelin-antibody fusions and antibodies were serially diluted (1:3) from 500 nM to 0.08 nM and added to the cells without exogenous Apelin. Testing of Apelin-antibody fusions and antibodies included a no antibody control. After 1.5 hours of incubation at 37° C. in 5% $CO_2$, chemiluminescent activity was detected on a Victor X instrument (Perkin Elmer) after an addition of PathHunter® Detection Reagents.

The results of all assays were analyzed using nonlinear regression (4-parameter logistics) within Prism 5 software (GraphPad). Activation by the antibodies and Apelin-antibody fusions was calculated as a percentage of the maximum activation seen in the Apelin dose response. In the PathHunter® eXpress AGTRL1 CHO-K1 β-Arrestin cell based assay, all 11 of the anti-APLNR antibodies fused to Apelin peptides tested demonstrated partial activation of hAPLNR with activation ranging from 2-64% of maximum Apelin activation, and corresponding $EC_{50}$ values ranging from 970 pM to >100 nM. Anti-APLNR antibodies without Apelin fusion showed little to no activation. Apelin activated hAPLNR with an $EC_{50}$ value of 1.5 nM. Apelin fused to an irrelevant anti-myc antibody demonstrated weak activation of hAPLNR at 6% at the highest concentration tested 500 nM, without a measurable $EC_{50}$, while an isotype control antibody did not demonstrate any measurable activation in this assay.

TABLE 12

Activation of hAPLNR by Antibody-Apelin fusions and antibodies in PathHunter ® eXpress AGTRL1 CHO-K1 β-Arrestin cell based assay

| | | | Cell Line Tested:<br>$EC_{50}$ of Apelin (M): | PathHunter ® eXpress AGTRL1 CHO-K1<br>β-Arrestin Cells<br>1.5E−09 |
|---|---|---|---|---|
| Antibody-Apelin fusion description | | | | |
| Antibody<br>(-fusion)<br>tested | Modification<br>(Fusion)<br>Description | Apelin<br>Length<br>(Sequence) | $EC_{50}$ [M] | % Activation at 500 nM<br>antibody or Apelin-<br>antibody fusion |
| H4H9093P | No modification | No Apelin | IC | 2% |
| H4H9093P-3-NVH3 | Nter VH fusion with (G4S)3 linker | 13 | 2.1E−09 | 54% |
| H4H9093P-APN9-(G4S)3 | Nter VH fusion with (G4S)3 linker | 9 (SEQ ID NO: 270) | 8.3E−09 | 4% |
| H4H9093P-APN10-(G4S)3 | Nter VH fusion with (G4S)3 linker | 10 (SEQ ID NO: 271) | 6.5E−09 | 5% |
| H4H9093P-APN11-(G4S)3 | Nter VH fusion with (G4S)3 linker | 11 (SEQ ID NO: 262) | 5.8E−09 | 64% |
| H4H9093P-APN11 + S-(G4S)3 | Nter VH fusion with (G4S)3 linker | 11 + S (SEQ ID NO: 272) | 2.7E−09 | 37% |
| H4H9093P-APNV5-11-(G4S)3 | Nter VH fusion with (G4S)3 linker | V5-11 (SEQ ID NO: 273) | >1E−07 | 47% |
| H4H9209N | No modification | No Apelin | No Activation | No Activation |
| H4H9209N-4-NVH3 | Nter VH fusion with (G4S)3 linker | 13 | 1.5E−09 | 30% |
| H4H9209N-APN9-(G4S)3 | Nter VH fusion with (G4S)3 linker | 9 (SEQ ID NO: 270) | 3.5E−09 | 3% |
| H4H9209N-APN10-(G4S)3 | Nter VH fusion with (G4S)3 linker | 10 (SEQ ID NO: 271) | 4.0E−09 | 2% |
| H4H9209N-APN11-(G4S)3 | Nter VH fusion with (G4S)3 linker | 11 (SEQ ID NO: 262) | 9.7E−10 | 44% |
| H4H9209N-APN11 + S-(G4S)3 | Nter VH fusion with (G4S)3 linker | 11 + S (SEQ ID NO: 272) | 3.1E−09 | 25% |

TABLE 12-continued

Activation of hAPLNR by Antibody-Apelin fusions and antibodies in PathHunter ® eXpress AGTRL1 CHO-K1 β-Arrestin cell based assay

| Anti-myc 9E10 | Nter VH fusion with (G4S)3 linker | 13 | IC | 6% |
| Isotype control antibody | | | No Activation | No Activation |

IC = $EC_{50}$ value could not be determined

Example 12—Antibody-Apelin-11 Fusions Show Increased Stability in Serum

To measure the stability and activity of the apelin peptide fusion antibody in serum, fusion antibodies were exposed to mouse serum for different times (0, 6, 24 hours). After antibody purification from serum, samples were analyzed by mass spectrometry, to evaluate the presence of apelin fragments. To test activity of the exposed Apelin-antibody fusions, the diluted serum with unpurified antibody fusion was also tested in a beta-arrestin activity assay. Serum obtained from a male C57bl/6 mouse was diluted with PBS at a 1 to 1 ratio. A total of 100 µg apelin-antibody fusion was added to serum. 250 µl or 25% of this mixture was removed immediately and placed at −20° C. (t=0 timepoint). The remaining mixture was placed in an incubator at 37° C. and 250 µl of the mixture was removed after 6 and 24 hours.

Sample purification via protein A beads: Dynabead™ Protein A beads (Invitrogen Cat #10001D) were washed 3 times with PBS. 25 µl Dynabead™ slurry was added to 225 µl of serum and apelin-antibody fusion mixture. The new mixture was incubated at 4° C. with rotation for 3 hours to allow the antibody fusion binding to the protein A beads. After incubation, beads were washed 3 times with PBS. Sixty µl of Laemilli dye/buffer was added to the washed and pelleted protein A beads. This mixture was incubated at 90° C. for 5 minutes, to dissociate the purified antibody from the protein A beads.

Mass Spectrometry Preparation: Five (5) µl of beta-mercaptoethanol was added to the purified antibody and denatured at 95° C. for 10 min. The entire volume of the purified antibody was loaded onto a Tris-glycine gel and ran at 150V for 1 hr. Coomaise blue was used to stain the gel. The 50 kDa band, corresponding to the heavy chain fragment, was cut out from the gel and chopped finely. The excised bands were split into two 500 µl tubes. 100 µl of 100 mM ammonium bicarbonate/50% acetonitrile was added and incubated at 37° C. for 1 hr to destain the gels. Destaining solution is removed and 100 µl of 100% acetonitrile is added to dehydrate the gel for 5 minutes at ambient temperature. Dehydration solution is removed from the gel and 75 µl of 10 mM DTT in 50 mM ammonium bicarbonate is added and incubated at 37° C. for 30 minutes to reduce the protein. Reducing solution is removed and 75 µl of 55 mM Iodoacetamide in 50 mM ammonium bicarbonate is added and incubated at ambient temperature in the dark to alkylate the protein. Alkylation solution is removed and 100 µl of 50 mM ammonium bicarbonate is added to wash the gel. Wash solution is removed and 100 µl of 100% acetonitrile is added to dehydrate the gel for 5 minutes at ambient temperature. Dehydration solution is removed and 30 µl of LYS-C enzyme mixture is added and digested overnight at 37° C. After overnight digestion samples are purified with a ZipTip filter in a 10 mg/ml alpha-cyano-4-hyrdoxycinnamic acid/70% acetonitrile/0.1% TFA solution and spot eluted onto a MALDI target and read on mass spectrometer.

Mass Spectrometry Analysis: The apelin peptide is fused to the N-terminal portion of the APLN-R antibody. The Lys-C recognizes and digests proteins at the C-terminal side of the amino acid lysine. The peptide of interest, after Lys-C digestion of the fusion antibody, has the sequence of QRPRLSHK (amino acid residue numbers 1 to 8 of SEQ ID NO: 228), reporting a mass charge ratio peak at 1004.

TABLE 13

Serum stability test at 0, 6, and 24 hours to identify intact fusion by mass spectrometry measurement (peptide fragment peak at 1004)

| Fusion Tested | Modification (Fusion) Description | 0 Hour Stability | 6 Hour Stability | 24 Hour Stability |
| --- | --- | --- | --- | --- |
| H4H9093P-3-NVH3 | Nter APN13 with (G4S)3 linker | YES | NO | NO |
| H4H9209N - APN11 + S-(G4S)3 | Nter APN-Cter11 + S with (G4S)3 linker | YES | YES (Weak) | NO |
| H4H9209N - APN11-(G4S)3 | Nter APN-Cter11 with (G4S)3 linker | YES | YES | YES |
| H4H9209N - APN10-(G4S)3 | Nter APN-Cter10 with (G4S)3 linker | YES | YES (Weak) | NO |
| H4H9209N-APN9-(G4S)3 | Nter APN-Cter9 with (G4S)3 linker | YES | YES | YES (weak) |

Figure 2A:
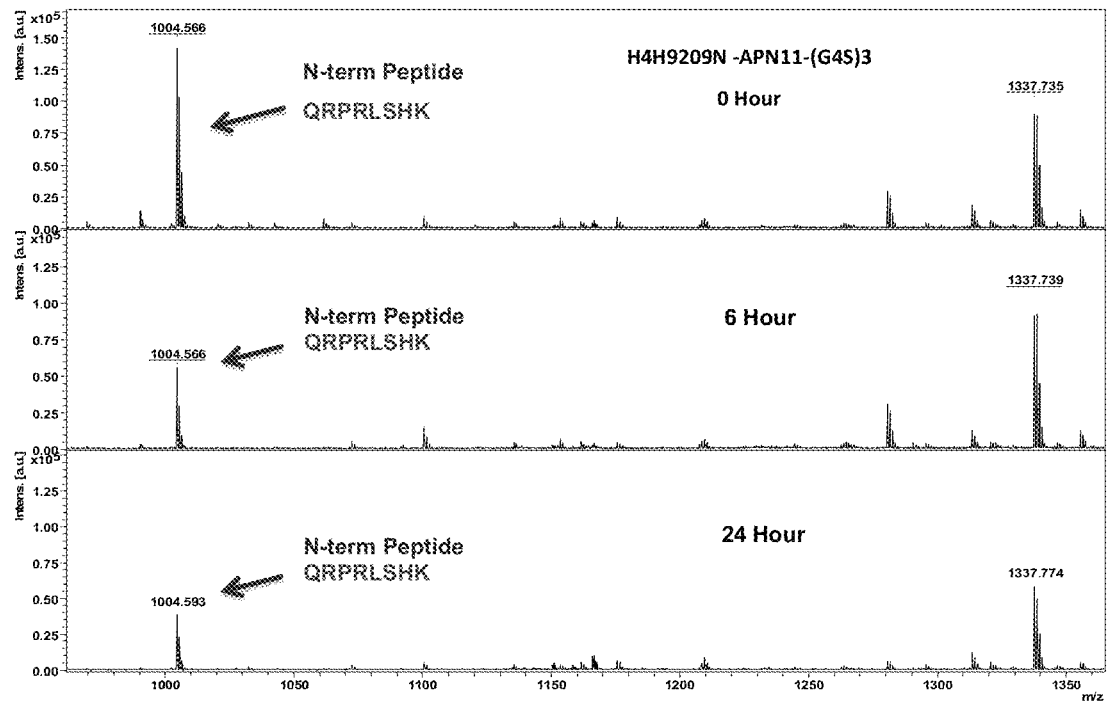
FIGS. 2A and 2B depict the pattern of intact apelin peptide peaks on mass spectrometry after 0, 6 and 24 hours of exposure to serum for truncated apelin fusion antibodies, H4H9209N-APN11-(G4S)3 (FIG. 2A) or H4H9209N-APN11+S-(G4S)3 (FIG. 2B). The peptide of interest, after Lys-C digestion of the fusion antibody after serum exposure, has the sequence of QRPRLSHK, reporting a mass charge ratio peak at 1004. The apelin-cter11 fusion antibody has residual apelin peak after 24 hours of serum exposure.
Figure 2B:
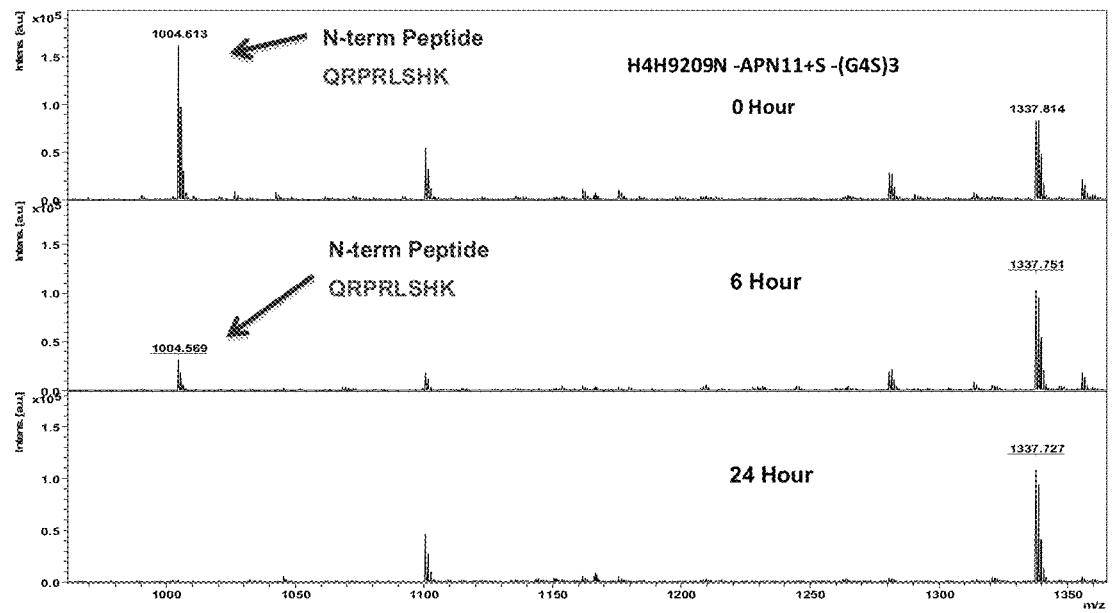

As shown in Table 13, the truncated apelin fusion antibodies report intact apelin peptide peaks on mass spectrometry after 6 hours of serum exposure. The apelin-cter11 fusion antibody has residual apelin peak after 24 hours of serum exposure. See also FIG. 2.

To test activity of the exposed Apelin-antibody fusions, the diluted serum with unpurified antibody fusion (H4H9093P-3-NVH3, H4H9209N-APN11-(G4S)3, or H4H9209N-APN11+S-(G4S)3) was tested in a beta-arrestin activity assay, as described above in Example 11 (protocol based on the DiscoverX B-Arrestin activity assay kit). The treatment concentration of each unpurified Apelin-antibody fusion was 1 µg/mL.

Figure 3:
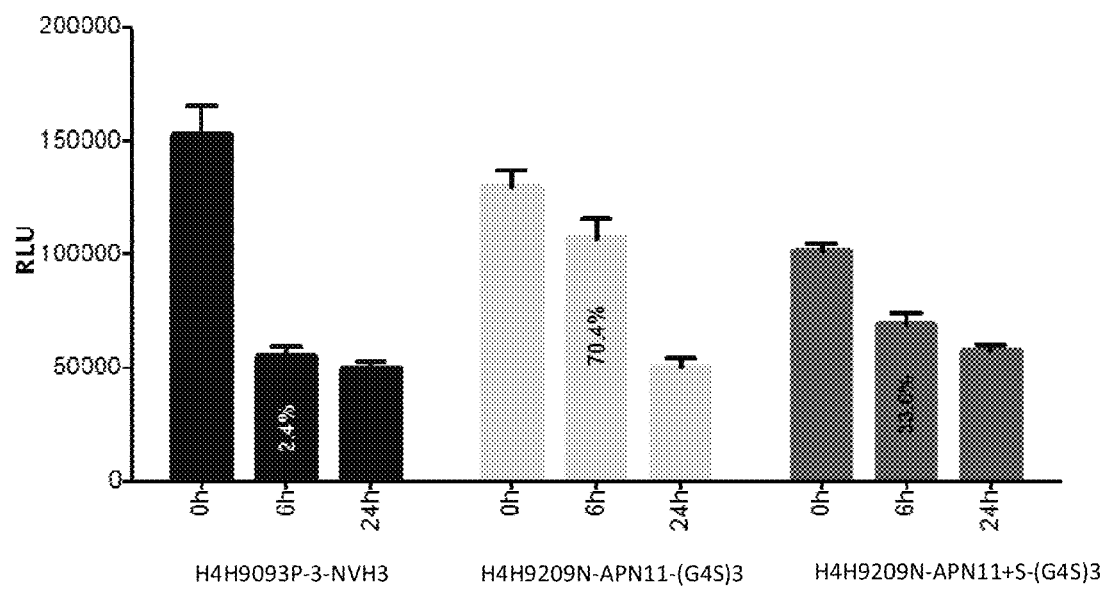
FIG. 3 shows activity of the Apelin-antibody fusions (H4H9093P-3-NVH3, H4H9209N-APN11-(G4S)3, or H4H9209N-APN11+S-(G4S)3) exposed to diluted serum in a beta-arrestin activity assay (DiscoverX β-Arrestin activity assay) at timepoints 0, 6 and 24 hours. Antibody fusions having Apelin-Cter11 and apelin-Cter11+S at their C-termini retain β-Arrestin activity after 6h of serum exposure. The 6h timepoint value represents percent activation relative to the 0 h timepoint, or 2.4%, 70.4% and 33.6% for H4H9093P-3-NVH3, H4H9209N-APN11-(G4S)3, or H4H9209N-APN11+S-(G4S)3, respectively.

Antibody fusions having Apelin-Cter11 and Apelin-Cter11+S at their C-termini retain β-Arrestin activity even after 6h of serum exposure. The results of β-Arrestin activity at timepoints 0, 6 and 24 hours are depicted in FIG. 3. The 6h timepoint value represents percent activation relative to the 0 h timepoint, or 2.4%, 70.4% and 33.6% for H4H9093P-3-NVH3, H4H9209N-APN11-(G4S)3, or H4H9209N-APN11+S-(G4S)3, respectively.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for (A) inducing vasodilation and/or angiogenesis in a subject, (B) treating an ischemic-reperfusion injury in a subject, or (C) improving cardiac function in a subject, the method comprising administering, to the subject, a protein comprising (i) an immunoglobulin (Ig) molecule or antigen-binding fragment thereof and (ii) an apelin peptide, wherein the Ig molecule comprises a heavy chain variable region (HCVR), and a light chain variable region (LCVR), wherein:

(a) the HCVR and LCVR together comprise six complementarity determining regions HCDR1-HCDR2-HCDR3-LCDR1-LCDR2-LCDR3 contained within an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 287/295, 303/311, 319/327, 335/343, 351/359 and 367/375; and (b) the apelin peptide:

(i) comprises an amino acid sequence selected from the group consisting of: SEQ ID NO: 227, SEQ ID NO: 228, SEQ ID NO: 229, SEQ ID NO: 230, SEQ ID NO: 262, SEQ ID NO: 269, SEQ ID NO: 270, SEQ ID NO: 271, SEQ ID NO: 272, SEQ ID NO: 273, SEQ ID NO: 283, SEQ ID NO: 284, and SEQ ID NO: 285; or (ii) is selected from the group consisting of amino acid residues 6-77, 40-77, 42-77, 43-77, 47-77, 59-77, 61-77, 63-77, 64-77, 65-77, 66-77, 67-77, 73-77, 1-25, 6-25, 42-64, 61-64, 61-74, 61-75, 61-76, 65-76, 65-75, 42-58, 42-57, 42-56, 42-55, 42-54, 42-53, and pyroglutamylated apelin65-77 of the preproapelin polypeptide of SEQ ID NO: 227; or (iii) is selected from the group consisting of: apelin40-77 (apelin-38), apelin42-77 (apelin-36), apelin43-77 (apelin-35), apelin47-77 (apelin-31), apelin59-77 (apelin-19), apelin61-77 (apelin-17), apelin63-77 (apelin-15), apelin64-77 (apelin-14), apelin65-77 (apelin-13), apelin66-77 (apelin-12, or Al2), apelin67-77 (apelin-11), apelin68-77 (apelin-10), apelin73-77 (apelin-5), apelin61-76 (apelin-K16P), apelin61-75 (apelin-K15M), apelin61-74 (apelin-K14P), and [Pyr1]Apelin-13.

2. The method of claim 1, for inducing vasodilation and/or angiogenesis in the subject.

3. The method of claim 1, for treating an ischemic-reperfusion injury in the subject.

4. The method of claim 1, for improving cardiac function in the subject.

5. The method of claim 4, wherein the subject suffers from a condition selected from congestive heart failure, myocardial infarction, or cardiomyopathy.

6. The method of claim 1, wherein the apelin peptide is fused to the Ig molecule at the N or the C terminus of the Ig molecule.

7. The method of claim 1, wherein the apelin peptide is fused to the Ig molecule at the N terminus or the C terminus of the HCVR.

8. The method of claim 1, wherein the apelin peptide is fused to the Ig molecule at the N terminus or the C terminus of the LCVR.

9. The method of claim 1, wherein the CDRs of the HCVR/LCVR amino acid sequence pair are contiguous.

10. The method of claim 1, wherein the protein:
activates apelin receptor (APLNR)-mediated inhibition of cAMP accumulation;
decreases apelin receptor (APLNR)-mediated inhibition of cAMP with an EC50 of less than about 100 nM as measured in an in vitro cAMP accumulation assay;
decreases apelin receptor (APLNR)-mediated inhibition of cAMP with an EC50 of less than about 10 nM as measured in an in vitro cAMP accumulation assay;
activates apelin receptor (APLNR)-mediated pERK in an in vitro pERK assay;
increases apelin receptor (APLNR)-mediated pERK to total ERK ratio with an EC50 of less than about 10 nM as measured in an in vitro pERK assay; or
increases apelin receptor (APLNR)-mediated pERK to total ERK ratio with an EC50 of less than about 1 nM as measured in an in vitro pERK assay.

11. The method of claim 1, wherein the protein comprises an amino acid sequence pair selected from the group consisting of: SEQ ID NOs: 130/235, 130/237, 239/138, 241/138, 243/138, 245/138, 247/122, 114/249, 114/251, 253/26, 255/26, 257/26, 259/26, 274/138, 275/138, 276/138, 277/138, 278/138, 279/26, 280/26, 281/26, and 282/26.

12. The method of claim 1, wherein the Ig molecule comprises a scFv comprising a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 287/295, 303/311, 319/327, 335/343, 351/359 and 367/375.

13. The method of claim 12, wherein the Ig molecule comprises a scFv comprising a HCVR/LCVR amino acid sequence pair selected from the group consisting of SEQ ID NOs: 34/42, 50/58, 66/74, 82/90, 287/295, 303/311, 319/327, 335/343, 351/359 and 367/375.

14. The method of claim 1, wherein the six complementarity determining regions HCDR1-HCDR2-HCDR3-LCDR1-LCDR2-LCDR3 comprise the amino acid sequences, respectively, selected from the group consisting of SEQ ID NOs: 4-6-8-12-14-16, 20-22-24-28-30-32, 36-38-40-44-46-48, 52-54-56-60-62-64, 68-70-72-76-78-80, 84-86-88-92-94-96, 100-102-104-108-110-112, 116-118-120-124-126-128, 132-134-136-140-142-144, 148-150-152-156-158-160, 164-166-168-172-174-176, 180-182-184-188-190-192, 196-198-200-204-206-208, 212-214-216-220-222-224, 289-291-293-297-299-301, 305-307-309-313-315-317, 321-323-325-329-331-333, 337-339-341-345-347-349, 353-355-357-361-363-365, and 369-371-373-377-379-381.

15. The method of claim 14, wherein the six complementarity determining regions HCDR1-HCDR2-HCDR3-LCDR1-LCDR2-LCDR3 comprise the amino acid sequences, respectively, selected from the group consisting of SEQ ID NOs: 36-38-40-44-46-48, 52-54-56-60-62-64, 68-70-72-76-78-80, 84-86-88-92-94-96, 289-291-293-297-299-301, 305-307-309-313-315-317, 321-323-325-329-331-333, 337-339-341-345-347-349, 353-355-357-361-363-365, and 369-371-373-377-379-381.

16. The method of claim 1, wherein the apelin peptide is fused to the Ig molecule or antigen-binding fragment thereof via a linker.

17. The method of claim 16, wherein the linker is a $(G4S)_n$ linker, wherein n is from 1 to 10.

18. The method of claim 17, wherein the linker is a $(G4S)_3$ linker.

* * * * *

UNITED STATES PATENT AND TRADEMARK OFFICE
CERTIFICATE OF CORRECTION

| | | |
|---|---|---|
| PATENT NO. | : 11,642,390 B2 | Page 1 of 1 |
| APPLICATION NO. | : 17/167990 | |
| DATED | : May 9, 2023 | |
| INVENTOR(S) | : Panayiotis Stevis et al. | |

It is certified that error appears in the above-identified patent and that said Letters Patent is hereby corrected as shown below:

On the Title Page

Item (73) Assignee:
"Regeneran Pharmaceuticals, Inc."
Should read:
--Regeneron Pharmaceuticals, Inc.--

Signed and Sealed this
Sixth Day of August, 2024

Katherine Kelly Vidal
*Director of the United States Patent and Trademark Office*

SEQUENCE LISTING

<160> NUMBER OF SEQ ID NOS: 387

<210> SEQ ID NO 1
<211> LENGTH: 384
<212> TYPE: DNA
<213> ORGANISM: Artificial Sequence
<220> FEATURE:
<223> OTHER INFORMATION: synthetic

<400> SEQUENCE: 1

```
gaggtacaac tggtggagtc tgggggaggc ttggcccagc cggggggtc cctgagactc      60 tcctgtgcag cctctggttt cactttcagt aactattgga tgagctgggt ccgccaggct    120
ccagggaagg gctggagtg gtggccaat ataaaacaag atgggagtga gaaatactat      180
ttggagtctg tgaagggccg attcaccatc tccagagaca acgccaagaa tttattgtat    240
ctgcaaatga acagcctgag agccgaggac acggctgttt tttactgtgc gagacctgga    300
ctattacgct ttttggagcc tggaggcgc tactactccg gtatgaacgt ctggggccaa     360
gggaccacgg tcaccgtctc ctca                                            384
```

<210> SEQ ID NO 2
<211> LENGTH: 128
<212> TYPE: PRT
<213> ORGANISM: Artificial Sequence
<220> FEATURE:
<223> OTHER INFORMATION: synthetic

<400> SEQUENCE: 2

```
Glu Val Gln Leu Val Glu Ser Gly Gly Gly Leu Ala Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Leu Glu Ser Val
    50                  55                  60

Lys Gly Arg Phe Thr Ile Ser Arg Asp Asn Ala Lys Asn Leu Leu Tyr
65                  70                  75                  80

Leu Gln Met Asn Ser Leu Arg Ala Glu Asp Thr Ala Val Phe Tyr Cys
                85                  90                  95

Ala Arg Pro Gly Leu Leu Arg Phe Leu Glu Pro Gly Arg Arg Tyr Tyr
            100                 105                 110

Ser Gly Met Asn Val Trp Gly Gln Gly Thr Thr Val Thr Val Ser Ser
        115                 120                 125
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3

```
ggtttcactt tcagtaacta ttgg                                            24
```

<210> SEQ ID NO 4
<211> LENGTH: 8
<212> TYPE: PRT
<213> ORGANISM: Artificial Sequence
<220> FEATURE:
<223> OTHER INFORMATION: synthetic
```

```
<400> SEQUENCE: 4

Gly Phe Thr Phe Ser Asn Tyr Trp
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
ataaaacaag atgggagtga gaaa                                          24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Lys Gln Asp Gly Ser Glu Lys
1               5

<210> SEQ ID NO 7
<211> LENGTH: 63
<212> TYPE: DNA
<213> ORGANISM: Artificial Sequence
<220> FEATURE:
<223> OTHER INFORMATION: synthetic

<400> SEQUENCE: 7
gcgagacctg gactattacg cttttggag cctgggaggc gctactactc cggtatgaac    60
gtc                                                                 63

<210> SEQ ID NO 8
<211> LENGTH: 21
<212> TYPE: PRT
<213> ORGANISM: Artificial Sequence
<220> FEATURE:
<223> OTHER INFORMATION: synthetic

<400> SEQUENCE: 8

Ala Arg Pro Gly Leu Leu Arg Phe Leu Glu Pro Gly Arg Arg Tyr Tyr
1               5                   10                  15

Ser Gly Met Asn Val
            20

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9
gacatccagt tgacccagtc tccatccttc ctgtctgcat ctgtaggaga cagagtcacc    60
atcacttgct gggccagtca gggcattcgc agttatttag cctggtatca gcaaaaacca   120
gggaaagccc ctaagctcct gatctatgct gcatccactt tgcaaagtgg ggtcccatca   180
aggttcagcg gcagtggatc tgggacagaa ttcactctca caatcagcag cctgcagcct   240
```

```
gaagatttg caacttatta ctgtcaacag tttaatagtt acccgtggac gttcggccaa    300
gggaccaagg tggaaatcaa a                                             321
```

<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10

```
Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Arg Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Trp
                85                  90                  95

Thr Phe Gly Gln Gly Thr Lys Val Glu Ile Lys
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11

```
cagggcattc gcagttat                                                 18
```

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

```
Gln Gly Ile Arg Ser Tyr
1               5
```

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13

```
gctgcatcc                                                           9
```

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caacagttta atagttaccc gtggacg                                         27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Phe Asn Ser Tyr Pro Trp Thr
1               5

<210> SEQ ID NO 17
<211> LENGTH: 342
<212> TYPE: DNA
<213> ORGANISM: Artificial Sequence
<220> FEATURE:
<223> OTHER INFORMATION: synthetic

<400> SEQUENCE: 17
gaggtgcagc tgttggagtc tgggggaggc ttggttcagc ctggggggtc cctgagactc     60
tcctgtgcag cctctggatt cacctttagc aactatgcca tgaactgggt ccgccaggct    120
ccagggaggg ggctggagtg ggtctcagct attcattatg atggtagtaa ttcatattac    180
gcagactccg tgaagggccg gttcaccatc tccagagaca attccaagaa cacgctgtat    240
ctgcaaatga acagcctgag agccgaagac acggccattt attactgtgc gatattgtca    300
agggtctact ggggccaggg aaccctggtc accgtctcct ca                       342

<210> SEQ ID NO 18
<211> LENGTH: 114
<212> TYPE: PRT
<213> ORGANISM: Artificial Sequence
<220> FEATURE:
<223> OTHER INFORMATION: synthetic

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Arg Gly Leu Glu Trp Val
        35                  40                  45

Ser Ala Ile His Tyr Asp Gly Ser Asn Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys

```
            85                  90                  95
Ala Ile Leu Ser Arg Val Tyr Trp Gly Gln Gly Thr Leu Val Thr Val
            100                 105                 110

Ser Ser

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct ttagcaacta tgcc                                          24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Phe Thr Phe Ser Asn Tyr Ala
1               5

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
attcattatg atggtagtaa ttca                                          24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile His Tyr Asp Gly Ser Asn Ser
1               5

<210> SEQ ID NO 23
<211> LENGTH: 21
<212> TYPE: DNA
<213> ORGANISM: Artificial Sequence
<220> FEATURE:
<223> OTHER INFORMATION: synthetic

<400> SEQUENCE: 23
gcgatattgt caagggtcta c                                             21

<210> SEQ ID NO 24
<211> LENGTH: 7
<212> TYPE: PRT
<213> ORGANISM: Artificial Sequence
<220> FEATURE:
<223> OTHER INFORMATION: synthetic

<400> SEQUENCE: 24
```

Ala Ile Leu Ser Arg Val Tyr
1               5

<210> SEQ ID NO 25
<211> LENGTH: 321
<212> TYPE: DNA
<213> ORGANISM: Artificial Sequence
<220> FEATURE:
<223> OTHER INFORMATION: synthetic

<400> SEQUENCE: 25
gacatccaga tgacccagtc tccatcctca ctgtctgcat ctgtaggaga cagagtcacc      60
atcacttgtc gggcgagtca gggcattaac aattatttag cctggtttca gcagaaacca    120
gggaaagccc ctaagtccct gatctatgct acatccagtt tacaaagtgg ggtcccatca    180
aagttcagcg gcagtggatc tgggacagat ttcactctca ccatcagcag cctgcagcct    240
gaagattttg cgacttatta ctgccaacag tataatagtt atccgctcac tttcggcgga    300
gggaccaagg tggagatcaa a                                              321

<210> SEQ ID NO 26
<211> LENGTH: 107
<212> TYPE: PRT
<213> ORGANISM: Artificial Sequence
<220> FEATURE:
<223> OTHER INFORMATION: synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Lys Ala Pro Lys Ser Leu Ile
        35                  40                  45

Tyr Ala Thr Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagggcatta acaattat                                                   18

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

Gln Gly Ile Asn Asn Tyr

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 gctacatcc                                                                  9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Ala Thr Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
caacagtata atagttatcc gctcact                                              27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Gln Gln Tyr Asn Ser Tyr Pro Leu Thr
1               5

<210> SEQ ID NO 33
<211> LENGTH: 387
<212> TYPE: DNA
<213> ORGANISM: Artificial Sequence
<220> FEATURE:
<223> OTHER INFORMATION: synthetic

<400> SEQUENCE: 33
gaggtgcagc tggtggagtc tgggggaggc ttggtccagc ctggggggtc cctgagactc          60
tcctgtgcag cctctggatt cacctttagt aattattgga tgagctgggt ccgccaggct         120
ccagggaagg ggctggagtg ggtggccaac ataaagcaag atggaagtga agatactat          180 gtgggctctg tgaagggccg attcaccatc tccagaggcg acgccgagaa ctctctgtat         240
ctgcaaatga acagcctgag agccgaagac acggctgtat attactgtgc gagagatcga         300
tttggatata gtgcctacga taaggggta cgctactact acggtatgga cgtctggggc          360
caagggacca cggtcaccgt ctcctca                                             387

<210> SEQ ID NO 34
<211> LENGTH: 129

```
<212> TYPE: PRT
<213> ORGANISM: Artificial Sequence
<220> FEATURE:
<223> OTHER INFORMATION: synthetic

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Arg Tyr Tyr Val Gly Ser Val
    50                  55                  60

Lys Gly Arg Phe Thr Ile Ser Arg Gly Asp Ala Glu Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Phe Gly Tyr Ser Ala Tyr Asp Lys Gly Val Arg Tyr
            100                 105                 110

Tyr Tyr Gly Met Asp Val Trp Gly Gln Gly Thr Thr Val Thr Val Ser
        115                 120                 125

Ser

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggattcacct ttagtaatta ttgg                                         24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Thr Phe Ser Asn Tyr Trp
1               5

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
ataaagcaag atggaagtga gaga                                         24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38
```

Ile Lys Gln Asp Gly Ser Glu Arg
1               5

<210> SEQ ID NO 39
<211> LENGTH: 66
<212> TYPE: DNA
<213> ORGANISM: Artificial Sequence
<220> FEATURE:
<223> OTHER INFORMATION: synthetic

<400> SEQUENCE: 39
gcgagagatc gatttggata tagtgcctac gataaggggg tacgctacta ctacggtatg    60
gacgtc                                                              66

<210> SEQ ID NO 40
<211> LENGTH: 22
<212> TYPE: PRT
<213> ORGANISM: Artificial Sequence
<220> FEATURE:
<223> OTHER INFORMATION: synthetic

<400> SEQUENCE: 40

Ala Arg Asp Arg Phe Gly Tyr Ser Ala Tyr Asp Lys Gly Val Arg Tyr
1               5                   10                  15

Tyr Tyr Gly Met Asp Val
            20

<210> SEQ ID NO 41
<211> LENGTH: 321
<212> TYPE: DNA
<213> ORGANISM: Artificial Sequence
<220> FEATURE:
<223> OTHER INFORMATION: synthetic

<400> SEQUENCE: 41
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caactattat ctgtctacag cataatagtt accctcggac gttcggccaa   300
gggaccaagg tggaaatcaa a                                             321

<210> SEQ ID NO 42
<211> LENGTH: 107
<212> TYPE: PRT
<213> ORGANISM: Artificial Sequence
<220> FEATURE:
<223> OTHER INFORMATION: synthetic

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro

```
            65                  70                  75                  80
Glu Asp Phe Ala Thr Tyr Tyr Cys Leu Gln His Asn Ser Tyr Pro Arg
                    85                  90                  95

Thr Phe Gly Gln Gly Thr Lys Val Glu Ile Lys
            100                 105
```

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43
cagggcatta gaaatgat            18

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

Gln Gly Ile Arg Asn Asp
1               5

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 gctgcatcc            9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

Ala Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
ctacagcata atagttaccc tcggacg            27

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Leu Gln His Asn Ser Tyr Pro Arg Thr
1               5

<210> SEQ ID NO 49
<211> LENGTH: 387
<212> TYPE: DNA
<213> ORGANISM: Artificial Sequence
<220> FEATURE:
<223> OTHER INFORMATION: synthetic

<400> SEQUENCE: 49
gaggtgcagc tggtggagtc tgggggaggt ttggtccagc ctgggggtc cctgagactc        60 tcctgtgcag cctctggatt cacctttagt agcttttgga tgagttgggt ccgccaggtt      120
ccagggaagg ggctggagtg ggtggccaac ataaagcaag atggaagtga aaatactat      180 gtggactctg tgaagggccg attcaccatc tccagagaca acgccaagaa ctcactgtat     240
ctgcaaatga acagcctgag agccgaggac acggctgtgt attactgtgc gagagataga     300
tttggatata gtttctacga taaggggta cgttactact acggtatgga cgtctggggc      360
caagggacca cggtcaccgt ctcctca                                          387

<210> SEQ ID NO 50
<211> LENGTH: 129
<212> TYPE: PRT
<213> ORGANISM: Artificial Sequence
<220> FEATURE:
<223> OTHER INFORMATION: synthetic

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Trp Met Ser Trp Val Arg Gln Val Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Phe Gly Tyr Ser Phe Tyr Asp Lys Gly Val Arg Tyr
            100                 105                 110

Tyr Tyr Gly Met Asp Val Trp Gly Gln Gly Thr Thr Val Thr Val Ser
        115                 120                 125

Ser

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggattcacct ttagtagctt ttgg                                              24

<210> SEQ ID NO 52
<211> LENGTH: 8

```
<212> TYPE: PRT
<213> ORGANISM: Artificial Sequence
<220> FEATURE:
<223> OTHER INFORMATION: synthetic

<400> SEQUENCE: 52

Gly Phe Thr Phe Ser Ser Phe Trp
1               5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
ataaagcaag atggaagtga gaaa                                              24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Lys Gln Asp Gly Ser Glu Lys
1               5

<210> SEQ ID NO 55
<211> LENGTH: 66
<212> TYPE: DNA
<213> ORGANISM: Artificial Sequence
<220> FEATURE:
<223> OTHER INFORMATION: synthetic

<400> SEQUENCE: 55
gcgagagata gatttggata tagtttctac gataaggggg tacgttacta ctacggtatg      60
gacgtc                                                                  66

<210> SEQ ID NO 56
<211> LENGTH: 22
<212> TYPE: PRT
<213> ORGANISM: Artificial Sequence
<220> FEATURE:
<223> OTHER INFORMATION: synthetic

<400> SEQUENCE: 56

Ala Arg Asp Arg Phe Gly Tyr Ser Phe Tyr Asp Lys Gly Val Arg Tyr
1               5                   10                  15

Tyr Tyr Gly Met Asp Val
            20

<210> SEQ ID NO 57
<211> LENGTH: 321
<212> TYPE: DNA
<213> ORGANISM: Artificial Sequence
<220> FEATURE:
<223> OTHER INFORMATION: synthetic

<400> SEQUENCE: 57
gacatccaga tgacccagtc tccatcctcc ctgtctgtat ctgtaggaga cagagtcacc      60
atcacttgcc gggcaagtca gggcattaga aatgatttag gtggtatca gcagaaacca     120
```

```
gggaaagccc ctaagcgcct gatctatgct acatccagtt tgcaaagtgg ggtcccatca      180
aggttcagcg gcagtggatc tgggacagaa ttcactctca caatcagcgg cctgcagcct      240
gaagattttg caacttatta ctgtctacag cataatagtt accctcggac gttcggccaa      300
gggaccaagg tggaaatcaa a                                                321
```

<210> SEQ ID NO 58
<211> LENGTH: 107
<212> TYPE: PRT
<213> ORGANISM: Artificial Sequence
<220> FEATURE:
<223> OTHER INFORMATION: synthetic

<400> SEQUENCE: 58

```
Asp Ile Gln Met Thr Gln Ser Pro Ser Ser Leu Ser Val Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys
            100                 105
```

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59

```
cagggcatta gaaatgat                                                     18
```

<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

```
Gln Gly Ile Arg Asn Asp
1               5
```

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61

```
gctacatcc                                                                9
```

<210> SEQ ID NO 62
<211> LENGTH: 3

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Ala Thr Ser
1

<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
ctacagcata atagttaccc tcggacg                                          27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Leu Gln His Asn Ser Tyr Pro Arg Thr
1               5

<210> SEQ ID NO 65
<211> LENGTH: 387
<212> TYPE: DNA
<213> ORGANISM: Artificial Sequence
<220> FEATURE:
<223> OTHER INFORMATION: synthetic

<400> SEQUENCE: 65
gaggtgcagc tggtggagtc tgggggaggc ttggtccagc ctggggggtc cctgagactc      60
tcctgtgcag cctctggatt cacctttagt aactattgga tgagctgggt ccgcctggct     120
ccagggaagg ggctggagtg ggtggccaac ataaagcaag atggaagtga gagatactat     180
gtgggctctg tgaagggccg attcaccatc tccagaggcg acgccaagaa ctcactgtat     240
ctgcaaatga acagcctgag agccgaggac acggctgtgt attactgtgc gagagatcga     300
tttggatata gtgccttcga taaggggta cgctactact acggtatgga cgtctggggc     360
caagggacca cggtcaccgt ctcttca                                         387

<210> SEQ ID NO 66
<211> LENGTH: 129
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Leu Ala Pro Gly Lys Gly Leu Glu Trp Val
        35                  40                  45

Ala Asn Ile Lys Gln Asp Gly Ser Glu Arg Tyr Tyr Val Gly Ser Val

```
            50                  55                  60
Lys Gly Arg Phe Thr Ile Ser Arg Gly Asp Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Phe Gly Tyr Ser Ala Phe Asp Lys Gly Val Arg Tyr
            100                 105                 110

Tyr Tyr Gly Met Asp Val Trp Gly Gln Gly Thr Thr Val Thr Val Ser
        115                 120                 125

Ser

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggattcacct ttagtaacta ttgg                                          24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Phe Ser Asn Tyr Trp
 1               5

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
ataaagcaag atggaagtga gaga                                          24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Ile Lys Gln Asp Gly Ser Glu Arg
 1               5

<210> SEQ ID NO 71
<211> LENGTH: 66
<212> TYPE: DNA
<213> ORGANISM: Artificial Sequence
<220> FEATURE:
<223> OTHER INFORMATION: synthetic

<400> SEQUENCE: 71
gcgagagatc gatttggata tagtgccttc gataaggggg tacgctacta ctacggtatg   60
gacgtc                                                              66
```

<210> SEQ ID NO 72
<211> LENGTH: 22
<212> TYPE: PRT
<213> ORGANISM: Artificial Sequence
<220> FEATURE:
<223> OTHER INFORMATION: synthetic

<400> SEQUENCE: 72

Ala Arg Asp Arg Phe Gly Tyr Ser Ala Phe Asp Lys Gly Val Arg Tyr
1               5                   10                  15

Tyr Tyr Gly Met Asp Val
            20

<210> SEQ ID NO 73
<211> LENGTH: 321
<212> TYPE: DNA
<213> ORGANISM: Artificial Sequence
<220> FEATURE:
<223> OTHER INFORMATION: synthetic

<400> SEQUENCE: 73
gacatccaga tgacccagtc tccatcctcc ctgtctgcat ctgtaggaga cagagtcacc     60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt accctcggac gttcggccaa    300
gggaccaagg tggaaatcaa a                                              321

<210> SEQ ID NO 74
<211> LENGTH: 107
<212> TYPE: PRT
<213> ORGANISM: Artificial Sequence
<220> FEATURE:
<223> OTHER INFORMATION: synthetic

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys
            100                 105

<210> SEQ ID NO 75
<211> LENGTH: 18
<212> TYPE: DNA
<213> ORGANISM: Artificial Sequence
<220> FEATURE:
<223> OTHER INFORMATION: synthetic

<400> SEQUENCE: 75
cagggcatta gaaatgat 18

<210> SEQ ID NO 76
<211> LENGTH: 6
<212> TYPE: PRT
<213> ORGANISM: Artificial Sequence
<220> FEATURE:
<223> OTHER INFORMATION: synthetic

<400> SEQUENCE: 76

Gln Gly Ile Arg Asn Asp
1               5

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 gctgcatcc 9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Ala Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: synthetic

<400> SEQUENCE: 79
ctacagcata atagttaccc tcggacg 27

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Leu Gln His Asn Ser Tyr Pro Arg Thr
1               5

<210> SEQ ID NO 81
<211> LENGTH: 387
<212> TYPE: DNA
<213> ORGANISM: Artificial Sequence
<220> FEATURE:
<223> OTHER INFORMATION: synthetic

<400> SEQUENCE: 81
gaggtgcagc tggtggagtc tgggggaggt ttggtccagc ctgggggtc cctgagactc      60 tcctgtgcag cctctggatt cacctttagt agcttttgga tgagttgggt ccgccaggtt    120

```
ccagggaagg ggctgcagtg ggtggccaac ataaagcaag atggaagtga gaaatactat    180
gtggactctg tgaagggccg attcaccatc tccagagaca cgccaagaa ctcactgtat     240 ctgcaaatga acagcctgag agccgaggac acggctgtgt attactgtgc gagagataga    300
tttggatata gtgtctacga taaggggta cgctactact acggtatgga cgtctggggc     360
caagggacca cggtcaccgt ctcctca                                        387
```

<210> SEQ ID NO 82
<211> LENGTH: 129
<212> TYPE: PRT
<213> ORGANISM: Artificial Sequence
<220> FEATURE:
<223> OTHER INFORMATION: synthetic

<400> SEQUENCE: 82

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
            20                  25                  30

Trp Met Ser Trp Val Arg Gln Val Pro Gly Lys Gly Leu Gln Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Phe Gly Tyr Ser Val Tyr Asp Lys Gly Val Arg Tyr
            100                 105                 110

Tyr Tyr Gly Met Asp Val Trp Gly Gln Gly Thr Thr Val Thr Val Ser
        115                 120                 125

Ser
```

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83

```
ggattcacct ttagtagctt ttgg                                           24
```

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

```
Gly Phe Thr Phe Ser Ser Phe Trp
 1               5
```

<210> SEQ ID NO 85
<211> LENGTH: 24
<212> TYPE: DNA
<213> ORGANISM: Artificial Sequence
<220> FEATURE:
<223> OTHER INFORMATION: synthetic

<400> SEQUENCE: 85
ataaagcaag atggaagtga gaaa                                              24

<210> SEQ ID NO 86
<211> LENGTH: 8
<212> TYPE: PRT
<213> ORGANISM: Artificial Sequence
<220> FEATURE:
<223> OTHER INFORMATION: synthetic

<400> SEQUENCE: 86

Ile Lys Gln Asp Gly Ser Glu Lys
1               5

<210> SEQ ID NO 87
<211> LENGTH: 66
<212> TYPE: DNA
<213> ORGANISM: Artificial Sequence
<220> FEATURE:
<223> OTHER INFORMATION: synthetic

<400> SEQUENCE: 87
gcgagagata gatttggata tagtgtctac gataagggg tacgctacta ctacggtatg        60
gacgtc                                                                  66

<210> SEQ ID NO 88
<211> LENGTH: 22
<212> TYPE: PRT
<213> ORGANISM: Artificial Sequence
<220> FEATURE:
<223> OTHER INFORMATION: synthetic

<400> SEQUENCE: 88

Ala Arg Asp Arg Phe Gly Tyr Ser Val Tyr Asp Lys Gly Val Arg Tyr
1               5                   10                  15

Tyr Tyr Gly Met Asp Val
            20

<210> SEQ ID NO 89
<211> LENGTH: 321
<212> TYPE: DNA
<213> ORGANISM: Artificial Sequence
<220> FEATURE:
<223> OTHER INFORMATION: synthetic

<400> SEQUENCE: 89
gacatccaga tgacccagtc tccatcctcc ctgtctgtat ctgtaggaga cagagtcacc        60
atcacttgcc gggcaagtca gggcattaga aatgatttag ctggtatca gcagaaacca       120 gggaaagccc ctaagcgcct gatctatgct gcatccagtt tgcaaagtgg ggtcccatca      180
aggttcagcg gcagtggatc tgggacagaa ttcactctca caatcagcgg cctgcagtct      240
gaagattttg caacttatta ctgtctacag cataagagtt accctcggac gttcggccaa      300
gggaccaagg tggaaatcaa a                                                321

<210> SEQ ID NO 90
<211> LENGTH: 107
<212> TYPE: PRT
<213> ORGANISM: Artificial Sequence
<220> FEATURE:
<223> OTHER INFORMATION: synthetic

<400> SEQUENCE: 90

```
Asp Ile Gln Met Thr Gln Ser Pro Ser Ser Leu Ser Val Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Gly Leu Gln Ser
65                  70                  75                  80

Glu Asp Phe Ala Thr Tyr Tyr Cys Leu Gln His Lys Ser Tyr Pro Arg
                85                  90                  95

Thr Phe Gly Gln Gly Thr Lys Val Glu Ile Lys
            100                 105
```

<210> SEQ ID NO 91
<211> LENGTH: 18
<212> TYPE: DNA
<213> ORGANISM: Artificial Sequence
<220> FEATURE:
<223> OTHER INFORMATION: synthetic

<400> SEQUENCE: 91
cagggcatta gaaatgat                                                18

<210> SEQ ID NO 92
<211> LENGTH: 6
<212> TYPE: PRT
<213> ORGANISM: Artificial Sequence
<220> FEATURE:
<223> OTHER INFORMATION: synthetic

<400> SEQUENCE: 92

Gln Gly Ile Arg Asn Asp
1               5

<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93 gctgcatcc                                                           9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Ala Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: synthetic

<400> SEQUENCE: 95
ctacagcata agagttaccc tcggacg                                            27

<210> SEQ ID NO 96
<211> LENGTH: 9
<212> TYPE: PRT
<213> ORGANISM: Artificial Sequence
<220> FEATURE:
<223> OTHER INFORMATION: synthetic

<400> SEQUENCE: 96

Leu Gln His Lys Ser Tyr Pro Arg Thr
1               5

<210> SEQ ID NO 97
<211> LENGTH: 378
<212> TYPE: DNA
<213> ORGANISM: Artificial Sequence
<220> FEATURE:
<223> OTHER INFORMATION: synthetic

<400> SEQUENCE: 97
caggtgaagt tggtggagtc tgggggaggc gtggtccagc ctgggaggtc cctgagactc        60
tcctgtgcag cgtctggatt caccttcagt aactatgtca tacactgggt ccgccaggct       120
ccaggcaagg ggctggagtg gtggcggtt atatggtatg atggaagtaa taatactat         180 gcagactccg tgaagggccg attcaccatc tccagagaca actccaagaa tacgctgtat       240
ttgcaaatga acagcctgag agccgaggac acggctgtgt attactgtgc gagagatcgg       300
gtggttcggg gagtcgatta ctactactac tacggtttgg acgtctgggg ccaagggacc       360
tcggtcaccg tctcctca                                                    378

<210> SEQ ID NO 98
<211> LENGTH: 126
<212> TYPE: PRT
<213> ORGANISM: Artificial Sequence
<220> FEATURE:
<223> OTHER INFORMATION: synthetic

<400> SEQUENCE: 98

Gln Val Lys Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Val Ile His Trp Val Arg Gln Ala Pro Gly Lys Gly Leu Glu Trp Val
        35                  40                  45

Ala Val Ile Trp Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Val Arg Gly Val Asp Tyr Tyr Tyr Tyr Tyr Gly
            100                 105                 110

Leu Asp Val Trp Gly Gln Gly Thr Ser Val Thr Val Ser Ser
        115                 120                 125

<210> SEQ ID NO 99
<211> LENGTH: 24

```
<212> TYPE: DNA
<213> ORGANISM: Artificial Sequence
<220> FEATURE:
<223> OTHER INFORMATION: synthetic

<400> SEQUENCE: 99
ggattcacct tcagtaacta tgtc                                           24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Gly Phe Thr Phe Ser Asn Tyr Val
1               5

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
atatggtatg atggaagtaa taaa                                           24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Trp Tyr Asp Gly Ser Asn Lys
1               5

<210> SEQ ID NO 103
<211> LENGTH: 57
<212> TYPE: DNA
<213> ORGANISM: Artificial Sequence
<220> FEATURE:
<223> OTHER INFORMATION: synthetic

<400> SEQUENCE: 103
gcgagagatc gggtggttcg gggagtcgat tactactact actacggttt ggacgtc      57

<210> SEQ ID NO 104
<211> LENGTH: 19
<212> TYPE: PRT
<213> ORGANISM: Artificial Sequence
<220> FEATURE:
<223> OTHER INFORMATION: synthetic

<400> SEQUENCE: 104

Ala Arg Asp Arg Val Val Arg Gly Val Asp Tyr Tyr Tyr Tyr Gly
1               5                   10                  15

Leu Asp Val

<210> SEQ ID NO 105
<211> LENGTH: 321
<212> TYPE: DNA
<213> ORGANISM: Artificial Sequence
```

<220> FEATURE:
<223> OTHER INFORMATION: synthetic

<400> SEQUENCE: 105

```
gaaatagtga tgacgcagtc tccagccacc ctgtctgtgt ctccagggga aagagccacc      60
ctctcctgca gggccagtca gagtgttaga agcaacttag cctggtacca acagaaacct    120
ggccaggctc ccaggctcct catctatggt gcatcctcca gggccactgg tatcccagcc    180
aggttcagtg gcactgggtc tgggacagag ttcactctca ccatcagcag cctgcagtct    240
gacgattttg cagtttatta ctgtcagcaa tataataagt ggcctcggac gttcggccaa    300
gggaccaagg tggaaatcaa g                                               321
```

<210> SEQ ID NO 106
<211> LENGTH: 107
<212> TYPE: PRT
<213> ORGANISM: Artificial Sequence
<220> FEATURE:
<223> OTHER INFORMATION: synthetic

<400> SEQUENCE: 106

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Ala Arg Phe Ser Gly
    50                  55                  60

Thr Gly Ser Gly Thr Glu Phe Thr Leu Thr Ile Ser Ser Leu Gln Ser
65                  70                  75                  80

Asp Asp Phe Ala Val Tyr Tyr Cys Gln Gln Tyr Asn Lys Trp Pro Arg
                85                  90                  95

Thr Phe Gly Gln Gly Thr Lys Val Glu Ile Lys
            100                 105
```

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107

```
cagagtgtta gaagcaac                                                    18
```

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

```
Gln Ser Val Arg Ser Asn
1               5
```

<210> SEQ ID NO 109
<211> LENGTH: 9
<212> TYPE: DNA
<213> ORGANISM: Artificial Sequence
<220> FEATURE:

<223> OTHER INFORMATION: synthetic

<400> SEQUENCE: 109 ggtgcatcc                                                                  9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Gly Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: synthetic

<400> SEQUENCE: 111
cagcaatata ataagtggcc tcggacg                                              27

<210> SEQ ID NO 112
<211> LENGTH: 9
<212> TYPE: PRT
<213> ORGANISM: Artificial Sequence
<220> FEATURE:
<223> OTHER INFORMATION: synthetic

<400> SEQUENCE: 112

Gln Gln Tyr Asn Lys Trp Pro Arg Thr
1               5

<210> SEQ ID NO 113
<211> LENGTH: 369
<212> TYPE: DNA
<213> ORGANISM: Artificial Sequence
<220> FEATURE:
<223> OTHER INFORMATION: synthetic

<400> SEQUENCE: 113
gaggtgcagc tggtggagtc tgggggaggc ttggtaaaac tggggggtc ccttagactc           60 tcctgtgcag cctctggaat cactttcagt aacgcctgga tgagctgggt ccgccaggct         120
ccagggaagg ggctggagtg ggttggccgt attaaaagca agttgatgg tgggacaata          180 gactacgctg cacccgtgaa aggcagattc accatctcaa gagatgattc aaaaaacacg         240
ctgtatctgc aaatgaacag cctgaaaacc gaggacacag ccgtttatta ctgtaccaca         300
ggtcgaatta ctatggttcg gggagttttg ggctactggg gccagggaac cctggtcacc         360
gtctcctca                                                                 369

<210> SEQ ID NO 114
<211> LENGTH: 123
<212> TYPE: PRT
<213> ORGANISM: Artificial Sequence
<220> FEATURE:
<223> OTHER INFORMATION: synthetic

<400> SEQUENCE: 114

Glu Val Gln Leu Val Glu Ser Gly Gly Gly Leu Val Lys Pro Gly Gly

```
                1               5                   10                  15
Ser Leu Arg Leu Ser Cys Ala Ala Ser Gly Ile Thr Phe Ser Asn Ala
            20                  25                  30

Trp Met Ser Trp Val Arg Gln Ala Pro Gly Lys Gly Leu Glu Trp Val
            35                  40                  45

Gly Arg Ile Lys Ser Lys Val Asp Gly Gly Thr Ile Asp Tyr Ala Ala
            50                  55                  60

Pro Val Lys Gly Arg Phe Thr Ile Ser Arg Asp Asp Ser Lys Asn Thr
 65                 70                  75                  80

Leu Tyr Leu Gln Met Asn Ser Leu Lys Thr Glu Asp Thr Ala Val Tyr
                85                  90                  95

Tyr Cys Thr Thr Gly Arg Ile Thr Met Val Arg Gly Val Leu Gly Tyr
                100                 105                 110

Trp Gly Gln Gly Thr Leu Val Thr Val Ser Ser
            115                 120
```

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115
ggaatcactt tcagtaacgc ctgg                                    24

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

```
Gly Ile Thr Phe Ser Asn Ala Trp
 1               5
```

<210> SEQ ID NO 117
<211> LENGTH: 30
<212> TYPE: DNA
<213> ORGANISM: Artificial Sequence
<220> FEATURE:
<223> OTHER INFORMATION: synthetic

<400> SEQUENCE: 117
attaaaagca aagttgatgg tgggacaata                              30

<210> SEQ ID NO 118
<211> LENGTH: 10
<212> TYPE: PRT
<213> ORGANISM: Artificial Sequence
<220> FEATURE:
<223> OTHER INFORMATION: synthetic

<400> SEQUENCE: 118

```
Ile Lys Ser Lys Val Asp Gly Gly Thr Ile
 1               5                  10
```

<210> SEQ ID NO 119
<211> LENGTH: 42
<212> TYPE: DNA
<213> ORGANISM: Artificial Sequence
<220> FEATURE:

<223> OTHER INFORMATION: synthetic

<400> SEQUENCE: 119
accacaggtc gaattactat ggttcgggga gttttgggct ac                          42

<210> SEQ ID NO 120
<211> LENGTH: 14
<212> TYPE: PRT
<213> ORGANISM: Artificial Sequence
<220> FEATURE:
<223> OTHER INFORMATION: synthetic

<400> SEQUENCE: 120

Thr Thr Gly Arg Ile Thr Met Val Arg Gly Val Leu Gly Tyr
1               5                   10

<210> SEQ ID NO 121
<211> LENGTH: 336
<212> TYPE: DNA
<213> ORGANISM: Artificial Sequence
<220> FEATURE:
<223> OTHER INFORMATION: synthetic

<400> SEQUENCE: 121
gacatcgtga tgacccagtc tccagactcc ctggctgtgt ctctgggcga gagggccacc      60
atcaactgca gtccagcca gagtgtttta tacagctcca acaataagaa ctacttagct      120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggct gtttattact gtcagcaata ttatagtact     300 tacactttg gccaggggac caagctggag atcaaa                                336

<210> SEQ ID NO 122
<211> LENGTH: 112
<212> TYPE: PRT
<213> ORGANISM: Artificial Sequence
<220> FEATURE:
<223> OTHER INFORMATION: synthetic

<400> SEQUENCE: 122

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Tyr Thr Phe Gly Gln Gly Thr Lys Leu Glu Ile Lys
            100                 105                 110

<210> SEQ ID NO 123
<211> LENGTH: 36
<212> TYPE: DNA
<213> ORGANISM: Artificial Sequence
<220> FEATURE:
<223> OTHER INFORMATION: synthetic

```
<400> SEQUENCE: 123
cagagtgttt tatacagctc caacaataag aactac                                36

<210> SEQ ID NO 124
<211> LENGTH: 12
<212> TYPE: PRT
<213> ORGANISM: Artificial Sequence
<220> FEATURE:
<223> OTHER INFORMATION: synthetic

<400> SEQUENCE: 124

Gln Ser Val Leu Tyr Ser Ser Asn Asn Lys Asn Tyr
1               5                   10

<210> SEQ ID NO 125
<211> LENGTH: 9
<212> TYPE: DNA
<213> ORGANISM: Artificial Sequence
<220> FEATURE:
<223> OTHER INFORMATION: synthetic

<400> SEQUENCE: 125 tgggcatct                                                              9

<210> SEQ ID NO 126
<211> LENGTH: 3
<212> TYPE: PRT
<213> ORGANISM: Artificial Sequence
<220> FEATURE:
<223> OTHER INFORMATION: synthetic

<400> SEQUENCE: 126

Trp Ala Ser
1

<210> SEQ ID NO 127
<211> LENGTH: 24
<212> TYPE: DNA
<213> ORGANISM: Artificial Sequence
<220> FEATURE:
<223> OTHER INFORMATION: synthetic

<400> SEQUENCE: 127
cagcaatatt atagtactta cact                                             24

<210> SEQ ID NO 128
<211> LENGTH: 8
<212> TYPE: PRT
<213> ORGANISM: Artificial Sequence
<220> FEATURE:
<223> OTHER INFORMATION: synthetic

<400> SEQUENCE: 128

Gln Gln Tyr Tyr Ser Thr Tyr Thr
1               5

<210> SEQ ID NO 129
<211> LENGTH: 369
<212> TYPE: DNA
<213> ORGANISM: Artificial Sequence
<220> FEATURE:
<223> OTHER INFORMATION: synthetic

<400> SEQUENCE: 129
gaggtgcagc tggtggagtc tgggggaggc ttggtaaagc ctggggggtc ccttagactc       60
```

```
tcctgtgcag cctctggaat cactttcagt aacgcctgga tgagctgggt ccgccaggct    120
ccagggaagg ggctggagtg ggttggccgt tttaaaggca aagctgatgg tgggacagtt    180
gactatgctg cacccgtgaa aggcagattc accatctcaa gagatgattc gaaaaacacg    240
ctgtatctgc aaatgaacag tctgaaaaac gaggacacag ccgtgtatta ctgcaccaca    300
ggtcgaatta ctatggttcg gggagttttg ggctactggg gccagggaac cctggtcact    360
gtctcctca                                                            369
```

<210> SEQ ID NO 130
<211> LENGTH: 123
<212> TYPE: PRT
<213> ORGANISM: Artificial Sequence
<220> FEATURE:
<223> OTHER INFORMATION: synthetic

<400> SEQUENCE: 130

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Ile Thr Phe Ser Asn Ala
            20                  25                  30

Trp Met Ser Trp Val Arg Gln Ala Pro Gly Lys Gly Leu Glu Trp Val
        35                  40                  45

Gly Arg Phe Lys Gly Lys Ala Asp Gly Gly Thr Val Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Asn Glu Asp Thr Ala Val Tyr
                85                  90                  95

Tyr Cys Thr Thr Gly Arg Ile Thr Met Val Arg Gly Val Leu Gly Tyr
            100                 105                 110

Trp Gly Gln Gly Thr Leu Val Thr Val Ser Ser
        115                 120
```

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131

```
ggaatcactt tcagtaacgc ctgg                                            24
```

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

```
Gly Ile Thr Phe Ser Asn Ala Trp
1               5
```

<210> SEQ ID NO 133
<211> LENGTH: 30
<212> TYPE: DNA
<213> ORGANISM: Artificial Sequence
<220> FEATURE:
<223> OTHER INFORMATION: synthetic

```
<400> SEQUENCE: 133
tttaaaggca aagctgatgg tgggacagtt                                          30

<210> SEQ ID NO 134
<211> LENGTH: 10
<212> TYPE: PRT
<213> ORGANISM: Artificial Sequence
<220> FEATURE:
<223> OTHER INFORMATION: synthetic

<400> SEQUENCE: 134

Phe Lys Gly Lys Ala Asp Gly Gly Thr Val
1               5                   10

<210> SEQ ID NO 135
<211> LENGTH: 42
<212> TYPE: DNA
<213> ORGANISM: Artificial Sequence
<220> FEATURE:
<223> OTHER INFORMATION: synthetic

<400> SEQUENCE: 135
accacaggtc gaattactat ggttcgggga gttttgggct ac                            42

<210> SEQ ID NO 136
<211> LENGTH: 14
<212> TYPE: PRT
<213> ORGANISM: Artificial Sequence
<220> FEATURE:
<223> OTHER INFORMATION: synthetic

<400> SEQUENCE: 136

Thr Thr Gly Arg Ile Thr Met Val Arg Gly Val Leu Gly Tyr
1               5                   10

<210> SEQ ID NO 137
<211> LENGTH: 336
<212> TYPE: DNA
<213> ORGANISM: Artificial Sequence
<220> FEATURE:
<223> OTHER INFORMATION: synthetic

<400> SEQUENCE: 137
gacatcgtga tgacccagtc tccagactcc ctggctgtgt ctctgggcga gagggccacc         60
atcaactgca gtccagcca gagtgtttta tacacctcca acaataagaa ctacttagct         120
tggtaccagc agaaaccagg acagcctcct aaactgctca tttactgggc atctacccgg         180
gaatccgggg tccctgaccg attcagtggc agcgggtctg ggacagattt cactctcacc         240
atcagcagcc tgcaggctga agatgtggca gtttattact gtcagcaata ttatagtact        300 tacactttg gccaggggac caagctggag atcaaa                                    336

<210> SEQ ID NO 138
<211> LENGTH: 112
<212> TYPE: PRT
<213> ORGANISM: Artificial Sequence
<220> FEATURE:
<223> OTHER INFORMATION: synthetic

<400> SEQUENCE: 138

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Thr
```

```
                20                  25                  30
Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Tyr Thr Phe Gly Gln Gly Thr Lys Leu Glu Ile Lys
            100                 105                 110
```

<210> SEQ ID NO 139
<211> LENGTH: 36
<212> TYPE: DNA
<213> ORGANISM: Artificial Sequence
<220> FEATURE:
<223> OTHER INFORMATION: synthetic

<400> SEQUENCE: 139
cagagtgttt tatacacctc aacaataag aactac                              36

<210> SEQ ID NO 140
<211> LENGTH: 12
<212> TYPE: PRT
<213> ORGANISM: Artificial Sequence
<220> FEATURE:
<223> OTHER INFORMATION: synthetic

<400> SEQUENCE: 140

```
Gln Ser Val Leu Tyr Thr Ser Asn Asn Lys Asn Tyr
1               5                   10
```

<210> SEQ ID NO 141
<211> LENGTH: 9
<212> TYPE: DNA
<213> ORGANISM: Artificial Sequence
<220> FEATURE:
<223> OTHER INFORMATION: synthetic

<400> SEQUENCE: 141 tgggcatct                                                            9

<210> SEQ ID NO 142
<211> LENGTH: 3
<212> TYPE: PRT
<213> ORGANISM: Artificial Sequence
<220> FEATURE:
<223> OTHER INFORMATION: synthetic

<400> SEQUENCE: 142

Trp Ala Ser
1

<210> SEQ ID NO 143
<211> LENGTH: 24
<212> TYPE: DNA
<213> ORGANISM: Artificial Sequence
<220> FEATURE:
<223> OTHER INFORMATION: synthetic

<400> SEQUENCE: 143
cagcaatatt atagtactta cact                                          24

<210> SEQ ID NO 144
<211> LENGTH: 8
<212> TYPE: PRT
<213> ORGANISM: Artificial Sequence
<220> FEATURE:
<223> OTHER INFORMATION: synthetic

<400> SEQUENCE: 144

Gln Gln Tyr Tyr Ser Thr Tyr Thr
1               5

<210> SEQ ID NO 145
<211> LENGTH: 369
<212> TYPE: DNA
<213> ORGANISM: Artificial Sequence
<220> FEATURE:
<223> OTHER INFORMATION: synthetic

<400> SEQUENCE: 145
caggtgcagc tggtgcagtc tggggctgag gtgaagaagc ctggggcctc agtggaggtc      60
tcctgcaagg cttctggata caccttcacc gactactata tacactggat acgacaggcc     120
cctggacaag gcttgagtg gatgggatgg atcaaccctg acagtggtcg cacaaactat      180
gcacagaagt ttcaggtcag ggtcaccatg accagggaca cgtccatcac cacagcctac     240
atggaactga acagactgaa atctgacgac acggccgtgt attactgtgc gagaggaccc     300
ctacgtggat atagcggcta cgattttttt gactactggg gccagggaac cctggtcacc     360
gtctcctca                                                             369

<210> SEQ ID NO 146
<211> LENGTH: 123
<212> TYPE: PRT
<213> ORGANISM: Artificial Sequence
<220> FEATURE:
<223> OTHER INFORMATION: synthetic

<400> SEQUENCE: 146

Gln Val Gln Leu Val Gln Ser Gly Ala Glu Val Lys Lys Pro Gly Ala
1               5                   10                  15

Ser Val Glu Val Ser Cys Lys Ala Ser Gly Tyr Thr Phe Thr Asp Tyr
            20                  25                  30

Tyr Ile His Trp Ile Arg Gln Ala Pro Gly Gln Gly Leu Glu Trp Met
        35                  40                  45

Gly Trp Ile Asn Pro Asp Ser Gly Arg Thr Asn Tyr Ala Gln Lys Phe
    50                  55                  60

Gln Val Arg Val Thr Met Thr Arg Asp Thr Ser Ile Thr Thr Ala Tyr
65                  70                  75                  80

Met Glu Leu Asn Arg Leu Lys Ser Asp Asp Thr Ala Val Tyr Tyr Cys
                85                  90                  95

Ala Arg Gly Pro Leu Arg Gly Tyr Ser Gly Tyr Asp Phe Phe Asp Tyr
            100                 105                 110

Trp Gly Gln Gly Thr Leu Val Thr Val Ser Ser
        115                 120

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147
ggatacacct tcaccgacta ctat 24

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

Gly Tyr Thr Phe Thr Asp Tyr Tyr
1               5

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149
atcaaccctg acagtggtcg caca 24

<210> SEQ ID NO 150
<211> LENGTH: 8
<212> TYPE: PRT
<213> ORGANISM: Artificial Sequence
<220> FEATURE:
<223> OTHER INFORMATION: synthetic

<400> SEQUENCE: 150

Ile Asn Pro Asp Ser Gly Arg Thr
1               5

<210> SEQ ID NO 151
<211> LENGTH: 48
<212> TYPE: DNA
<213> ORGANISM: Artificial Sequence
<220> FEATURE:
<223> OTHER INFORMATION: synthetic

<400> SEQUENCE: 151
gcgagaggac ccctacgtgg atatagcggc tacgattttt ttgactac 48

<210> SEQ ID NO 152
<211> LENGTH: 16
<212> TYPE: PRT
<213> ORGANISM: Artificial Sequence
<220> FEATURE:
<223> OTHER INFORMATION: synthetic

<400> SEQUENCE: 152

Ala Arg Gly Pro Leu Arg Gly Tyr Ser Gly Tyr Asp Phe Phe Asp Tyr
1               5                   10                  15

<210> SEQ ID NO 153
<211> LENGTH: 321
<212> TYPE: DNA
<213> ORGANISM: Artificial Sequence
<220> FEATURE:
<223> OTHER INFORMATION: synthetic

<400> SEQUENCE: 153
gacatccagt tgacccagtc tccatccttc ctgtctgcat ctgtaggaga cagagtcacc 60

```
atcacttgct gggccagtca gggcattagc agttatttag cctggtatca gcaaaaacca    120
gggaaagccc ctaagctcct gatctatgct gcatccactt tgcaaagtgg ggtcccatca    180
aggttcagcg gcagtggatc tgggacagaa ttcactctca caatcagcag cctgcagcct    240
gaagattttg caagttattt ctgtcaacag cttaatagta accctcggac gttcggccaa    300
gggaccaagg tggaaatcaa a                                              321
```

<210> SEQ ID NO 154
<211> LENGTH: 107
<212> TYPE: PRT
<213> ORGANISM: Artificial Sequence
<220> FEATURE:
<223> OTHER INFORMATION: synthetic

<400> SEQUENCE: 154

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ser Tyr Phe Cys Gln Gln Leu Asn Ser Asn Pro Arg
                85                  90                  95

Thr Phe Gly Gln Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155

```
cagggcatta gcagttat                                                   18
```

<210> SEQ ID NO 156
<211> LENGTH: 6
<212> TYPE: PRT
<213> ORGANISM: Artificial Sequence
<220> FEATURE:
<223> OTHER INFORMATION: synthetic

<400> SEQUENCE: 156

Gln Gly Ile Ser Ser Tyr
1               5

<210> SEQ ID NO 157
<211> LENGTH: 9
<212> TYPE: DNA
<213> ORGANISM: Artificial Sequence
<220> FEATURE:
<223> OTHER INFORMATION: synthetic

<400> SEQUENCE: 157

```
gctgcatcc                                                              9
```

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

Ala Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: synthetic

<400> SEQUENCE: 159
caacagctta atagtaaccc tcggacg        27

<210> SEQ ID NO 160
<211> LENGTH: 9
<212> TYPE: PRT
<213> ORGANISM: Artificial Sequence
<220> FEATURE:
<223> OTHER INFORMATION: synthetic

<400> SEQUENCE: 160

Gln Gln Leu Asn Ser Asn Pro Arg Thr
1               5

<210> SEQ ID NO 161
<211> LENGTH: 363
<212> TYPE: DNA
<213> ORGANISM: Artificial Sequence
<220> FEATURE:
<223> OTHER INFORMATION: synthetic

<400> SEQUENCE: 161
gaagtgcagc tggtggagtc tgggggaggc ttggtacagc ctggcaggtc cctgagactc        60
tcctgtgcag cctctggatt cacctttgat gattatgcca tgcactgggt ccggcaagtt       120
ccagggaagg gcctggagtg ggtctcaggt attacttgga atagtggtga cataggctat       180
gcggactctg tgaagggccg attcaccatc tccagagaca cgccaagaa ctccctatat       240
ctgcaaatga acagtctaag agctgaggac acggccttgt attactgtac aaaagataaa       300
gatagcagtg gctactacgg tattgacgtc tggggccaag ggaccacggt caccgtctcc       360
tca                                                                    363

<210> SEQ ID NO 162
<211> LENGTH: 121
<212> TYPE: PRT
<213> ORGANISM: Artificial Sequence
<220> FEATURE:
<223> OTHER INFORMATION: synthetic

<400> SEQUENCE: 162

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Thr Trp Asn Ser Gly Asp Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Asp Lys Asp Ser Ser Gly Tyr Tyr Gly Ile Asp Val Trp Gly
            100                 105                 110

Gln Gly Thr Thr Val Thr Val Ser Ser
        115                 120

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163
ggattcacct ttgatgatta tgcc                                      24

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

Gly Phe Thr Phe Asp Asp Tyr Ala
1               5

<210> SEQ ID NO 165
<211> LENGTH: 24
<212> TYPE: DNA
<213> ORGANISM: Artificial Sequence
<220> FEATURE:
<223> OTHER INFORMATION: synthetic

<400> SEQUENCE: 165
attacttgga atagtggtga cata                                      24

<210> SEQ ID NO 166
<211> LENGTH: 8
<212> TYPE: PRT
<213> ORGANISM: Artificial Sequence
<220> FEATURE:
<223> OTHER INFORMATION: synthetic

<400> SEQUENCE: 166

Ile Thr Trp Asn Ser Gly Asp Ile
1               5

<210> SEQ ID NO 167
<211> LENGTH: 42
<212> TYPE: DNA
<213> ORGANISM: Artificial Sequence
<220> FEATURE:
<223> OTHER INFORMATION: synthetic

<400> SEQUENCE: 167
acaaaagata aagatagcag tggctactac ggtattgacg tc                  42

```
<210> SEQ ID NO 168
<211> LENGTH: 14
<212> TYPE: PRT
<213> ORGANISM: Artificial Sequence
<220> FEATURE:
<223> OTHER INFORMATION: synthetic

<400> SEQUENCE: 168

Thr Lys Asp Lys Asp Ser Ser Gly Tyr Tyr Gly Ile Asp Val
1               5                   10

<210> SEQ ID NO 169
<211> LENGTH: 321
<212> TYPE: DNA
<213> ORGANISM: Artificial Sequence
<220> FEATURE:
<223> OTHER INFORMATION: synthetic

<400> SEQUENCE: 169
gacatccaga tgacccagtc tccatcttcc gtgtctgcat ctgtaggaga cagagtcacc      60
atcacttgtc gggcgagtca gggtattcgc acctggttag cctggtatca gcagaaacca     120
gggaaagccc ctaagctcct gatctatgca gcatccagtt tgcaaagtgg ggtcccatca     180
aggttcagcg gcagtgaatc tgggacagat ttcactctca ccatcagcag cctgcagcct     240
gaagattttg caacttacta ttgtcaacag gctaacagtt tcccattcac tttcggccct     300
gggaccaaag tggatatcaa a                                                321

<210> SEQ ID NO 170
<211> LENGTH: 107
<212> TYPE: PRT
<213> ORGANISM: Artificial Sequence
<220> FEATURE:
<223> OTHER INFORMATION: synthetic

<400> SEQUENCE: 170

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Thr Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: synthetic

<400> SEQUENCE: 171
cagggtattc gcacctgg                                                    18

<210> SEQ ID NO 172
```

```
<211> LENGTH: 6
<212> TYPE: PRT
<213> ORGANISM: Artificial Sequence
<220> FEATURE:
<223> OTHER INFORMATION: synthetic

<400> SEQUENCE: 172

Gln Gly Ile Arg Thr Trp
1               5

<210> SEQ ID NO 173
<211> LENGTH: 9
<212> TYPE: DNA
<213> ORGANISM: Artificial Sequence
<220> FEATURE:
<223> OTHER INFORMATION: synthetic

<400> SEQUENCE: 173 gcagcatcc                                                                  9

<210> SEQ ID NO 174
<211> LENGTH: 3
<212> TYPE: PRT
<213> ORGANISM: Artificial Sequence
<220> FEATURE:
<223> OTHER INFORMATION: synthetic

<400> SEQUENCE: 174

Ala Ala Ser
1

<210> SEQ ID NO 175
<211> LENGTH: 27
<212> TYPE: DNA
<213> ORGANISM: Artificial Sequence
<220> FEATURE:
<223> OTHER INFORMATION: synthetic

<400> SEQUENCE: 175
caacaggcta acagtttccc attcact                                             27

<210> SEQ ID NO 176
<211> LENGTH: 9
<212> TYPE: PRT
<213> ORGANISM: Artificial Sequence
<220> FEATURE:
<223> OTHER INFORMATION: synthetic

<400> SEQUENCE: 176

Gln Gln Ala Asn Ser Phe Pro Phe Thr
1               5

<210> SEQ ID NO 177
<211> LENGTH: 384
<212> TYPE: DNA
<213> ORGANISM: Artificial Sequence
<220> FEATURE:
<223> OTHER INFORMATION: synthetic

<400> SEQUENCE: 177
caggtgcagc tggtggagtc tgggggagac ttggtcaagc ctggagggtc cctgagactc         60
tcctgtgcag cctctggatt caccttcagt gactactaca tgaactggat ccgccaggct        120
ccagggaagg gcctggagtg ggtttcatat attagtagta gtggcagtac catacactac        180
gcagactctg tgaagggccg attcaccatc tccagggaca acgccaagaa tttagtgtat        240
```

```
ctgcgaatga acagcctgag agccgaggac acggccgtat atttctgtgc gagagagaga    300
gaggtccatg actacagtga tccttacttc ttcttctacg gtatggacgt ctggggccaa    360
gggaccacgg tcaccgtctc ctca                                          384
```

<210> SEQ ID NO 178
<211> LENGTH: 128
<212> TYPE: PRT
<213> ORGANISM: Artificial Sequence
<220> FEATURE:
<223> OTHER INFORMATION: synthetic

<400> SEQUENCE: 178

Gln Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Ser Gly Ser Thr Ile His Tyr Ala Asp Ser Val
    50                  55                  60

Lys Gly Arg Phe Thr Ile Ser Arg Asp Asn Ala Lys Asn Leu Val Tyr
65                  70                  75                  80

Leu Arg Met Asn Ser Leu Arg Ala Glu Asp Thr Ala Val Tyr Phe Cys
                85                  90                  95

Ala Arg Glu Arg Glu Val His Asp Tyr Ser Asp Pro Tyr Phe Phe Phe
            100                 105                 110

Tyr Gly Met Asp Val Trp Gly Gln Gly Thr Thr Val Thr Val Ser Ser
        115                 120                 125

<210> SEQ ID NO 179
<211> LENGTH: 24
<212> TYPE: DNA
<213> ORGANISM: Artificial Sequence
<220> FEATURE:
<223> OTHER INFORMATION: synthetic

<400> SEQUENCE: 179

```
ggattcacct tcagtgacta ctac                                          24
```

<210> SEQ ID NO 180
<211> LENGTH: 8
<212> TYPE: PRT
<213> ORGANISM: Artificial Sequence
<220> FEATURE:
<223> OTHER INFORMATION: synthetic

<400> SEQUENCE: 180

Gly Phe Thr Phe Ser Asp Tyr Tyr
1               5

<210> SEQ ID NO 181
<211> LENGTH: 24
<212> TYPE: DNA
<213> ORGANISM: Artificial Sequence
<220> FEATURE:
<223> OTHER INFORMATION: synthetic

<400> SEQUENCE: 181

```
attagtagta gtggcagtac cata                                          24
```

<210> SEQ ID NO 182

<210> SEQ ID NO 182
<211> LENGTH: 8
<212> TYPE: PRT
<213> ORGANISM: Artificial Sequence
<220> FEATURE:
<223> OTHER INFORMATION: synthetic

<400> SEQUENCE: 182

Ile Ser Ser Ser Gly Ser Thr Ile
1               5

<210> SEQ ID NO 183
<211> LENGTH: 63
<212> TYPE: DNA
<213> ORGANISM: Artificial Sequence
<220> FEATURE:
<223> OTHER INFORMATION: synthetic

<400> SEQUENCE: 183
gcgagagaga gagaggtcca tgactacagt gatccttact tcttcttcta cggtatggac    60
gtc                                                                 63

<210> SEQ ID NO 184
<211> LENGTH: 21
<212> TYPE: PRT
<213> ORGANISM: Artificial Sequence
<220> FEATURE:
<223> OTHER INFORMATION: synthetic

<400> SEQUENCE: 184

Ala Arg Glu Arg Glu Val His Asp Tyr Ser Asp Pro Tyr Phe Phe Phe
1               5                   10                  15

Tyr Gly Met Asp Val
            20

<210> SEQ ID NO 185
<211> LENGTH: 321
<212> TYPE: DNA
<213> ORGANISM: Artificial Sequence
<220> FEATURE:
<223> OTHER INFORMATION: synthetic

<400> SEQUENCE: 185
gacatccaga tgacccagtc tccatcttcc gtgtctgcat ctgttggaga cagagtcacc    60
atcacttgtc gggcgagtca ggatgttagc agctggttag cctggtatca acacaaacca   120
gggaaagccc ctaagctcct gatctttgct gcatccagtt tgcaaagtgg ggtcccatca   180
aggttcagcg gcagtggatc tgggacagat ttcactctca ccatcagcag tctgcagtct   240
gaagattttg caacttacta ttgtcaacag gctaacagtt tcccgctcac tttcggcgga   300
gggaccaagg tggagatcaa a                                             321

<210> SEQ ID NO 186
<211> LENGTH: 107
<212> TYPE: PRT
<213> ORGANISM: Artificial Sequence
<220> FEATURE:
<223> OTHER INFORMATION: synthetic

<400> SEQUENCE: 186

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Val Ser Ser Trp
            20                  25                  30

```
Leu Ala Trp Tyr Gln His Lys Pro Gly Lys Ala Pro Lys Leu Leu Ile
             35                  40                  45

Phe Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Ala Thr Tyr Tyr Cys Gln Gln Ala Asn Ser Phe Pro Leu
                 85                  90                  95

Thr Phe Gly Gly Gly Thr Lys Val Glu Ile Lys
            100                 105
```

<210> SEQ ID NO 187
<211> LENGTH: 18
<212> TYPE: DNA
<213> ORGANISM: Artificial Sequence
<220> FEATURE:
<223> OTHER INFORMATION: synthetic

<400> SEQUENCE: 187
caggatgtta gcagctgg                                              18

<210> SEQ ID NO 188
<211> LENGTH: 6
<212> TYPE: PRT
<213> ORGANISM: Artificial Sequence
<220> FEATURE:
<223> OTHER INFORMATION: synthetic

<400> SEQUENCE: 188

```
Gln Asp Val Ser Ser Trp
 1               5
```

<210> SEQ ID NO 189
<211> LENGTH: 9
<212> TYPE: DNA
<213> ORGANISM: Artificial Sequence
<220> FEATURE:
<223> OTHER INFORMATION: synthetic

<400> SEQUENCE: 189 gctgcatcc                                                         9

<210> SEQ ID NO 190
<211> LENGTH: 3
<212> TYPE: PRT
<213> ORGANISM: Artificial Sequence
<220> FEATURE:
<223> OTHER INFORMATION: synthetic

<400> SEQUENCE: 190

```
Ala Ala Ser
 1
```

<210> SEQ ID NO 191
<211> LENGTH: 27
<212> TYPE: DNA
<213> ORGANISM: Artificial Sequence
<220> FEATURE:
<223> OTHER INFORMATION: synthetic

<400> SEQUENCE: 191
caacaggcta acagtttccc gctcact                                    27

<210> SEQ ID NO 192

```
<211> LENGTH: 9
<212> TYPE: PRT
<213> ORGANISM: Artificial Sequence
<220> FEATURE:
<223> OTHER INFORMATION: synthetic

<400> SEQUENCE: 192

Gln Gln Ala Asn Ser Phe Pro Leu Thr
1               5

<210> SEQ ID NO 193
<211> LENGTH: 369
<212> TYPE: DNA
<213> ORGANISM: Artificial Sequence
<220> FEATURE:
<223> OTHER INFORMATION: synthetic

<400> SEQUENCE: 193
caggtgcagc tggtgcagtc tggggctgag gtgaagaagc ctggggcctc agtggaggtc      60
tcctgcaagg cttctggata caccttcacc gactactata tacactggat acgacaggcc     120
cctggacaag ggcttgagtg gatgggatgg atcaaccctg acagtggtcg cacaaactat     180
gcacagaagt tcaggtcag ggtcaccatg accaggaca cgtccatcac cacagcctac       240
atggaactga acagactgaa atctgacgac acggccgtgt attactgtgc gagaggaccc     300
ctacgtggat atagcggcta cgatttttt gactactggg gccagggaac cctggtcacc      360
gtctcctca                                                             369

<210> SEQ ID NO 194
<211> LENGTH: 123
<212> TYPE: PRT
<213> ORGANISM: Artificial Sequence
<220> FEATURE:
<223> OTHER INFORMATION: synthetic

<400> SEQUENCE: 194

Gln Val Gln Leu Val Gln Ser Gly Ala Glu Val Lys Lys Pro Gly Ala
1               5                   10                  15

Ser Val Glu Val Ser Cys Lys Ala Ser Gly Tyr Thr Phe Thr Asp Tyr
            20                  25                  30

Tyr Ile His Trp Ile Arg Gln Ala Pro Gly Gln Gly Leu Glu Trp Met
        35                  40                  45

Gly Trp Ile Asn Pro Asp Ser Gly Arg Thr Asn Tyr Ala Gln Lys Phe
    50                  55                  60

Gln Val Arg Val Thr Met Thr Arg Asp Thr Ser Ile Thr Thr Ala Tyr
65                  70                  75                  80

Met Glu Leu Asn Arg Leu Lys Ser Asp Asp Thr Ala Val Tyr Tyr Cys
                85                  90                  95

Ala Arg Gly Pro Leu Arg Gly Tyr Ser Gly Tyr Asp Phe Phe Asp Tyr
            100                 105                 110

Trp Gly Gln Gly Thr Leu Val Thr Val Ser Ser
        115                 120

<210> SEQ ID NO 195
<211> LENGTH: 24
<212> TYPE: DNA
<213> ORGANISM: Artificial Sequence
<220> FEATURE:
<223> OTHER INFORMATION: synthetic

<400> SEQUENCE: 195
```
ggatacacct tcaccgacta ctat                                           24

<210> SEQ ID NO 196
<211> LENGTH: 8
<212> TYPE: PRT
<213> ORGANISM: Artificial Sequence
<220> FEATURE:
<223> OTHER INFORMATION: synthetic

<400> SEQUENCE: 196

Gly Tyr Thr Phe Thr Asp Tyr Tyr
1               5

<210> SEQ ID NO 197
<211> LENGTH: 24
<212> TYPE: DNA
<213> ORGANISM: Artificial Sequence
<220> FEATURE:
<223> OTHER INFORMATION: synthetic

<400> SEQUENCE: 197
atcaaccctg acagtggtcg caca                                           24

<210> SEQ ID NO 198
<211> LENGTH: 8
<212> TYPE: PRT
<213> ORGANISM: Artificial Sequence
<220> FEATURE:
<223> OTHER INFORMATION: synthetic

<400> SEQUENCE: 198

Ile Asn Pro Asp Ser Gly Arg Thr
1               5

<210> SEQ ID NO 199
<211> LENGTH: 48
<212> TYPE: DNA
<213> ORGANISM: Artificial Sequence
<220> FEATURE:
<223> OTHER INFORMATION: synthetic

<400> SEQUENCE: 199
gcgagaggac ccctacgtgg atatagcggc tacgattttt ttgactac                 48

<210> SEQ ID NO 200
<211> LENGTH: 16
<212> TYPE: PRT
<213> ORGANISM: Artificial Sequence
<220> FEATURE:
<223> OTHER INFORMATION: synthetic

<400> SEQUENCE: 200

Ala Arg Gly Pro Leu Arg Gly Tyr Ser Gly Tyr Asp Phe Phe Asp Tyr
1               5                   10                  15

<210> SEQ ID NO 201
<211> LENGTH: 321
<212> TYPE: DNA
<213> ORGANISM: Artificial Sequence
<220> FEATURE:
<223> OTHER INFORMATION: synthetic

<400> SEQUENCE: 201
gacatccaga tgacccagtc tccatcctcc ctgtctgcat tgtaggaga cagagtcacc     60 atcacttgcc gggcaagtca gagtattagt agttatttaa attggtatca gcagaaacca  120

```
gggaaagccc cgaaactcct gatctatact gcatccactt tgcaaagagg ggtcccatca      180
aggttcagag gcagtgggtc tgggacagat ttcactctca ccatcagcag tctgcaacct      240
gaagattttg caacttacta ttgtcatcag acttacagta tccccatcac cttcggccaa      300
gggacacgac tggagattaa a                                                 321
```

<210> SEQ ID NO 202
<211> LENGTH: 107
<212> TYPE: PRT
<213> ORGANISM: Artificial Sequence
<220> FEATURE:
<223> OTHER INFORMATION: synthetic

<400> SEQUENCE: 202

```
Asp Ile Gln Met Thr Gln Ser Pro Ser Leu Ser Ala Phe Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Thr Ala Ser Thr Leu Gln Arg Gly Val Pro Ser Arg Phe Arg Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Thr Tyr Ser Ile Pro Ile
                85                  90                  95

Thr Phe Gly Gln Gly Thr Arg Leu Glu Ile Lys
            100                 105
```

<210> SEQ ID NO 203
<211> LENGTH: 18
<212> TYPE: DNA
<213> ORGANISM: Artificial Sequence
<220> FEATURE:
<223> OTHER INFORMATION: synthetic

<400> SEQUENCE: 203

```
cagagtatta gtagttat                                                     18
```

<210> SEQ ID NO 204
<211> LENGTH: 6
<212> TYPE: PRT
<213> ORGANISM: Artificial Sequence
<220> FEATURE:
<223> OTHER INFORMATION: synthetic

<400> SEQUENCE: 204

```
Gln Ser Ile Ser Ser Tyr
1               5
```

<210> SEQ ID NO 205
<211> LENGTH: 9
<212> TYPE: DNA
<213> ORGANISM: Artificial Sequence
<220> FEATURE:
<223> OTHER INFORMATION: synthetic

<400> SEQUENCE: 205

```
actgcatcc                                                                9
```

<210> SEQ ID NO 206
<211> LENGTH: 3

```
<212> TYPE: PRT
<213> ORGANISM: Artificial Sequence
<220> FEATURE:
<223> OTHER INFORMATION: synthetic

<400> SEQUENCE: 206

Thr Ala Ser
1

<210> SEQ ID NO 207
<211> LENGTH: 27
<212> TYPE: DNA
<213> ORGANISM: Artificial Sequence
<220> FEATURE:
<223> OTHER INFORMATION: synthetic

<400> SEQUENCE: 207
catcagactt acagtatccc catcacc                                              27

<210> SEQ ID NO 208
<211> LENGTH: 9
<212> TYPE: PRT
<213> ORGANISM: Artificial Sequence
<220> FEATURE:
<223> OTHER INFORMATION: synthetic

<400> SEQUENCE: 208

His Gln Thr Tyr Ser Ile Pro Ile Thr
1               5

<210> SEQ ID NO 209
<211> LENGTH: 369
<212> TYPE: DNA
<213> ORGANISM: Artificial Sequence
<220> FEATURE:
<223> OTHER INFORMATION: synthetic

<400> SEQUENCE: 209
caggtgcagc tggtgcagtc tggggctgag gtgaagaagc ctggggcctc agtggaggtc          60
tcctgcaagg cttctggata caccttcacc gactactata tacactggat acgacaggcc        120
cctggacaag ggcttgagtg gatgggatgg atcaaccctg acgtggtcg cacaaactat         180 gcacagaagt ttcaggtcag ggtcaccatg accagggaca cgtccatcac cacagcctac        240
atggaactga acagactgaa atctgacgac acggccgtgt attactgtgc gagaggaccc        300
ctacgtggat atagcggcta cgatttttt gactactggg gccagggaac cctggtcacc         360
gtctcctca                                                                369

<210> SEQ ID NO 210
<211> LENGTH: 123
<212> TYPE: PRT
<213> ORGANISM: Artificial Sequence
<220> FEATURE:
<223> OTHER INFORMATION: synthetic

<400> SEQUENCE: 210

Gln Val Gln Leu Val Gln Ser Gly Ala Glu Val Lys Lys Pro Gly Ala
1               5                  10                  15

Ser Val Glu Val Ser Cys Lys Ala Ser Gly Tyr Thr Phe Thr Asp Tyr
                20                  25                  30

Tyr Ile His Trp Ile Arg Gln Ala Pro Gly Gln Gly Leu Glu Trp Met
            35                  40                  45

Gly Trp Ile Asn Pro Asp Ser Gly Arg Thr Asn Tyr Ala Gln Lys Phe
```

```
                50                  55                  60
Gln Val Arg Val Thr Met Thr Arg Asp Thr Ser Ile Thr Thr Ala Tyr
 65                  70                  75                  80

Met Glu Leu Asn Arg Leu Lys Ser Asp Thr Ala Val Tyr Tyr Cys
                 85                  90                  95

Ala Arg Gly Pro Leu Arg Gly Tyr Ser Gly Tyr Asp Phe Phe Asp Tyr
            100                 105                 110

Trp Gly Gln Gly Thr Leu Val Thr Val Ser Ser
        115                 120

<210> SEQ ID NO 211
<211> LENGTH: 24
<212> TYPE: DNA
<213> ORGANISM: Artificial Sequence
<220> FEATURE:
<223> OTHER INFORMATION: synthetic

<400> SEQUENCE: 211
ggatacacct tcaccgacta ctat                                          24

<210> SEQ ID NO 212
<211> LENGTH: 8
<212> TYPE: PRT
<213> ORGANISM: Artificial Sequence
<220> FEATURE:
<223> OTHER INFORMATION: synthetic

<400> SEQUENCE: 212

Gly Tyr Thr Phe Thr Asp Tyr Tyr
 1               5

<210> SEQ ID NO 213
<211> LENGTH: 24
<212> TYPE: DNA
<213> ORGANISM: Artificial Sequence
<220> FEATURE:
<223> OTHER INFORMATION: synthetic

<400> SEQUENCE: 213
atcaaccctg acagtggtcg caca                                          24

<210> SEQ ID NO 214
<211> LENGTH: 8
<212> TYPE: PRT
<213> ORGANISM: Artificial Sequence
<220> FEATURE:
<223> OTHER INFORMATION: synthetic

<400> SEQUENCE: 214

Ile Asn Pro Asp Ser Gly Arg Thr
 1               5

<210> SEQ ID NO 215
<211> LENGTH: 48
<212> TYPE: DNA
<213> ORGANISM: Artificial Sequence
<220> FEATURE:
<223> OTHER INFORMATION: synthetic

<400> SEQUENCE: 215
gcgagaggac ccctacgtgg atatagcggc tacgattttt ttgactac                48

<210> SEQ ID NO 216
<211> LENGTH: 16
```

```
<212> TYPE: PRT
<213> ORGANISM: Artificial Sequence
<220> FEATURE:
<223> OTHER INFORMATION: synthetic

<400> SEQUENCE: 216

Ala Arg Gly Pro Leu Arg Gly Tyr Ser Gly Tyr Asp Phe Phe Asp Tyr
1               5                   10                  15

<210> SEQ ID NO 217
<211> LENGTH: 321
<212> TYPE: DNA
<213> ORGANISM: Artificial Sequence
<220> FEATURE:
<223> OTHER INFORMATION: synthetic

<400> SEQUENCE: 217
gacatccaga tgacccagtc tccatcctcc ctgtctgcat ctgtaggaga cagagtcacc     60
atcacttgcc gggcaagtca gggcattaga aatgatttag gctggtatca gcagaaacca    120
gggaaagccc ctaaccgcct gatctatgct gcatccagtt tgcaaagtgg ggtcccatca    180
aggttcagcg gcagtggatc tgggacagaa ttcactctca caatcagcag cctgcatcct    240
gaggattttg caacttattc ctgtctacag cataatagtt tcccgctcac tttcggcggg    300
gggaccaagg tggagatcaa a                                              321

<210> SEQ ID NO 218
<211> LENGTH: 107
<212> TYPE: PRT
<213> ORGANISM: Artificial Sequence
<220> FEATURE:
<223> OTHER INFORMATION: synthetic

<400> SEQUENCE: 218

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Asn Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu His Pro
65                  70                  75                  80

Glu Asp Phe Ala Thr Tyr Ser Cys Leu Gln His Asn Ser Phe Pro Leu
                85                  90                  95

Thr Phe Gly Gly Gly Thr Lys Val Glu Ile Lys
            100                 105

<210> SEQ ID NO 219
<211> LENGTH: 18
<212> TYPE: DNA
<213> ORGANISM: Artificial Sequence
<220> FEATURE:
<223> OTHER INFORMATION: synthetic

<400> SEQUENCE: 219
cagggcatta gaaatgat                                                   18

<210> SEQ ID NO 220
<211> LENGTH: 6
<212> TYPE: PRT
```

```
<213> ORGANISM: Artificial Sequence
<220> FEATURE:
<223> OTHER INFORMATION: synthetic

<400> SEQUENCE: 220

Gln Gly Ile Arg Asn Asp
1               5

<210> SEQ ID NO 221
<211> LENGTH: 9
<212> TYPE: DNA
<213> ORGANISM: Artificial Sequence
<220> FEATURE:
<223> OTHER INFORMATION: synthetic

<400> SEQUENCE: 221 gctgcatcc                                                                   9

<210> SEQ ID NO 222
<211> LENGTH: 3
<212> TYPE: PRT
<213> ORGANISM: Artificial Sequence
<220> FEATURE:
<223> OTHER INFORMATION: synthetic

<400> SEQUENCE: 222

Ala Ala Ser
1

<210> SEQ ID NO 223
<211> LENGTH: 27
<212> TYPE: DNA
<213> ORGANISM: Artificial Sequence
<220> FEATURE:
<223> OTHER INFORMATION: synthetic

<400> SEQUENCE: 223
ctacagcata atagtttccc gctcact                                              27

<210> SEQ ID NO 224
<211> LENGTH: 9
<212> TYPE: PRT
<213> ORGANISM: Artificial Sequence
<220> FEATURE:
<223> OTHER INFORMATION: synthetic

<400> SEQUENCE: 224

Leu Gln His Asn Ser Phe Pro Leu Thr
1               5

<210> SEQ ID NO 225
<211> LENGTH: 380
<212> TYPE: PRT
<213> ORGANISM: Artificial Sequence
<220> FEATURE:
<223> OTHER INFORMATION: synthetic

<400> SEQUENCE: 225

Met Glu Glu Gly Gly Asp Phe Asp Asn Tyr Tyr Gly Ala Asp Asn Gln
1               5                   10                  15

Ser Glu Cys Glu Tyr Thr Asp Trp Lys Ser Ser Gly Ala Leu Ile Pro
            20                  25                  30

Ala Ile Tyr Met Leu Val Phe Leu Leu Gly Thr Thr Gly Asn Gly Leu
        35                  40                  45

Val Leu Trp Thr Val Phe Arg Ser Ser Arg Glu Lys Arg Arg Ser Ala
```

```
                    50                  55                  60
Asp Ile Phe Ile Ala Ser Leu Ala Val Ala Asp Leu Thr Phe Val Val
 65                  70                  75                  80

Thr Leu Pro Leu Trp Ala Thr Thr Tyr Arg Asp Tyr Asp Trp Pro
                 85                  90                  95

Phe Gly Thr Phe Phe Cys Lys Leu Ser Ser Tyr Leu Ile Phe Val Asn
                100                 105                 110

Met Tyr Ala Ser Val Phe Cys Leu Thr Gly Leu Ser Phe Asp Arg Tyr
            115                 120                 125

Leu Ala Ile Val Arg Pro Val Ala Asn Ala Arg Leu Arg Leu Arg Val
            130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
            180                 185                 190

Ser Glu Trp Ala Trp Glu Val Gly Leu Gly Val Ser Ser Thr Thr Val
            195                 200                 205

Gly Phe Val Val Pro Phe Thr Ile Met Leu Thr Cys Tyr Phe Phe Ile
            210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
                260                 265                 270

Leu Gly Ser Leu Leu His Trp Pro Cys Asp Phe Asp Leu Phe Leu Met
            275                 280                 285

Asn Ile Phe Pro Tyr Cys Thr Cys Ile Ser Tyr Val Asn Ser Cys Leu
            290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
            340                 345                 350

Gly Pro Gly Pro Asn Met Gly Lys Gly Gly Glu Gln Met His Glu Lys
            355                 360                 365

Ser Ile Pro Tyr Ser Gln Glu Thr Leu Val Val Asp
            370                 375                 380

<210> SEQ ID NO 226
<211> LENGTH: 380
<212> TYPE: PRT
<213> ORGANISM: Artificial Sequence
<220> FEATURE:
<223> OTHER INFORMATION: synthetic

<400> SEQUENCE: 226

Met Glu Glu Gly Gly Asp Phe Asp Asn Tyr Tyr Gly Ala Asp Asn Gln
 1               5                  10                  15

Ser Glu Cys Glu Tyr Thr Asp Trp Lys Ser Ser Gly Ala Leu Ile Pro
                20                  25                  30

Ala Ile Tyr Met Leu Val Phe Leu Leu Gly Thr Thr Gly Asn Gly Leu
```

```
            35                  40                  45
Val Leu Trp Thr Val Phe Arg Ser Ser Arg Glu Lys Arg Arg Ser Ala
 50                  55                  60

Asp Ile Phe Ile Ala Ser Leu Ala Val Ala Asp Leu Thr Phe Val Val
 65                  70                  75                  80

Thr Leu Pro Leu Trp Ala Thr Tyr Thr Tyr Arg Asp Tyr Asp Trp Pro
                 85                  90                  95

Phe Gly Thr Phe Ser Cys Lys Leu Ser Ser Tyr Leu Ile Phe Val Asn
            100                 105                 110

Met Tyr Ala Ser Val Phe Cys Leu Thr Gly Leu Ser Phe Asp Arg Tyr
        115                 120                 125

Leu Ala Ile Val Arg Pro Val Ala Asn Ala Arg Leu Arg Leu Arg Val
    130                 135                 140

Ser Gly Ala Val Ala Thr Ala Val Leu Trp Val Leu Ala Ala Leu Leu
145                 150                 155                 160

Ala Met Pro Val Met Val Phe Arg Thr Thr Gly Asp Leu Glu Asn Thr
                165                 170                 175

Thr Lys Val Gln Cys Tyr Met Asp Tyr Ser Met Val Ala Thr Val Ser
            180                 185                 190

Ser Asp Trp Ala Trp Glu Val Gly Leu Gly Val Ser Ser Thr Thr Val
        195                 200                 205

Gly Phe Val Val Pro Phe Thr Ile Met Leu Thr Cys Tyr Phe Phe Ile
    210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
            260                 265                 270

Leu Gly Ser Leu Leu His Trp Pro Cys Asp Phe Asp Leu Phe Leu Met
        275                 280                 285

Asn Val Phe Pro Tyr Cys Thr Cys Ile Ser Tyr Val Asn Ser Cys Leu
    290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
            340                 345                 350

Gly Pro Gly Pro Asn Met Gly Lys Gly Gly Glu Gln Met His Glu Lys
        355                 360                 365

Ser Ile Pro Tyr Ser Gln Glu Thr Leu Val Val Asp
    370                 375                 380

<210> SEQ ID NO 227
<211> LENGTH: 77
<212> TYPE: PRT
<213> ORGANISM: Artificial Sequence
<220> FEATURE:
<223> OTHER INFORMATION: synthetic

<400> SEQUENCE: 227

Met Asn Leu Arg Leu Cys Val Gln Ala Leu Leu Leu Leu Trp Leu Ser
 1               5                  10                  15

Leu Thr Ala Val Cys Gly Gly Ser Leu Met Pro Leu Pro Asp Gly Asn
```

```
            20                  25                  30

Gly Leu Glu Asp Gly Asn Val Arg His Leu Val Gln Pro Arg Gly Ser
            35                  40                  45

Arg Asn Gly Pro Gly Pro Trp Gln Gly Gly Arg Lys Phe Arg Arg
        50                  55                  60

Gln Arg Pro Arg Leu Ser His Lys Gly Pro Met Pro Phe
65                  70                  75
```

<210> SEQ ID NO 228
<211> LENGTH: 13
<212> TYPE: PRT
<213> ORGANISM: Artificial Sequence
<220> FEATURE:
<223> OTHER INFORMATION: synthetic

<400> SEQUENCE: 228

```
Gln Arg Pro Arg Leu Ser His Lys Gly Pro Met Pro Phe
1               5                   10
```

<210> SEQ ID NO 229
<211> LENGTH: 17
<212> TYPE: PRT
<213> ORGANISM: Artificial Sequence
<220> FEATURE:
<223> OTHER INFORMATION: synthetic

<400> SEQUENCE: 229

```
Lys Phe Arg Arg Gln Arg Pro Arg Leu Ser His Lys Gly Pro Met Pro
1               5                   10                  15

Phe
```

<210> SEQ ID NO 230
<211> LENGTH: 36
<212> TYPE: PRT
<213> ORGANISM: Artificial Sequence
<220> FEATURE:
<223> OTHER INFORMATION: synthetic

<400> SEQUENCE: 230

```
Leu Val Gln Pro Arg Gly Ser Arg Asn Gly Pro Gly Pro Trp Gln Gly
1               5                   10                  15

Gly Arg Arg Lys Phe Arg Arg Gln Arg Pro Arg Leu Ser His Lys Gly
            20                  25                  30

Pro Met Pro Phe
        35
```

<210> SEQ ID NO 231
<211> LENGTH: 5
<212> TYPE: PRT
<213> ORGANISM: Artificial Sequence
<220> FEATURE:
<223> OTHER INFORMATION: synthetic

<400> SEQUENCE: 231

```
Gly Gly Gly Gly Ser
1               5
```

<210> SEQ ID NO 232
<211> LENGTH: 10
<212> TYPE: PRT
<213> ORGANISM: Artificial Sequence
<220> FEATURE:
<223> OTHER INFORMATION: synthetic

```
<400> SEQUENCE: 232

Gly Gly Gly Gly Ser Gly Gly Gly Ser
1               5                   10

<210> SEQ ID NO 233
<211> LENGTH: 15
<212> TYPE: PRT
<213> ORGANISM: Artificial Sequence
<220> FEATURE:
<223> OTHER INFORMATION: synthetic

<400> SEQUENCE: 233

Gly Gly Gly Gly Ser Gly Gly Gly Ser Gly Gly Gly Ser
1               5                   10                  15

<210> SEQ ID NO 234
<211> LENGTH: 420
<212> TYPE: DNA
<213> ORGANISM: Artificial Sequence
<220> FEATURE:
<223> OTHER INFORMATION: synthetic

<400> SEQUENCE: 234
caaagaccaa gactttcaca caaaggacct atgccattcg gtggtggtgg aagcggaggg      60
ggaggatctg gaggtggtgg atcagacatc gtgatgaccc agtctccaga ctccctggct     120
gtgtctctgg gcgagagggc caccatcaac tgcaagtcca gccagagtgt tttatacacc     180
tccaacaata gaaactactt agcttggtac cagcagaaac caggacagcc tcctaaactg     240
ctcatttact gggcatctac ccgggaatcc ggggtccctg accgattcag tggcagcggg     300
tctgggacag atttcactct caccatcagc agcctgcagg ctgaagatgt ggcagtttat     360
tactgtcagc aatattatag tacttacact tttggccagg ggaccaagct ggagatcaaa     420

<210> SEQ ID NO 235
<211> LENGTH: 140
<212> TYPE: PRT
<213> ORGANISM: Artificial Sequence
<220> FEATURE:
<223> OTHER INFORMATION: synthetic

<400> SEQUENCE: 235

Gln Arg Pro Arg Leu Ser His Lys Gly Pro Met Pro Phe Gly Gly Gly
1               5                   10                  15

Gly Ser Gly Gly Gly Gly Ser Gly Gly Gly Gly Ser Asp Ile Val Met
                20                  25                  30

Thr Gln Ser Pro Asp Ser Leu Ala Val Ser Leu Gly Glu Arg Ala Thr
            35                  40                  45

Ile Asn Cys Lys Ser Ser Gln Ser Val Leu Tyr Thr Ser Asn Asn Lys
        50                  55                  60

Asn Tyr Leu Ala Trp Tyr Gln Gln Lys Pro Gly Gln Pro Pro Lys Leu
65                  70                  75                  80

Leu Ile Tyr Trp Ala Ser Thr Arg Glu Ser Gly Val Pro Asp Arg Phe
                85                  90                  95

Ser Gly Ser Gly Ser Gly Thr Asp Phe Thr Leu Thr Ile Ser Ser Leu
            100                 105                 110

Gln Ala Glu Asp Val Ala Val Tyr Tyr Cys Gln Gln Tyr Tyr Ser Thr
        115                 120                 125

Tyr Thr Phe Gly Gln Gly Thr Lys Leu Glu Ile Lys
    130                 135                 140
```

<210> SEQ ID NO 236
<211> LENGTH: 744
<212> TYPE: DNA
<213> ORGANISM: Artificial Sequence
<220> FEATURE:
<223> OTHER INFORMATION: synthetic

<400> SEQUENCE: 236

```
gacatcgtga tgacccagtc tccagactcc ctggctgtgt ctctgggcga gagggccacc      60
atcaactgca agtccagcca gagtgtttta tacacctcca acaataagaa ctacttagct     120
tggtaccagc agaaaccagg acagcctcct aaactgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtact     300
tacactttg gccaggggac caagctggag atcaaacgaa ctgtggctgc accatctgtc      360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgtgga     660
ggtggtggat caggaggagg gggctccggg ggaggaggta gccaaagacc acgattgtct     720
cacaaaggac caatgccatt ttaa                                            744
```

<210> SEQ ID NO 237
<211> LENGTH: 247
<212> TYPE: PRT
<213> ORGANISM: Artificial Sequence
<220> FEATURE:
<223> OTHER INFORMATION: synthetic

<400> SEQUENCE: 237

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Thr
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Gly Gly Gly Gly Ser
        210                 215                 220

Gly Gly Gly Gly Ser Gly Gly Gly Ser Gln Arg Pro Arg Leu Ser
225                 230                 235                 240

His Lys Gly Pro Met Pro Phe
                245
```

<210> SEQ ID NO 238
<211> LENGTH: 453
<212> TYPE: DNA
<213> ORGANISM: Artificial Sequence
<220> FEATURE:
<223> OTHER INFORMATION: synthetic

<400> SEQUENCE: 238

```
caaagaccaa gactttcaca caaaggacct atgccattcg gtggtggtgg aagcggaggg      60
ggaggatctg gaggtggtgg atcagaggtg cagctggtgg agtctggggg aggcttggta     120
aagcctgggg ggtcccttag actctcctgt gcagcctctg gaatcacttt cagtaacgcc     180
tggatgagct gggtccgcca ggctccaggg aaggggctgg agtgggttgg ccgttttaaa     240
ggcaaagctg atggtgggac agttgactat gctgcacccg tgaaaggcag attcaccatc     300
tcaagagatg attcgaaaaa cacgctgtat ctgcaaatga acagtctgaa aaacgaggac     360
acagccgtgt attactgcac cacaggtcga attactatgg ttcggggagt tttgggctac     420
tggggccagg gaaccctggt cacygtctcc tca                                  453
```

<210> SEQ ID NO 239
<211> LENGTH: 151
<212> TYPE: PRT
<213> ORGANISM: Artificial Sequence
<220> FEATURE:
<223> OTHER INFORMATION: synthetic

<400> SEQUENCE: 239

```
Gln Arg Pro Arg Leu Ser His Lys Gly Pro Met Pro Phe Gly Gly Gly
1               5                   10                  15

Gly Ser Gly Gly Gly Gly Ser Gly Gly Gly Gly Ser Glu Val Gln Leu
            20                  25                  30

Val Glu Ser Gly Gly Gly Leu Val Lys Pro Gly Gly Ser Leu Arg Leu
        35                  40                  45

Ser Cys Ala Ala Ser Gly Ile Thr Phe Ser Asn Ala Trp Met Ser Trp
    50                  55                  60

Val Arg Gln Ala Pro Gly Lys Gly Leu Glu Trp Val Gly Arg Phe Lys
65                  70                  75                  80

Gly Lys Ala Asp Gly Gly Thr Val Asp Tyr Ala Ala Pro Val Lys Gly
                85                  90                  95

Arg Phe Thr Ile Ser Arg Asp Asp Ser Lys Asn Thr Leu Tyr Leu Gln
            100                 105                 110

Met Asn Ser Leu Lys Asn Glu Asp Thr Ala Val Tyr Tyr Cys Thr Thr
        115                 120                 125

Gly Arg Ile Thr Met Val Arg Gly Val Leu Gly Tyr Trp Gly Gln Gly
    130                 135                 140

Thr Leu Val Thr Val Ser Ser
```

<210> SEQ ID NO 240
<211> LENGTH: 408
<212> TYPE: DNA
<213> ORGANISM: Artificial Sequence
<220> FEATURE:
<223> OTHER INFORMATION: synthetic

<400> SEQUENCE: 240

```
caaagaccaa gactttcaca caaaggacct atgcccttcg aggtgcagct ggtggagtct    60
ggggggaggct tggtaaagcc tgggggggtcc cttagactct cctgtgcagc ctctggaatc   120
actttcagta acgcctggat gagctgggtc cgccaggctc cagggaaggg gctggagtgg   180
gttggccgtt ttaaaggcaa agctgatggt gggacagttg actatgctgc acccgtgaaa   240
ggcagattca ccatctcaag agatgattcg aaaaacacgc tgtatctgca aatgaacagt   300
ctgaaaaacg aggacacagc cgtgtattac tgcaccacag gtcgaattac tatggttcgg   360
ggagttttgg gctactgggg ccagggaacc ctggtcacyg tctcctca              408
```

<210> SEQ ID NO 241
<211> LENGTH: 136
<212> TYPE: PRT
<213> ORGANISM: Artificial Sequence
<220> FEATURE:
<223> OTHER INFORMATION: synthetic

<400> SEQUENCE: 241

```
Gln Arg Pro Arg Leu Ser His Lys Gly Pro Met Pro Phe Glu Val Gln
1               5                   10                  15
Leu Val Glu Ser Gly Gly Gly Leu Val Lys Pro Gly Gly Ser Leu Arg
            20                  25                  30
Leu Ser Cys Ala Ala Ser Gly Ile Thr Phe Ser Asn Ala Trp Met Ser
        35                  40                  45
Trp Val Arg Gln Ala Pro Gly Lys Gly Leu Glu Trp Val Gly Arg Phe
    50                  55                  60
Lys Gly Lys Ala Asp Gly Gly Thr Val Asp Tyr Ala Ala Pro Val Lys
65                  70                  75                  80
Gly Arg Phe Thr Ile Ser Arg Asp Asp Ser Lys Asn Thr Leu Tyr Leu
                85                  90                  95
Gln Met Asn Ser Leu Lys Asn Glu Asp Thr Ala Val Tyr Tyr Cys Thr
            100                 105                 110
Thr Gly Arg Ile Thr Met Val Arg Gly Val Leu Gly Tyr Trp Gly Gln
        115                 120                 125
Gly Thr Leu Val Thr Val Ser Ser
    130                 135
```

<210> SEQ ID NO 242
<211> LENGTH: 423
<212> TYPE: DNA
<213> ORGANISM: Artificial Sequence
<220> FEATURE:
<223> OTHER INFORMATION: synthetic

<400> SEQUENCE: 242

```
caaagaccaa gactctcaca taaaggtcca atgcccttcg gtggtggcgg gtccgaggtg    60
cagctggtgg agtctggggg aggcttggta aagcctgggg gtcccttag actctcctgt   120
gcagcctctg gaatcacttt cagtaacgcc tggatgagct gggtccgcca ggctccaggg   180
``` aagggctgg agtgggttgg ccgttttaaa ggcaaagctg atggtgggac agttgactat    240
gctgcacccg tgaaaggcag attcaccatc tcaagagatg attcgaaaaa cacgctgtat    300
ctgcaaatga acagtctgaa aaacgaggac acagccgtgt attactgcac cacaggtcga    360
attactatgg ttcggggagt tttgggctac tggggccagg gaaccctggt cacygtctcc    420
tca    423

<210> SEQ ID NO 243
<211> LENGTH: 141
<212> TYPE: PRT
<213> ORGANISM: Artificial Sequence
<220> FEATURE:
<223> OTHER INFORMATION: synthetic

<400> SEQUENCE: 243

Gln Arg Pro Arg Leu Ser His Lys Gly Pro Met Pro Phe Gly Gly Gly
1               5                   10                  15

Gly Ser Glu Val Gln Leu Val Glu Ser Gly Gly Gly Leu Val Lys Pro
            20                  25                  30

Gly Gly Ser Leu Arg Leu Ser Cys Ala Ala Ser Gly Ile Thr Phe Ser
        35                  40                  45

Asn Ala Trp Met Ser Trp Val Arg Gln Ala Pro Gly Lys Gly Leu Glu
    50                  55                  60

Trp Val Gly Arg Phe Lys Gly Lys Ala Asp Gly Gly Thr Val Asp Tyr
65                  70                  75                  80

Ala Ala Pro Val Lys Gly Arg Phe Thr Ile Ser Arg Asp Asp Ser Lys
                85                  90                  95

Asn Thr Leu Tyr Leu Gln Met Asn Ser Leu Lys Asn Glu Asp Thr Ala
            100                 105                 110

Val Tyr Tyr Cys Thr Thr Gly Arg Ile Thr Met Val Arg Gly Val Leu
        115                 120                 125

Gly Tyr Trp Gly Gln Gly Thr Leu Val Thr Val Ser Ser
    130                 135                 140

<210> SEQ ID NO 244
<211> LENGTH: 438
<212> TYPE: DNA
<213> ORGANISM: Artificial Sequence
<220> FEATURE:
<223> OTHER INFORMATION: synthetic

<400> SEQUENCE: 244
caaagaccta gactttcaca taaaggaccc atgcccttcg gaggaggagg atctggaggc    60
ggaggttctg aggtgcagct ggtggagtct gggggaggct tggtaaagcc tgggggtcc    120 cttagactct cctgtgcagc ctctggaatc actttcagta acgcctggat gagctgggtc    180
cgccaggctc cagggaaggg gctggagtgg gttggccgtt ttaaaggcaa agctgatggt    240
gggacagttg actatgctgc acccgtgaaa ggcagattca ccatctcaag agatgattcg    300
aaaaacacgc tgtatctgca aatgaacagt ctgaaaaacg aggacacagc cgtgtattac    360
tgcaccacag gtcgaattac tatggttcgg ggagttttgg gctactgggg ccagggaacc    420
ctggtcacyg tctcctca    438

<210> SEQ ID NO 245
<211> LENGTH: 146
<212> TYPE: PRT
<213> ORGANISM: Artificial Sequence
<220> FEATURE:

<223> OTHER INFORMATION: synthetic

<400> SEQUENCE: 245

Gln Arg Pro Arg Leu Ser His Lys Gly Pro Met Pro Phe Gly Gly Gly
1               5                   10                  15

Gly Ser Gly Gly Gly Ser Glu Val Gln Leu Val Glu Ser Gly Gly
            20                  25                  30

Gly Leu Val Lys Pro Gly Gly Ser Leu Arg Leu Ser Cys Ala Ala Ser
            35                  40                  45

Gly Ile Thr Phe Ser Asn Ala Trp Met Ser Trp Val Arg Gln Ala Pro
        50                  55                  60

Gly Lys Gly Leu Glu Trp Val Gly Arg Phe Lys Gly Lys Ala Asp Gly
65                  70                  75                  80

Gly Thr Val Asp Tyr Ala Ala Pro Val Lys Gly Arg Phe Thr Ile Ser
                85                  90                  95

Arg Asp Asp Ser Lys Asn Thr Leu Tyr Leu Gln Met Asn Ser Leu Lys
            100                 105                 110

Asn Glu Asp Thr Ala Val Tyr Tyr Cys Thr Thr Gly Arg Ile Thr Met
        115                 120                 125

Val Arg Gly Val Leu Gly Tyr Trp Gly Gln Gly Thr Leu Val Thr Val
    130                 135                 140

Ser Ser
145

<210> SEQ ID NO 246
<211> LENGTH: 453
<212> TYPE: DNA
<213> ORGANISM: Artificial Sequence
<220> FEATURE:
<223> OTHER INFORMATION: synthetic

<400> SEQUENCE: 246
caaagaccaa gactttcaca caaaggacct atgccattcg gtggtggtgg aagcggaggg      60
ggaggatctg gaggtggtgg atcagaggtg cagctggtgg agtctggggg aggcttggta     120
aaacctgggg ggtcccttag actctcctgt gcagcctctg gaatcacttt cagtaacgcc     180
tggatgagct gggtccgcca ggctccaggg aaggggctgg agtgggttgg ccgtattaaa     240
agcaaagttg atggtgggac aatagactac gctgcacccg tgaaaggcag attcaccatc     300
tcaagagatg attcaaaaaa cacgctgtat ctgcaaatga acagcctgaa aaccgaggac     360
acagccgttt attactgtac cacaggtcga attactatgg ttcggggagt tttgggctac     420
tggggccagg gaaccctggt cactgtctcc tca                                  453

<210> SEQ ID NO 247
<211> LENGTH: 151
<212> TYPE: PRT
<213> ORGANISM: Artificial Sequence
<220> FEATURE:
<223> OTHER INFORMATION: synthetic

<400> SEQUENCE: 247

Gln Arg Pro Arg Leu Ser His Lys Gly Pro Met Pro Phe Gly Gly Gly
1               5                   10                  15

Gly Ser Gly Gly Gly Gly Ser Gly Gly Gly Ser Glu Val Gln Leu
            20                  25                  30

Val Glu Ser Gly Gly Gly Leu Val Lys Pro Gly Gly Ser Leu Arg Leu
        35                  40                  45

```
Ser Cys Ala Ala Ser Gly Ile Thr Phe Ser Asn Ala Trp Met Ser Trp
 50                  55                  60

Val Arg Gln Ala Pro Gly Lys Gly Leu Glu Trp Val Gly Arg Ile Lys
 65                  70                  75                  80

Ser Lys Val Asp Gly Gly Thr Ile Asp Tyr Ala Ala Pro Val Lys Gly
                 85                  90                  95

Arg Phe Thr Ile Ser Arg Asp Asp Ser Lys Asn Thr Leu Tyr Leu Gln
                100                 105                 110

Met Asn Ser Leu Lys Thr Glu Asp Thr Ala Val Tyr Tyr Cys Thr Thr
                115                 120                 125

Gly Arg Ile Thr Met Val Arg Gly Val Leu Gly Tyr Trp Gly Gln Gly
                130                 135                 140

Thr Leu Val Thr Val Ser Ser
145                 150

<210> SEQ ID NO 248
<211> LENGTH: 420
<212> TYPE: DNA
<213> ORGANISM: Artificial Sequence
<220> FEATURE:
<223> OTHER INFORMATION: synthetic

<400> SEQUENCE: 248
caaagaccaa gactttcaca caaaggacct atgccattcg gtggtggtgg aagcggaggg      60
ggaggatctg gaggtggtgg atcagacatc gtgatgaccc agtctccaga ctccctggct     120
gtgtctctgg gcgagagggc caccatcaac tgcaagtcca gccagagtgt tttatacagc     180
tccaacaata gaactactt agcttggtac cagcagaaac aggacagcc tcctaagctg      240 ctcatttact gggcatctac ccgggaatcc ggggtccctg accgattcag tggcagcggg     300
tctgggacag atttcactct caccatcagc agcctgcagg ctgaagatgt ggctgtttat     360
tactgtcagc aatattatag tacttacact tttggccagg ggaccaagct ggagatcaaa     420

<210> SEQ ID NO 249
<211> LENGTH: 140
<212> TYPE: PRT
<213> ORGANISM: Artificial Sequence
<220> FEATURE:
<223> OTHER INFORMATION: synthetic

<400> SEQUENCE: 249

Gln Arg Pro Arg Leu Ser His Lys Gly Pro Met Pro Phe Gly Gly Gly
  1               5                  10                  15

Gly Ser Gly Gly Gly Gly Ser Gly Gly Gly Gly Ser Asp Ile Val Met
                 20                  25                  30

Thr Gln Ser Pro Asp Ser Leu Ala Val Ser Leu Gly Glu Arg Ala Thr
             35                  40                  45

Ile Asn Cys Lys Ser Ser Gln Ser Val Leu Tyr Ser Ser Asn Asn Lys
 50                  55                  60

Asn Tyr Leu Ala Trp Tyr Gln Gln Lys Pro Gly Gln Pro Pro Lys Leu
 65                  70                  75                  80

Leu Ile Tyr Trp Ala Ser Thr Arg Glu Ser Gly Val Pro Asp Arg Phe
                 85                  90                  95

Ser Gly Ser Gly Ser Gly Thr Asp Phe Thr Leu Thr Ile Ser Ser Leu
                100                 105                 110

Gln Ala Glu Asp Val Ala Val Tyr Tyr Cys Gln Gln Tyr Tyr Ser Thr
                115                 120                 125
```

Tyr Thr Phe Gly Gln Gly Thr Lys Leu Glu Ile Lys
            130                 135                 140

<210> SEQ ID NO 250
<211> LENGTH: 744
<212> TYPE: DNA
<213> ORGANISM: Artificial Sequence
<220> FEATURE:
<223> OTHER INFORMATION: synthetic

<400> SEQUENCE: 250

```
gacatcgtga tgacccagtc tccagactcc ctggctgtgt ctctgggcga gagggccacc      60
atcaactgca gtccagcca gagtgtttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggct gtttattact gtcagcaata ttatagtact     300
tacactttg gccaggggac caagctggag atcaaacgaa ctgtggctgc accatctgtc      360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgtgga     660
ggtggtggat caggaggagg gggctccggg ggaggaggta gccaaagacc acgattgtct     720
cacaaaggac caatgccatt ttaa                                            744
```

<210> SEQ ID NO 251
<211> LENGTH: 247
<212> TYPE: PRT
<213> ORGANISM: Artificial Sequence
<220> FEATURE:
<223> OTHER INFORMATION: synthetic

<400> SEQUENCE: 251

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Gln Arg Pro Arg Leu Ser
225                 230                 235                 240

His Lys Gly Pro Met Pro Phe
                245

<210> SEQ ID NO 252
<211> LENGTH: 381
<212> TYPE: DNA
<213> ORGANISM: Artificial Sequence
<220> FEATURE:
<223> OTHER INFORMATION: synthetic

<400> SEQUENCE: 252
caaagaccaa gactttcaca caaaggacct atgcccttcg aggtgcagct gttggagtct     60
gggggaggct tggttcagcc tggggggtcc ctgagactct cctgtgcagc ctctggattc    120
acctttagca actatgccat gaactgggtc cgccaggctc agggaggggg ctggagtgg    180 gtctcagcta ttcattatga tggtagtaat tcatattacg cagactccgt gaagggccgg    240
ttcaccatct ccagagacaa ttccaagaac acgctgtatc tgcaaatgaa cagcctgaga    300
gccgaagaca cggccattta ttactgtgcg atattgtcaa gggtctactg gggccaggga    360
accctggtca ccgtctcctc a                                              381

<210> SEQ ID NO 253
<211> LENGTH: 127
<212> TYPE: PRT
<213> ORGANISM: Artificial Sequence
<220> FEATURE:
<223> OTHER INFORMATION: synthetic

<400> SEQUENCE: 253

Gln Arg Pro Arg Leu Ser His Lys Gly Pro Met Pro Phe Glu Val Gln
1               5                   10                  15

Leu Leu Glu Ser Gly Gly Gly Leu Val Gln Pro Gly Gly Ser Leu Arg
            20                  25                  30

Leu Ser Cys Ala Ala Ser Gly Phe Thr Phe Ser Asn Tyr Ala Met Asn
        35                  40                  45

Trp Val Arg Gln Ala Pro Gly Arg Gly Leu Glu Trp Val Ser Ala Ile
    50                  55                  60

His Tyr Asp Gly Ser Asn Ser Tyr Tyr Ala Asp Ser Val Lys Gly Arg
65                  70                  75                  80

Phe Thr Ile Ser Arg Asp Asn Ser Lys Asn Thr Leu Tyr Leu Gln Met
                85                  90                  95

Asn Ser Leu Arg Ala Glu Asp Thr Ala Ile Tyr Tyr Cys Ala Ile Leu
            100                 105                 110

Ser Arg Val Tyr Trp Gly Gln Gly Thr Leu Val Thr Val Ser Ser
        115                 120                 125

<210> SEQ ID NO 254
<211> LENGTH: 396

<212> TYPE: DNA
<213> ORGANISM: Artificial Sequence
<220> FEATURE:
<223> OTHER INFORMATION: synthetic

<400> SEQUENCE: 254

| | | | | | |
|---|---|---|---|---|---|
| caaagaccaa | gactctcaca | taaaggtcca | atgcccttcg | gtggtggcgg | gtctgaggtg | 60 |
| cagctgttgg | agtctggggg | aggcttggtt | cagcctgggg | ggtccctgag | actctcctgt | 120 |
| gcagcctctg | gattcacctt | tagcaactat | gccatgaact | gggtccgcca | ggctccaggg | 180 |
| aggggggctgg | agtgggtctc | agctattcat | tatgatggta | gtaattcata | ttacgcagac | 240 |
| tccgtgaagg | gccggttcac | catctccaga | gacaattcca | agaacacgct | gtatctgcaa | 300 |
| atgaacagcc | tgagagccga | agacacggcc | atttattact | gtgcgatatt | gtcaagggtc | 360 |
| tactggggcc | agggaaccct | ggtcaccgtc | tcctca | | | 396 |

<210> SEQ ID NO 255
<211> LENGTH: 132
<212> TYPE: PRT
<213> ORGANISM: Artificial Sequence
<220> FEATURE:
<223> OTHER INFORMATION: synthetic

<400> SEQUENCE: 255

Gln Arg Pro Arg Leu Ser His Lys Gly Pro Met Pro Phe Gly Gly Gly
1               5                   10                  15
Gly Ser Glu Val Gln Leu Leu Glu Ser Gly Gly Gly Leu Val Gln Pro
            20                  25                  30
Gly Gly Ser Leu Arg Leu Ser Cys Ala Ala Ser Gly Phe Thr Phe Ser
        35                  40                  45
Asn Tyr Ala Met Asn Trp Val Arg Gln Ala Pro Gly Arg Gly Leu Glu
    50                  55                  60
Trp Val Ser Ala Ile His Tyr Asp Gly Ser Asn Ser Tyr Tyr Ala Asp
65                  70                  75                  80
Ser Val Lys Gly Arg Phe Thr Ile Ser Arg Asp Asn Ser Lys Asn Thr
                85                  90                  95
Leu Tyr Leu Gln Met Asn Ser Leu Arg Ala Glu Asp Thr Ala Ile Tyr
            100                 105                 110
Tyr Cys Ala Ile Leu Ser Arg Val Tyr Trp Gly Gln Gly Thr Leu Val
        115                 120                 125
Thr Val Ser Ser
    130

<210> SEQ ID NO 256
<211> LENGTH: 411
<212> TYPE: DNA
<213> ORGANISM: Artificial Sequence
<220> FEATURE:
<223> OTHER INFORMATION: synthetic

<400> SEQUENCE: 256

| | | | | | |
|---|---|---|---|---|---|
| caaagaccta | gactttcaca | taaaggaccc | atgcccttcg | gaggaggagg | atctggaggc | 60 |
| ggaggttctg | aggtgcagct | gttggagtct | gggggaggct | tggttcagcc | tggggggtcc | 120 |
| ctgagactct | cctgtgcagc | ctctggattc | acctttagca | actatgccat | gaactgggtc | 180 |
| cgccaggctc | cagggagggg | gctggagtgg | gtctcagcta | ttcattatga | tggtagtaat | 240 |
| tcatattacg | cagactccgt | gaagggccgg | ttcaccatct | ccagagacaa | ttccaagaac | 300 |
| acgctgtatc | tgcaaatgaa | cagcctgaga | gccgaagaca | cggccattta | ttactgtgcg | 360 |

```
atattgtcaa gggtctactg gggccaggga accctggtca ccgtctcctc a           411
```

<210> SEQ ID NO 257
<211> LENGTH: 137
<212> TYPE: PRT
<213> ORGANISM: Artificial Sequence
<220> FEATURE:
<223> OTHER INFORMATION: synthetic

<400> SEQUENCE: 257

```
Gln Arg Pro Arg Leu Ser His Lys Gly Pro Met Pro Phe Gly Gly Gly
1               5                   10                  15

Gly Ser Gly Gly Gly Gly Ser Glu Val Gln Leu Leu Glu Ser Gly Gly
            20                  25                  30

Gly Leu Val Gln Pro Gly Gly Ser Leu Arg Leu Ser Cys Ala Ala Ser
        35                  40                  45

Gly Phe Thr Phe Ser Asn Tyr Ala Met Asn Trp Val Arg Gln Ala Pro
    50                  55                  60

Gly Arg Gly Leu Glu Trp Val Ser Ala Ile His Tyr Asp Gly Ser Asn
65                  70                  75                  80

Ser Tyr Tyr Ala Asp Ser Val Lys Gly Arg Phe Thr Ile Ser Arg Asp
                85                  90                  95

Asn Ser Lys Asn Thr Leu Tyr Leu Gln Met Asn Ser Leu Arg Ala Glu
            100                 105                 110

Asp Thr Ala Ile Tyr Tyr Cys Ala Ile Leu Ser Arg Val Tyr Trp Gly
        115                 120                 125

Gln Gly Thr Leu Val Thr Val Ser Ser
    130                 135
```

<210> SEQ ID NO 258
<211> LENGTH: 426
<212> TYPE: DNA
<213> ORGANISM: Artificial Sequence
<220> FEATURE:
<223> OTHER INFORMATION: synthetic

<400> SEQUENCE: 258

```
caaagaccaa gactttcaca caaaggacct atgccattcg gtggtggtgg aagcggaggg    60
ggaggatctg gaggtggtgg atcagaggtg cagctgttgg agtctggggg aggcttggtt   120
cagcctgggg ggtccctgag actctcctgt gcagcctctg gattcacctt tagcaactat   180
gccatgaact gggtccgcca ggctccaggg aggggggctgg agtgggtctc agctattcat   240
tatgatggta gtaattcata ttacgcagac tccgtgaagg gccggttcac catctccaga   300
gacaattcca agaacacgct gtatctgcaa atgaacagcc tgagagccga agacacggcc   360
atttattact gtgcgatatt gtcaagggtc tactggggcc agggaaccct ggtcaccgtc   420
tcctca                                                              426
```

<210> SEQ ID NO 259
<211> LENGTH: 142
<212> TYPE: PRT
<213> ORGANISM: Artificial Sequence
<220> FEATURE:
<223> OTHER INFORMATION: synthetic

<400> SEQUENCE: 259

```
Gln Arg Pro Arg Leu Ser His Lys Gly Pro Met Pro Phe Gly Gly Gly
1               5                   10                  15
```

Gly Ser Gly Gly Gly Ser Gly Gly Ser Glu Val Gln Leu
            20                  25                  30

Leu Glu Ser Gly Gly Leu Val Gln Pro Gly Ser Leu Arg Leu
            35                  40                  45

Ser Cys Ala Ala Ser Gly Phe Thr Phe Ser Asn Tyr Ala Met Asn Trp
 50                  55                  60

Val Arg Gln Ala Pro Gly Arg Gly Leu Glu Trp Val Ser Ala Ile His
 65                  70                  75                  80

Tyr Asp Gly Ser Asn Ser Tyr Tyr Ala Asp Ser Val Lys Gly Arg Phe
                85                  90                  95

Thr Ile Ser Arg Asp Asn Ser Lys Asn Thr Leu Tyr Leu Gln Met Asn
            100                 105                 110

Ser Leu Arg Ala Glu Asp Thr Ala Ile Tyr Tyr Cys Ala Ile Leu Ser
            115                 120                 125

Arg Val Tyr Trp Gly Gln Gly Thr Leu Val Thr Val Ser Ser
            130                 135                 140

<210> SEQ ID NO 260
<211> LENGTH: 14
<212> TYPE: PRT
<213> ORGANISM: Artificial Sequence
<220> FEATURE:
<223> OTHER INFORMATION: synthetic

<400> SEQUENCE: 260

Pro Gln Arg Pro Arg Leu Ser His Lys Gly Pro Met Pro Ala
1               5                   10

<210> SEQ ID NO 261
<211> LENGTH: 13
<212> TYPE: PRT
<213> ORGANISM: Artificial Sequence
<220> FEATURE:
<223> OTHER INFORMATION: synthetic

<400> SEQUENCE: 261

Pro Gln Arg Pro Arg Leu Ser His Lys Gly Pro Met Pro
1               5                   10

<210> SEQ ID NO 262
<211> LENGTH: 12
<212> TYPE: PRT
<213> ORGANISM: Artificial Sequence
<220> FEATURE:
<223> OTHER INFORMATION: synthetic

<400> SEQUENCE: 262

Pro Gln Arg Pro Arg Leu Ser His Lys Gly Pro Met
1               5                   10

<210> SEQ ID NO 263
<211> LENGTH: 13
<212> TYPE: PRT
<213> ORGANISM: Artificial Sequence
<220> FEATURE:
<223> OTHER INFORMATION: synthetic

<400> SEQUENCE: 263

Pro Arg Pro Arg Leu Ser His Lys Gly Pro Met Pro Phe
1               5                   10

<210> SEQ ID NO 264
<211> LENGTH: 12

<212> TYPE: PRT
<213> ORGANISM: Artificial Sequence
<220> FEATURE:
<223> OTHER INFORMATION: synthetic

<400> SEQUENCE: 264

Pro Pro Arg Leu Ser His Lys Gly Pro Met Pro Phe
1               5                   10

<210> SEQ ID NO 265
<211> LENGTH: 12
<212> TYPE: PRT
<213> ORGANISM: Artificial Sequence
<220> FEATURE:
<223> OTHER INFORMATION: synthetic

<400> SEQUENCE: 265

Pro Arg Pro Arg Leu Ser His Lys Gly Pro Met Pro
1               5                   10

<210> SEQ ID NO 266
<211> LENGTH: 11
<212> TYPE: PRT
<213> ORGANISM: Artificial Sequence
<220> FEATURE:
<223> OTHER INFORMATION: synthetic

<400> SEQUENCE: 266

Pro Pro Arg Leu Ser His Lys Gly Pro Met Pro
1               5                   10

<210> SEQ ID NO 267
<211> LENGTH: 11
<212> TYPE: PRT
<213> ORGANISM: Artificial Sequence
<220> FEATURE:
<223> OTHER INFORMATION: synthetic

<400> SEQUENCE: 267

Pro Arg Pro Arg Leu Ser His Lys Gly Pro Met
1               5                   10

<210> SEQ ID NO 268
<211> LENGTH: 10
<212> TYPE: PRT
<213> ORGANISM: Artificial Sequence
<220> FEATURE:
<223> OTHER INFORMATION: synthetic

<400> SEQUENCE: 268

Pro Pro Arg Leu Ser His Lys Gly Pro Met
1               5                   10

<210> SEQ ID NO 269
<211> LENGTH: 19
<212> TYPE: PRT
<213> ORGANISM: Artificial Sequence
<220> FEATURE:
<223> OTHER INFORMATION: synthetic

<400> SEQUENCE: 269

Pro Gln Arg Pro Arg Leu Ser His Lys Gly Pro Met Pro Phe Gly Gly
1               5                   10                  15

Gly Gly Gly

<210> SEQ ID NO 270

```
<211> LENGTH: 10
<212> TYPE: PRT
<213> ORGANISM: Artificial Sequence
<220> FEATURE:
<223> OTHER INFORMATION: synthetic

<400> SEQUENCE: 270

Pro Gln Arg Pro Arg Leu Ser His Lys Gly
1               5                   10

<210> SEQ ID NO 271
<211> LENGTH: 11
<212> TYPE: PRT
<213> ORGANISM: Artificial Sequence
<220> FEATURE:
<223> OTHER INFORMATION: synthetic

<400> SEQUENCE: 271

Pro Gln Arg Pro Arg Leu Ser His Lys Gly Pro
1               5                   10

<210> SEQ ID NO 272
<211> LENGTH: 13
<212> TYPE: PRT
<213> ORGANISM: Artificial Sequence
<220> FEATURE:
<223> OTHER INFORMATION: synthetic

<400> SEQUENCE: 272

Pro Gln Arg Pro Arg Leu Ser His Lys Gly Pro Met Ser
1               5                   10

<210> SEQ ID NO 273
<211> LENGTH: 25
<212> TYPE: PRT
<213> ORGANISM: Artificial Sequence
<220> FEATURE:
<223> OTHER INFORMATION: synthetic

<400> SEQUENCE: 273

Gly Lys Pro Ile Pro Asn Pro Leu Leu Gly Leu Asp Ser Thr Gln Arg
1               5                   10                  15

Pro Arg Leu Ser His Lys Gly Pro Met
            20                  25

<210> SEQ ID NO 274
<211> LENGTH: 148
<212> TYPE: PRT
<213> ORGANISM: Artificial Sequence
<220> FEATURE:
<223> OTHER INFORMATION: synthetic

<400> SEQUENCE: 274

Pro Gln Arg Pro Arg Leu Ser His Lys Gly Gly Gly Gly Ser Gly
1               5                   10                  15

Gly Gly Gly Ser Gly Gly Gly Ser Glu Val Gln Leu Val Glu Ser
            20                  25                  30

Gly Gly Gly Leu Val Lys Pro Gly Gly Ser Leu Arg Leu Ser Cys Ala
        35                  40                  45

Ala Ser Gly Ile Thr Phe Ser Asn Ala Trp Met Ser Trp Val Arg Gln
    50                  55                  60

Ala Pro Gly Lys Gly Leu Glu Trp Val Gly Arg Phe Lys Gly Lys Ala
65                  70                  75                  80

Asp Gly Gly Thr Val Asp Tyr Ala Ala Pro Val Lys Gly Arg Phe Thr
```

```
                    85                  90                  95

Ile Ser Arg Asp Asp Ser Lys Asn Thr Leu Tyr Leu Gln Met Asn Ser
            100                 105                 110

Leu Lys Asn Glu Asp Thr Ala Val Tyr Tyr Cys Thr Thr Gly Arg Ile
        115                 120                 125

Thr Met Val Arg Gly Val Leu Gly Tyr Trp Gly Gln Gly Thr Leu Val
    130                 135                 140

Thr Val Ser Ser
145

<210> SEQ ID NO 275
<211> LENGTH: 149
<212> TYPE: PRT
<213> ORGANISM: Artificial Sequence
<220> FEATURE:
<223> OTHER INFORMATION: synthetic

<400> SEQUENCE: 275

Pro Gln Arg Pro Arg Leu Ser His Lys Gly Pro Gly Gly Gly Gly Ser
1               5                   10                  15

Gly Gly Gly Gly Ser Gly Gly Gly Ser Glu Val Gln Leu Val Glu
            20                  25                  30

Ser Gly Gly Gly Leu Val Lys Pro Gly Gly Ser Leu Arg Leu Ser Cys
        35                  40                  45

Ala Ala Ser Gly Ile Thr Phe Ser Asn Ala Trp Met Ser Trp Val Arg
    50                  55                  60

Gln Ala Pro Gly Lys Gly Leu Glu Trp Val Gly Arg Phe Lys Gly Lys
65                  70                  75                  80

Ala Asp Gly Gly Thr Val Asp Tyr Ala Ala Pro Val Lys Gly Arg Phe
                85                  90                  95

Thr Ile Ser Arg Asp Asp Ser Lys Asn Thr Leu Tyr Leu Gln Met Asn
            100                 105                 110

Ser Leu Lys Asn Glu Asp Thr Ala Val Tyr Tyr Cys Thr Thr Gly Arg
        115                 120                 125

Ile Thr Met Val Arg Gly Val Leu Gly Tyr Trp Gly Gln Gly Thr Leu
    130                 135                 140

Val Thr Val Ser Ser
145

<210> SEQ ID NO 276
<211> LENGTH: 150
<212> TYPE: PRT
<213> ORGANISM: Artificial Sequence
<220> FEATURE:
<223> OTHER INFORMATION: synthetic

<400> SEQUENCE: 276

Pro Gln Arg Pro Arg Leu Ser His Lys Gly Pro Met Gly Gly Gly Gly
1               5                   10                  15

Ser Gly Gly Gly Gly Ser Gly Gly Gly Ser Glu Val Gln Leu Val
            20                  25                  30

Glu Ser Gly Gly Gly Leu Val Lys Pro Gly Gly Ser Leu Arg Leu Ser
        35                  40                  45

Cys Ala Ala Ser Gly Ile Thr Phe Ser Asn Ala Trp Met Ser Trp Val
    50                  55                  60

Arg Gln Ala Pro Gly Lys Gly Leu Glu Trp Val Gly Arg Phe Lys Gly
65                  70                  75                  80
```

Lys Ala Asp Gly Gly Thr Val Asp Tyr Ala Ala Pro Val Lys Gly Arg
            85                  90                  95

Phe Thr Ile Ser Arg Asp Asp Ser Lys Asn Thr Leu Tyr Leu Gln Met
        100                 105                 110

Asn Ser Leu Lys Asn Glu Asp Thr Ala Val Tyr Tyr Cys Thr Thr Gly
        115                 120                 125

Arg Ile Thr Met Val Arg Gly Val Leu Gly Tyr Trp Gly Gln Gly Thr
        130                 135                 140

Leu Val Thr Val Ser Ser
145                 150

<210> SEQ ID NO 277
<211> LENGTH: 151
<212> TYPE: PRT
<213> ORGANISM: Artificial Sequence
<220> FEATURE:
<223> OTHER INFORMATION: synthetic

<400> SEQUENCE: 277

Pro Gln Arg Pro Arg Leu Ser His Lys Gly Pro Met Ser Gly Gly Gly
1               5                   10                  15

Gly Ser Gly Gly Gly Ser Gly Gly Gly Ser Glu Val Gln Leu
            20                  25                  30

Val Glu Ser Gly Gly Gly Leu Val Lys Pro Gly Gly Ser Leu Arg Leu
        35                  40                  45

Ser Cys Ala Ala Ser Gly Ile Thr Phe Ser Asn Ala Trp Met Ser Trp
    50                  55                  60

Val Arg Gln Ala Pro Gly Lys Gly Leu Glu Trp Val Gly Arg Phe Lys
65                  70                  75                  80

Gly Lys Ala Asp Gly Gly Thr Val Asp Tyr Ala Ala Pro Val Lys Gly
                85                  90                  95

Arg Phe Thr Ile Ser Arg Asp Asp Ser Lys Asn Thr Leu Tyr Leu Gln
            100                 105                 110

Met Asn Ser Leu Lys Asn Glu Asp Thr Ala Val Tyr Tyr Cys Thr Thr
        115                 120                 125

Gly Arg Ile Thr Met Val Arg Gly Val Leu Gly Tyr Trp Gly Gln Gly
    130                 135                 140

Thr Leu Val Thr Val Ser Ser
145                 150

<210> SEQ ID NO 278
<211> LENGTH: 163
<212> TYPE: PRT
<213> ORGANISM: Artificial Sequence
<220> FEATURE:
<223> OTHER INFORMATION: synthetic

<400> SEQUENCE: 278

Gly Lys Pro Ile Pro Asn Pro Leu Leu Gly Leu Asp Ser Thr Gln Arg
1               5                   10                  15

Pro Arg Leu Ser His Lys Gly Pro Met Gly Gly Gly Ser Gly Gly
            20                  25                  30

Gly Gly Ser Gly Gly Gly Ser Glu Val Gln Leu Val Glu Ser Gly
        35                  40                  45

Gly Gly Leu Val Lys Pro Gly Gly Ser Leu Arg Leu Ser Cys Ala Ala
    50                  55                  60

Ser Gly Ile Thr Phe Ser Asn Ala Trp Met Ser Trp Val Arg Gln Ala
65                  70                  75                  80

```
Pro Gly Lys Gly Leu Glu Trp Val Gly Arg Phe Lys Gly Lys Ala Asp
                85                  90                  95

Gly Gly Thr Val Asp Tyr Ala Ala Pro Val Lys Gly Arg Phe Thr Ile
            100                 105                 110

Ser Arg Asp Asp Ser Lys Asn Thr Leu Tyr Leu Gln Met Asn Ser Leu
            115                 120                 125

Lys Asn Glu Asp Thr Ala Val Tyr Tyr Cys Thr Thr Gly Arg Ile Thr
130                 135                 140

Met Val Arg Gly Val Leu Gly Tyr Trp Gly Gln Gly Thr Leu Val Thr
145                 150                 155                 160

Val Ser Ser

<210> SEQ ID NO 279
<211> LENGTH: 139
<212> TYPE: PRT
<213> ORGANISM: Artificial Sequence
<220> FEATURE:
<223> OTHER INFORMATION: synthetic

<400> SEQUENCE: 279

Pro Gln Arg Pro Arg Leu Ser His Lys Gly Gly Gly Gly Ser Gly
1               5                   10                  15

Gly Gly Gly Ser Gly Gly Gly Ser Glu Val Gln Leu Leu Glu Ser
            20                  25                  30

Gly Gly Gly Leu Val Gln Pro Gly Gly Ser Leu Arg Leu Ser Cys Ala
            35                  40                  45

Ala Ser Gly Phe Thr Phe Ser Asn Tyr Ala Met Asn Trp Val Arg Gln
50                  55                  60

Ala Pro Gly Arg Gly Leu Glu Trp Val Ser Ala Ile His Tyr Asp Gly
65                  70                  75                  80

Ser Asn Ser Tyr Tyr Ala Asp Ser Val Lys Gly Arg Phe Thr Ile Ser
                85                  90                  95

Arg Asp Asn Ser Lys Asn Thr Leu Tyr Leu Gln Met Asn Ser Leu Arg
            100                 105                 110

Ala Glu Asp Thr Ala Ile Tyr Tyr Cys Ala Ile Leu Ser Arg Val Tyr
            115                 120                 125

Trp Gly Gln Gly Thr Leu Val Thr Val Ser Ser
    130                 135

<210> SEQ ID NO 280
<211> LENGTH: 140
<212> TYPE: PRT
<213> ORGANISM: Artificial Sequence
<220> FEATURE:
<223> OTHER INFORMATION: synthetic

<400> SEQUENCE: 280

Pro Gln Arg Pro Arg Leu Ser His Lys Gly Pro Gly Gly Gly Ser
1               5                   10                  15

Gly Gly Gly Gly Ser Gly Gly Gly Ser Glu Val Gln Leu Leu Glu
            20                  25                  30

Ser Gly Gly Gly Leu Val Gln Pro Gly Gly Ser Leu Arg Leu Ser Cys
            35                  40                  45

Ala Ala Ser Gly Phe Thr Phe Ser Asn Tyr Ala Met Asn Trp Val Arg
50                  55                  60

Gln Ala Pro Gly Arg Gly Leu Glu Trp Val Ser Ala Ile His Tyr Asp
65                  70                  75                  80
```

Gly Ser Asn Ser Tyr Tyr Ala Asp Ser Val Lys Gly Arg Phe Thr Ile
                85                  90                  95

Ser Arg Asp Asn Ser Lys Asn Thr Leu Tyr Leu Gln Met Asn Ser Leu
            100                 105                 110

Arg Ala Glu Asp Thr Ala Ile Tyr Tyr Cys Ala Ile Leu Ser Arg Val
        115                 120                 125

Tyr Trp Gly Gln Gly Thr Leu Val Thr Val Ser Ser
    130                 135                 140

<210> SEQ ID NO 281
<211> LENGTH: 141
<212> TYPE: PRT
<213> ORGANISM: Artificial Sequence
<220> FEATURE:
<223> OTHER INFORMATION: synthetic

<400> SEQUENCE: 281

Pro Gln Arg Pro Arg Leu Ser His Lys Gly Pro Met Gly Gly Gly Gly
1               5                   10                  15

Ser Gly Gly Gly Gly Ser Gly Gly Gly Ser Glu Val Gln Leu Leu
            20                  25                  30

Glu Ser Gly Gly Gly Leu Val Gln Pro Gly Gly Ser Leu Arg Leu Ser
        35                  40                  45

Cys Ala Ala Ser Gly Phe Thr Phe Ser Asn Tyr Ala Met Asn Trp Val
    50                  55                  60

Arg Gln Ala Pro Gly Arg Gly Leu Glu Trp Val Ser Ala Ile His Tyr
65                  70                  75                  80

Asp Gly Ser Asn Ser Tyr Tyr Ala Asp Ser Val Lys Gly Arg Phe Thr
                85                  90                  95

Ile Ser Arg Asp Asn Ser Lys Asn Thr Leu Tyr Leu Gln Met Asn Ser
            100                 105                 110

Leu Arg Ala Glu Asp Thr Ala Ile Tyr Tyr Cys Ala Ile Leu Ser Arg
        115                 120                 125

Val Tyr Trp Gly Gln Gly Thr Leu Val Thr Val Ser Ser
    130                 135                 140

<210> SEQ ID NO 282
<211> LENGTH: 142
<212> TYPE: PRT
<213> ORGANISM: Artificial Sequence
<220> FEATURE:
<223> OTHER INFORMATION: synthetic

<400> SEQUENCE: 282

Pro Gln Arg Pro Arg Leu Ser His Lys Gly Pro Met Ser Gly Gly Gly
1               5                   10                  15

Gly Ser Gly Gly Gly Gly Ser Gly Gly Gly Ser Glu Val Gln Leu
            20                  25                  30

Leu Glu Ser Gly Gly Gly Leu Val Gln Pro Gly Gly Ser Leu Arg Leu
        35                  40                  45

Ser Cys Ala Ala Ser Gly Phe Thr Phe Ser Asn Tyr Ala Met Asn Trp
    50                  55                  60

Val Arg Gln Ala Pro Gly Arg Gly Leu Glu Trp Val Ser Ala Ile His
65                  70                  75                  80

Tyr Asp Gly Ser Asn Ser Tyr Tyr Ala Asp Ser Val Lys Gly Arg Phe
                85                  90                  95

Thr Ile Ser Arg Asp Asn Ser Lys Asn Thr Leu Tyr Leu Gln Met Asn

```
              100                 105                 110
Ser Leu Arg Ala Glu Asp Thr Ala Ile Tyr Tyr Cys Ala Ile Leu Ser
            115                 120                 125

Arg Val Tyr Trp Gly Gln Gly Thr Leu Val Thr Val Ser Ser
        130                 135                 140
```

<210> SEQ ID NO 283
<211> LENGTH: 15
<212> TYPE: PRT
<213> ORGANISM: Artificial Sequence
<220> FEATURE:
<223> OTHER INFORMATION: synthetic

<400> SEQUENCE: 283

```
Pro Gln Arg Pro Arg Leu Ser His Lys Gly Pro Met Pro Phe Arg
1               5                   10                  15
```

<210> SEQ ID NO 284
<211> LENGTH: 15
<212> TYPE: PRT
<213> ORGANISM: Artificial Sequence
<220> FEATURE:
<223> OTHER INFORMATION: synthetic

<400> SEQUENCE: 284

```
Pro Gln Arg Pro Arg Leu Ser His Lys Gly Pro Met Pro Phe Ser
1               5                   10                  15
```

<210> SEQ ID NO 285
<211> LENGTH: 15
<212> TYPE: PRT
<213> ORGANISM: Artificial Sequence
<220> FEATURE:
<223> OTHER INFORMATION: synthetic

<400> SEQUENCE: 285

```
Pro Gln Arg Pro Arg Leu Ser His Lys Gly Pro Met Pro Phe His
1               5                   10                  15
```

<210> SEQ ID NO 286
<211> LENGTH: 387
<212> TYPE: DNA
<213> ORGANISM: Artificial Sequence
<220> FEATURE:
<223> OTHER INFORMATION: synthetic

<400> SEQUENCE: 286

```
gaggtgcaac tggtggagtc tgggggaggc ttggtccagc ctgggggtc cctgagactc      60 tcctgtgtag cctctggatt caccttaat aactattgga tgagttgggt ccgccaggct     120
ccagggaagg ggctggagtg ggtggccaac ataaagcaag atggaagtga gagatactat    180
gtggactctg tgaagggccg attcaccatc tccagaggcg acgccaagaa ctcactgtat    240
ctgcaaatga gagcctgag agccgaggac acggctgttt atttctgtgc gagagatcga    300
tttggatata gtttctacga taagggggta cgctactact acggtatgga cgtctggggc    360
caagggacca cggtcaccgt ctcctca                                         387
```

<210> SEQ ID NO 287
<211> LENGTH: 129
<212> TYPE: PRT
<213> ORGANISM: Artificial Sequence
<220> FEATURE:
<223> OTHER INFORMATION: synthetic

<400> SEQUENCE: 287

Glu Val Gln Leu Val Glu Ser Gly Gly Leu Val Gln Pro Gly Gly
1               5                   10                  15

Ser Leu Arg Leu Ser Cys Val Ala Ser Gly Phe Thr Phe Asn Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Arg Tyr Tyr Val Asp Ser Val
    50                  55                  60

Lys Gly Arg Phe Thr Ile Ser Arg Gly Asp Ala Lys Asn Ser Leu Tyr
65                  70                  75                  80

Leu Gln Met Lys Ser Leu Arg Ala Glu Asp Thr Ala Val Tyr Phe Cys
            85                  90                  95

Ala Arg Asp Arg Phe Gly Tyr Ser Phe Tyr Asp Lys Val Arg Tyr
        100                 105                 110

Tyr Tyr Gly Met Asp Val Trp Gly Gln Gly Thr Thr Val Thr Val Ser
        115                 120                 125

Ser

<210> SEQ ID NO 288
<211> LENGTH: 24
<212> TYPE: DNA
<213> ORGANISM: Artificial Sequence
<220> FEATURE:
<223> OTHER INFORMATION: synthetic

<400> SEQUENCE: 288
ggattcacct ttaataacta ttgg                                      24

<210> SEQ ID NO 289
<211> LENGTH: 8
<212> TYPE: PRT
<213> ORGANISM: Artificial Sequence
<220> FEATURE:
<223> OTHER INFORMATION: synthetic

<400> SEQUENCE: 289

Gly Phe Thr Phe Asn Asn Tyr Trp
1               5

<210> SEQ ID NO 290
<211> LENGTH: 24
<212> TYPE: DNA
<213> ORGANISM: Artificial Sequence
<220> FEATURE:
<223> OTHER INFORMATION: synthetic

<400> SEQUENCE: 290
ataaagcaag atggaagtga gaga                                      24

<210> SEQ ID NO 291
<211> LENGTH: 8
<212> TYPE: PRT
<213> ORGANISM: Artificial Sequence
<220> FEATURE:
<223> OTHER INFORMATION: synthetic

<400> SEQUENCE: 291

Ile Lys Gln Asp Gly Ser Glu Arg
1               5

<210> SEQ ID NO 292
<211> LENGTH: 66
<212> TYPE: DNA
<213> ORGANISM: Artificial Sequence
<220> FEATURE:
<223> OTHER INFORMATION: synthetic

<400> SEQUENCE: 292

```
gcgagagatc gatttggata tagtttctac gataaggggg tacgctacta ctacggtatg    60
gacgtc                                                               66
```

<210> SEQ ID NO 293
<211> LENGTH: 22
<212> TYPE: PRT
<213> ORGANISM: Artificial Sequence
<220> FEATURE:
<223> OTHER INFORMATION: synthetic

<400> SEQUENCE: 293

Ala Arg Asp Arg Phe Gly Tyr Ser Phe Tyr Asp Lys Gly Val Arg Tyr
1               5                   10                  15

Tyr Tyr Gly Met Asp Val
            20

<210> SEQ ID NO 294
<211> LENGTH: 321
<212> TYPE: DNA
<213> ORGANISM: Artificial Sequence
<220> FEATURE:
<223> OTHER INFORMATION: synthetic

<400> SEQUENCE: 294

```
gacatccaga tgacccagtc tccatcctcc ctgtctgcat ctgtaggaga cagagtcacc    60
atcacttgcc gggcaagtca gggcattaga aatgatttag gctggtatca gcagagacca   120
gggaaagccc ctaagcgcct gatctatgct gcatccagtt tgcaaactgg ggtcccatca   180
aggttcagcg gcagtggatc tgggacagaa ttcactctca caatcagcgg cctgcagcct   240
gaagattttg caacttatta ctgtctacag cataatagtt accctcggac gttcggccaa   300
gggaccaagg tggaaatcag a                                             321
```

<210> SEQ ID NO 295
<211> LENGTH: 107
<212> TYPE: PRT
<213> ORGANISM: Artificial Sequence
<220> FEATURE:
<223> OTHER INFORMATION: synthetic

<400> SEQUENCE: 295

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Arg Pro Gly Lys Ala Pro Lys Arg Leu Ile
        35                  40                  45

Tyr Ala Ala Ser Ser Leu Gln Thr Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Arg
        100                 105

<210> SEQ ID NO 296
<211> LENGTH: 18
<212> TYPE: DNA
<213> ORGANISM: Artificial Sequence
<220> FEATURE:
<223> OTHER INFORMATION: synthetic

<400> SEQUENCE: 296
cagggcatta gaaatgat                                                 18

<210> SEQ ID NO 297
<211> LENGTH: 6
<212> TYPE: PRT
<213> ORGANISM: Artificial Sequence
<220> FEATURE:
<223> OTHER INFORMATION: synthetic

<400> SEQUENCE: 297

Gln Gly Ile Arg Asn Asp
1               5

<210> SEQ ID NO 298
<211> LENGTH: 9
<212> TYPE: DNA
<213> ORGANISM: Artificial Sequence
<220> FEATURE:
<223> OTHER INFORMATION: synthetic

<400> SEQUENCE: 298 gctgcatcc                                                            9

<210> SEQ ID NO 299
<211> LENGTH: 3
<212> TYPE: PRT
<213> ORGANISM: Artificial Sequence
<220> FEATURE:
<223> OTHER INFORMATION: synthetic

<400> SEQUENCE: 299

Ala Ala Ser
1

<210> SEQ ID NO 300
<211> LENGTH: 27
<212> TYPE: DNA
<213> ORGANISM: Artificial Sequence
<220> FEATURE:
<223> OTHER INFORMATION: synthetic

<400> SEQUENCE: 300
ctacagcata atagttaccc tcggacg                                        27

<210> SEQ ID NO 301
<211> LENGTH: 9
<212> TYPE: PRT
<213> ORGANISM: Artificial Sequence
<220> FEATURE:
<223> OTHER INFORMATION: synthetic

<400> SEQUENCE: 301

Leu Gln His Asn Ser Tyr Pro Arg Thr
1               5

<210> SEQ ID NO 302
<211> LENGTH: 387
<212> TYPE: DNA
<213> ORGANISM: Artificial Sequence
<220> FEATURE:
<223> OTHER INFORMATION: synthetic

<400> SEQUENCE: 302

```
gaggtgcagc tggtggagtc tgggggaggt ttggtccagc ctggggggtc cctgagactc      60
tcctgtgcag cctctggatt cacctttagt agctttggga tgagttgggt ccgccaggtt     120
ccagggaagg ggctggagtg ggtggccaac ataaagcaag atggaagtga aaatactat      180
gtggactctg tgaagggccg attcaccatc tccagagaca cgccaagaa ctcactgtat      240
ctgcaaatga acagcctgag agccgaggac acggctgtgt attactgtgc gagagataga     300
tttggatata gtgtctacga taaggggta cgctactact acggtatgga cgtctggggc      360
caagggacca cggtcaccgt ctcctca                                         387
```

<210> SEQ ID NO 303
<211> LENGTH: 129
<212> TYPE: PRT
<213> ORGANISM: Artificial Sequence
<220> FEATURE:
<223> OTHER INFORMATION: synthetic

<400> SEQUENCE: 303

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Trp Met Ser Trp Val Arg Gln Val Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Phe Gly Tyr Ser Val Tyr Asp Lys Gly Val Arg Tyr
            100                 105                 110

Tyr Tyr Gly Met Asp Val Trp Gly Gln Gly Thr Thr Val Thr Val Ser
        115                 120                 125

Ser

<210> SEQ ID NO 304
<211> LENGTH: 24
<212> TYPE: DNA
<213> ORGANISM: Artificial Sequence
<220> FEATURE:
<223> OTHER INFORMATION: synthetic

<400> SEQUENCE: 304

```
ggattcacct ttagtagctt ttgg                                             24
```

<210> SEQ ID NO 305
<211> LENGTH: 8
<212> TYPE: PRT
<213> ORGANISM: Artificial Sequence
<220> FEATURE:
<223> OTHER INFORMATION: synthetic

```
<400> SEQUENCE: 305

Gly Phe Thr Phe Ser Ser Phe Trp
1               5

<210> SEQ ID NO 306
<211> LENGTH: 24
<212> TYPE: DNA
<213> ORGANISM: Artificial Sequence
<220> FEATURE:
<223> OTHER INFORMATION: synthetic

<400> SEQUENCE: 306
ataaagcaag atggaagtga gaaa                                              24

<210> SEQ ID NO 307
<211> LENGTH: 8
<212> TYPE: PRT
<213> ORGANISM: Artificial Sequence
<220> FEATURE:
<223> OTHER INFORMATION: synthetic

<400> SEQUENCE: 307

Ile Lys Gln Asp Gly Ser Glu Lys
1               5

<210> SEQ ID NO 308
<211> LENGTH: 66
<212> TYPE: DNA
<213> ORGANISM: Artificial Sequence
<220> FEATURE:
<223> OTHER INFORMATION: synthetic

<400> SEQUENCE: 308
gcgagagata gatttggata tagtgtctac gataaggggg tacgctacta ctacggtatg      60
gacgtc                                                                 66

<210> SEQ ID NO 309
<211> LENGTH: 22
<212> TYPE: PRT
<213> ORGANISM: Artificial Sequence
<220> FEATURE:
<223> OTHER INFORMATION: synthetic

<400> SEQUENCE: 309

Ala Arg Asp Arg Phe Gly Tyr Ser Val Tyr Asp Lys Gly Val Arg Tyr
1               5                   10                  15

Tyr Tyr Gly Met Asp Val
            20

<210> SEQ ID NO 310
<211> LENGTH: 321
<212> TYPE: DNA
<213> ORGANISM: Artificial Sequence
<220> FEATURE:
<223> OTHER INFORMATION: synthetic

<400> SEQUENCE: 310
gacatccaga tgacccagtc tccatcctcc ctgtctgtat ctgtaggaga cagagtcacc      60
atcacttgcc gggcaagtca gggcattaga aatgatttag ctggtatca gcagaaacca     120 gggaaagccc ctaagcgcct gatctatgct gcatccagtt tgcaaagtgg ggtcccatca    180
aggttcagcg gcagtggatc tgggacagaa ttcactctca caatcagcgg cctgcagtct    240
gaagattttg caacttatta ctgtctacag cataagagtt accctcggac gttcggccaa    300
```
gggaccaagg tggaaatcaa a                                        321

<210> SEQ ID NO 311
<211> LENGTH: 107
<212> TYPE: PRT
<213> ORGANISM: Artificial Sequence
<220> FEATURE:
<223> OTHER INFORMATION: synthetic

<400> SEQUENCE: 311

Asp Ile Gln Met Thr Gln Ser Pro Ser Ser Leu Ser Val Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Gly Leu Gln Ser
65                  70                  75                  80

Glu Asp Phe Ala Thr Tyr Tyr Cys Leu Gln His Lys Ser Tyr Pro Arg
                85                  90                  95

Thr Phe Gly Gln Gly Thr Lys Val Glu Ile Lys
            100                 105

<210> SEQ ID NO 312
<211> LENGTH: 18
<212> TYPE: DNA
<213> ORGANISM: Artificial Sequence
<220> FEATURE:
<223> OTHER INFORMATION: synthetic

<400> SEQUENCE: 312
cagggcatta gaaatgat                                            18

<210> SEQ ID NO 313
<211> LENGTH: 6
<212> TYPE: PRT
<213> ORGANISM: Artificial Sequence
<220> FEATURE:
<223> OTHER INFORMATION: synthetic

<400> SEQUENCE: 313

Gln Gly Ile Arg Asn Asp
1               5

<210> SEQ ID NO 314
<211> LENGTH: 9
<212> TYPE: DNA
<213> ORGANISM: Artificial Sequence
<220> FEATURE:
<223> OTHER INFORMATION: synthetic

<400> SEQUENCE: 314 gctgcatcc                                                      9

<210> SEQ ID NO 315
<211> LENGTH: 3
<212> TYPE: PRT
<213> ORGANISM: Artificial Sequence
<220> FEATURE:
<223> OTHER INFORMATION: synthetic

<400> SEQUENCE: 315

Ala Ala Ser
1

<210> SEQ ID NO 316
<211> LENGTH: 27
<212> TYPE: DNA
<213> ORGANISM: Artificial Sequence
<220> FEATURE:
<223> OTHER INFORMATION: synthetic

<400> SEQUENCE: 316
ctacagcata agagttaccc tcggacg                                          27

<210> SEQ ID NO 317
<211> LENGTH: 9
<212> TYPE: PRT
<213> ORGANISM: Artificial Sequence
<220> FEATURE:
<223> OTHER INFORMATION: synthetic

<400> SEQUENCE: 317

Leu Gln His Lys Ser Tyr Pro Arg Thr
1               5

<210> SEQ ID NO 318
<211> LENGTH: 387
<212> TYPE: DNA
<213> ORGANISM: Artificial Sequence
<220> FEATURE:
<223> OTHER INFORMATION: synthetic

<400> SEQUENCE: 318
gaggtgcagt tggtggagtc tgggggaggt ttggtccagc ctgggggtc cctgagactc        60
tcctgtgcag cctctggatt cacctttagt agcttttgga tgagttgggt ccgccaggtt      120
ccagggaagg ggctggagtg ggtggccaac ataaagcaag atggaagtga aaatactct       180
gtggactctg tgaagggccg attcaccatc tccagagaca acgccaagaa ctcactgtat      240
ctgcaaatga acagcctgag agccgaggac acggctgtgt attactgtgc gagagataga      300
tttggatata gtttctacga taagggggta cgttactact acggtatgga cgtctggggc      360
caagggacca cggtcaccgt ctcctca                                          387

<210> SEQ ID NO 319
<211> LENGTH: 129
<212> TYPE: PRT
<213> ORGANISM: Artificial Sequence
<220> FEATURE:
<223> OTHER INFORMATION: synthetic

<400> SEQUENCE: 319

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Trp Met Ser Trp Val Arg Gln Val Pro Gly Lys Gly Leu Glu Trp Val
            35                  40                  45

Ala Asn Ile Lys Gln Asp Gly Ser Glu Lys Tyr Ser Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Phe Gly Tyr Ser Phe Tyr Asp Lys Gly Val Arg Tyr
            100                 105                 110

Tyr Tyr Gly Met Asp Val Trp Gly Gln Gly Thr Thr Val Thr Val Ser
        115                 120                 125

Ser

<210> SEQ ID NO 320
<211> LENGTH: 24
<212> TYPE: DNA
<213> ORGANISM: Artificial Sequence
<220> FEATURE:
<223> OTHER INFORMATION: synthetic

<400> SEQUENCE: 320
ggattcacct ttagtagctt ttgg                                          24

<210> SEQ ID NO 321
<211> LENGTH: 8
<212> TYPE: PRT
<213> ORGANISM: Artificial Sequence
<220> FEATURE:
<223> OTHER INFORMATION: synthetic

<400> SEQUENCE: 321

Gly Phe Thr Phe Ser Ser Phe Trp
1               5

<210> SEQ ID NO 322
<211> LENGTH: 24
<212> TYPE: DNA
<213> ORGANISM: Artificial Sequence
<220> FEATURE:
<223> OTHER INFORMATION: synthetic

<400> SEQUENCE: 322
ataaagcaag atggaagtga gaaa                                          24

<210> SEQ ID NO 323
<211> LENGTH: 8
<212> TYPE: PRT
<213> ORGANISM: Artificial Sequence
<220> FEATURE:
<223> OTHER INFORMATION: synthetic

<400> SEQUENCE: 323

Ile Lys Gln Asp Gly Ser Glu Lys
1               5

<210> SEQ ID NO 324
<211> LENGTH: 66
<212> TYPE: DNA
<213> ORGANISM: Artificial Sequence
<220> FEATURE:
<223> OTHER INFORMATION: synthetic

<400> SEQUENCE: 324
gcgagagata gatttggata tagtttctac gataaggggg tacgttacta ctacggtatg   60
gacgtc                                                              66

<210> SEQ ID NO 325
<211> LENGTH: 22
<212> TYPE: PRT

<213> ORGANISM: Artificial Sequence
<220> FEATURE:
<223> OTHER INFORMATION: synthetic

<400> SEQUENCE: 325

Ala Arg Asp Arg Phe Gly Tyr Ser Phe Tyr Asp Lys Gly Val Arg Tyr
1               5                   10                  15

Tyr Tyr Gly Met Asp Val
            20

<210> SEQ ID NO 326
<211> LENGTH: 321
<212> TYPE: DNA
<213> ORGANISM: Artificial Sequence
<220> FEATURE:
<223> OTHER INFORMATION: synthetic

<400> SEQUENCE: 326

```
gacatccaga tgacccagtc tccatcctcc ctgtctgtat ctgtaggaga cagagtcacc     60
atcacttgcc gggcaagtca gggcattaga aatgatttag ggtggtatca gcagaaacca    120
gggaaagccc ctaagcgcct gatctatgct acatccagtt tgcaaagtgg ggtcccatca    180
aggttcagcg gcagtggatc tgggacagaa ttcactctca caatcagcgg cctgcagcct    240
gaagattttg caacttatta ctgtctacag cataatagtt accctcggac gttcggccaa    300
gggaccaagg tggaaatcaa a                                              321
```

<210> SEQ ID NO 327
<211> LENGTH: 107
<212> TYPE: PRT
<213> ORGANISM: Artificial Sequence
<220> FEATURE:
<223> OTHER INFORMATION: synthetic

<400> SEQUENCE: 327

Asp Ile Gln Met Thr Gln Ser Pro Ser Ser Leu Ser Val Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys
            100                 105

<210> SEQ ID NO 328
<211> LENGTH: 18
<212> TYPE: DNA
<213> ORGANISM: Artificial Sequence
<220> FEATURE:
<223> OTHER INFORMATION: synthetic

<400> SEQUENCE: 328
cagggcatta gaaatgat                                                   18

<210> SEQ ID NO 329

```
<211> LENGTH: 6
<212> TYPE: PRT
<213> ORGANISM: Artificial Sequence
<220> FEATURE:
<223> OTHER INFORMATION: synthetic

<400> SEQUENCE: 329

Gln Gly Ile Arg Asn Asp
1               5

<210> SEQ ID NO 330
<211> LENGTH: 9
<212> TYPE: DNA
<213> ORGANISM: Artificial Sequence
<220> FEATURE:
<223> OTHER INFORMATION: synthetic

<400> SEQUENCE: 330 gctacatcc                                                                  9

<210> SEQ ID NO 331
<211> LENGTH: 3
<212> TYPE: PRT
<213> ORGANISM: Artificial Sequence
<220> FEATURE:
<223> OTHER INFORMATION: synthetic

<400> SEQUENCE: 331

Ala Thr Ser
1

<210> SEQ ID NO 332
<211> LENGTH: 27
<212> TYPE: DNA
<213> ORGANISM: Artificial Sequence
<220> FEATURE:
<223> OTHER INFORMATION: synthetic

<400> SEQUENCE: 332
ctacagcata atagttaccc tcggacg                                              27

<210> SEQ ID NO 333
<211> LENGTH: 9
<212> TYPE: PRT
<213> ORGANISM: Artificial Sequence
<220> FEATURE:
<223> OTHER INFORMATION: synthetic

<400> SEQUENCE: 333

Leu Gln His Asn Ser Tyr Pro Arg Thr
1               5

<210> SEQ ID NO 334
<211> LENGTH: 387
<212> TYPE: DNA
<213> ORGANISM: Artificial Sequence
<220> FEATURE:
<223> OTHER INFORMATION: synthetic

<400> SEQUENCE: 334
gaggtgcaac tggtggagtc tgggggaggc ttggtccagc ctgggggtc  cctgagactc        60 tcctgtgtag cctctggatt caccttttaat aactattgga tgagttgggt ccgccaggct      120
ccagggaagg ggctggagtg ggtggccaac ataaagcaag atggaagtga gagatattat      180
gtggactctg tgaagggccg attcaccatc tccagaggcg acgccaagaa ctcactgtat      240
```

```
ctgcaaatga agagcctgag agccgaggac acggctgttt atttctgtgc gagagatcga    300
tttggatata gtttctacga taagggggta cgctactact acggtatgga cgtctggggc    360
caagggacca cggtcaccgt ctcctca                                        387
```

<210> SEQ ID NO 335
<211> LENGTH: 129
<212> TYPE: PRT
<213> ORGANISM: Artificial Sequence
<220> FEATURE:
<223> OTHER INFORMATION: synthetic

<400> SEQUENCE: 335

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Asn Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Arg Tyr Tyr Val Asp Ser Val
    50                  55                  60

Lys Gly Arg Phe Thr Ile Ser Arg Gly Asp Ala Lys Asn Ser Leu Tyr
65                  70                  75                  80

Leu Gln Met Lys Ser Leu Arg Ala Glu Asp Thr Ala Val Tyr Phe Cys
                85                  90                  95

Ala Arg Asp Arg Phe Gly Tyr Ser Phe Tyr Asp Lys Gly Val Arg Tyr
            100                 105                 110

Tyr Tyr Gly Met Asp Val Trp Gly Gln Gly Thr Thr Val Thr Val Ser
        115                 120                 125

Ser
```

<210> SEQ ID NO 336
<211> LENGTH: 24
<212> TYPE: DNA
<213> ORGANISM: Artificial Sequence
<220> FEATURE:
<223> OTHER INFORMATION: synthetic

<400> SEQUENCE: 336

```
ggattcacct ttaataacta ttgg                                           24
```

<210> SEQ ID NO 337
<211> LENGTH: 8
<212> TYPE: PRT
<213> ORGANISM: Artificial Sequence
<220> FEATURE:
<223> OTHER INFORMATION: synthetic

<400> SEQUENCE: 337

```
Gly Phe Thr Phe Asn Asn Tyr Trp
1               5
```

<210> SEQ ID NO 338
<211> LENGTH: 24
<212> TYPE: DNA
<213> ORGANISM: Artificial Sequence
<220> FEATURE:
<223> OTHER INFORMATION: synthetic

<400> SEQUENCE: 338

```
ataaagcaag atggaagtga gaga                                           24
```

<210> SEQ ID NO 339
<211> LENGTH: 8
<212> TYPE: PRT
<213> ORGANISM: Artificial Sequence
<220> FEATURE:
<223> OTHER INFORMATION: synthetic

<400> SEQUENCE: 339

Ile Lys Gln Asp Gly Ser Glu Arg
1               5

<210> SEQ ID NO 340
<211> LENGTH: 66
<212> TYPE: DNA
<213> ORGANISM: Artificial Sequence
<220> FEATURE:
<223> OTHER INFORMATION: synthetic

<400> SEQUENCE: 340
gcgagagatc gatttggata tagtttctac gataaggggg tacgctacta ctacggtatg    60
gacgtc                                                               66

<210> SEQ ID NO 341
<211> LENGTH: 22
<212> TYPE: PRT
<213> ORGANISM: Artificial Sequence
<220> FEATURE:
<223> OTHER INFORMATION: synthetic

<400> SEQUENCE: 341

Ala Arg Asp Arg Phe Gly Tyr Ser Phe Tyr Asp Lys Gly Val Arg Tyr
1               5                   10                  15

Tyr Tyr Gly Met Asp Val
            20

<210> SEQ ID NO 342
<211> LENGTH: 321
<212> TYPE: DNA
<213> ORGANISM: Artificial Sequence
<220> FEATURE:
<223> OTHER INFORMATION: synthetic

<400> SEQUENCE: 342
gacatccaga tgacccagtc tccatcctcc ctgtctgcat ctgtaggaga cagagtcacc    60
atcacttgcc gggcaagtca gggcattaga aatgatttag ctggtatca acagagacca   120 gggaaagccc ctaagcgcct gatctatgct gcatccagtt tgcaaactgg ggtcccatca   180
aggttcagcg gcagtggatc tgggacagaa ttcactctca caatcagcgg cctgcagcct   240
gatgattttg caacttatta ctgtctacag cataatagtt accctcggac gttcggccaa   300
gggaccaagg tggaaatcag a                                             321

<210> SEQ ID NO 343
<211> LENGTH: 107
<212> TYPE: PRT
<213> ORGANISM: Artificial Sequence
<220> FEATURE:
<223> OTHER INFORMATION: synthetic

<400> SEQUENCE: 343

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp

```
            20                  25                  30
Leu Gly Trp Tyr Gln Gln Arg Pro Gly Lys Ala Pro Lys Arg Leu Ile
        35                  40                  45

Tyr Ala Ala Ser Ser Leu Gln Thr Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Asp Asp Phe Ala Thr Tyr Tyr Cys Leu Gln His Asn Ser Tyr Pro Arg
                85                  90                  95

Thr Phe Gly Gln Gly Thr Lys Val Glu Ile Arg
            100                 105
```

<210> SEQ ID NO 344
<211> LENGTH: 18
<212> TYPE: DNA
<213> ORGANISM: Artificial Sequence
<220> FEATURE:
<223> OTHER INFORMATION: synthetic

<400> SEQUENCE: 344
cagggcatta gaaatgat         18

<210> SEQ ID NO 345
<211> LENGTH: 6
<212> TYPE: PRT
<213> ORGANISM: Artificial Sequence
<220> FEATURE:
<223> OTHER INFORMATION: synthetic

<400> SEQUENCE: 345

```
Gln Gly Ile Arg Asn Asp
1               5
```

<210> SEQ ID NO 346
<211> LENGTH: 9
<212> TYPE: DNA
<213> ORGANISM: Artificial Sequence
<220> FEATURE:
<223> OTHER INFORMATION: synthetic

<400> SEQUENCE: 346 gctgcatcc         9

<210> SEQ ID NO 347
<211> LENGTH: 3
<212> TYPE: PRT
<213> ORGANISM: Artificial Sequence
<220> FEATURE:
<223> OTHER INFORMATION: synthetic

<400> SEQUENCE: 347

```
Ala Ala Ser
1
```

<210> SEQ ID NO 348
<211> LENGTH: 27
<212> TYPE: DNA
<213> ORGANISM: Artificial Sequence
<220> FEATURE:
<223> OTHER INFORMATION: synthetic

<400> SEQUENCE: 348
ctacagcata atagttaccc tcggacg         27

<210> SEQ ID NO 349
<211> LENGTH: 9
<212> TYPE: PRT
<213> ORGANISM: Artificial Sequence
<220> FEATURE:
<223> OTHER INFORMATION: synthetic

<400> SEQUENCE: 349

Leu Gln His Asn Ser Tyr Pro Arg Thr
1               5

<210> SEQ ID NO 350
<211> LENGTH: 387
<212> TYPE: DNA
<213> ORGANISM: Artificial Sequence
<220> FEATURE:
<223> OTHER INFORMATION: synthetic

<400> SEQUENCE: 350

```
gaggtgcagc tggaggaatc tgggggaggc ctggtccagc ctgggggtc cctgagactc      60 tcctgtgcag cctctggatt cacctttact agcttttgga tgagttgggt ccgccaggtt    120
ccagggaagg ggctgcagtg ggtggccaat ataaagcaag atggaactga aaatactat    180 gtggactctg tgaagggccg attcaccatc tccagagaca acgccaagaa ctcactgtat    240
ctgcaaatga acagcctgag agccgaggac acggctgtgt attactgtgc gagaaacgg    300 tttggatata gtctcttcga taaggggggta cgctactact acggtatgga cgtctggggc    360
caagggacct cggtcaccgt ctcctca                                         387
```

<210> SEQ ID NO 351
<211> LENGTH: 129
<212> TYPE: PRT
<213> ORGANISM: Artificial Sequence
<220> FEATURE:
<223> OTHER INFORMATION: synthetic

<400> SEQUENCE: 351

Glu Val Gln Leu Glu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Phe
            20                  25                  30

Trp Met Ser Trp Val Arg Gln Val Pro Gly Lys Gly Leu Gln Trp Val
        35                  40                  45

Ala Asn Ile Lys Gln Asp Gly Thr Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Phe Gly Tyr Ser Leu Phe Asp Lys Gly Val Arg Tyr
            100                 105                 110

Tyr Tyr Gly Met Asp Val Trp Gly Gln Gly Thr Ser Val Thr Val Ser
        115                 120                 125

Ser

<210> SEQ ID NO 352
<211> LENGTH: 24
<212> TYPE: DNA
<213> ORGANISM: Artificial Sequence
<220> FEATURE:

<223> OTHER INFORMATION: synthetic

<400> SEQUENCE: 352
ggattcacct ttactagctt ttgg                                              24

<210> SEQ ID NO 353
<211> LENGTH: 8
<212> TYPE: PRT
<213> ORGANISM: Artificial Sequence
<220> FEATURE:
<223> OTHER INFORMATION: synthetic

<400> SEQUENCE: 353

Gly Phe Thr Phe Thr Ser Phe Trp
1               5

<210> SEQ ID NO 354
<211> LENGTH: 24
<212> TYPE: DNA
<213> ORGANISM: Artificial Sequence
<220> FEATURE:
<223> OTHER INFORMATION: synthetic

<400> SEQUENCE: 354
ataaagcaag atggaactga gaaa                                              24

<210> SEQ ID NO 355
<211> LENGTH: 8
<212> TYPE: PRT
<213> ORGANISM: Artificial Sequence
<220> FEATURE:
<223> OTHER INFORMATION: synthetic

<400> SEQUENCE: 355

Ile Lys Gln Asp Gly Thr Glu Lys
1               5

<210> SEQ ID NO 356
<211> LENGTH: 66
<212> TYPE: DNA
<213> ORGANISM: Artificial Sequence
<220> FEATURE:
<223> OTHER INFORMATION: synthetic

<400> SEQUENCE: 356
gcgagagaac ggtttggata tagtctcttc gataaggggg tacgctacta ctacggtatg      60
gacgtc                                                                  66

<210> SEQ ID NO 357
<211> LENGTH: 22
<212> TYPE: PRT
<213> ORGANISM: Artificial Sequence
<220> FEATURE:
<223> OTHER INFORMATION: synthetic

<400> SEQUENCE: 357

Ala Arg Glu Arg Phe Gly Tyr Ser Leu Phe Asp Lys Gly Val Arg Tyr
1               5                   10                  15

Tyr Tyr Gly Met Asp Val
            20

<210> SEQ ID NO 358
<211> LENGTH: 321
<212> TYPE: DNA
<213> ORGANISM: Artificial Sequence
<220> FEATURE:
<223> OTHER INFORMATION: synthetic

<400> SEQUENCE: 358

| | | | | | |
|---|---|---|---|---|---|
| gacatccaga | tgacccagtc | tccatcctcc | ctgtctgcat | ctgtaggaga | cagagtcacc | 60 |
| atcacttgcc | gggcaagtca | gggcattaga | aatgatttag | gctggtatca | gcagaaacca | 120 |
| gggaaagccc | ctaagcgcct | gatctatgct | gcatccagtt | tacaaagtgg | ggtcccatca | 180 |
| aggttcagcg | gcagtggatc | tgggacagaa | ttcactctca | caatcagcgg | cctgcagcct | 240 |
| gaagattttg | caacttatta | ctgtctacag | cataatagtt | accctcggac | gttcggccaa | 300 |
| gggaccaagg | tggaaatcaa | a | | | | 321 |

<210> SEQ ID NO 359
<211> LENGTH: 107
<212> TYPE: PRT
<213> ORGANISM: Artificial Sequence
<220> FEATURE:
<223> OTHER INFORMATION: synthetic

<400> SEQUENCE: 359

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Gly Leu Gln Pro
65                  70                  75                  80
Glu Asp Phe Ala Thr Tyr Tyr Cys Leu Gln His Asn Ser Tyr Pro Arg
                85                  90                  95
Thr Phe Gly Gln Gly Thr Lys Val Glu Ile Lys
            100                 105

<210> SEQ ID NO 360
<211> LENGTH: 18
<212> TYPE: DNA
<213> ORGANISM: Artificial Sequence
<220> FEATURE:
<223> OTHER INFORMATION: synthetic

<400> SEQUENCE: 360
cagggcatta gaaatgat       18

<210> SEQ ID NO 361
<211> LENGTH: 6
<212> TYPE: PRT
<213> ORGANISM: Artificial Sequence
<220> FEATURE:
<223> OTHER INFORMATION: synthetic

<400> SEQUENCE: 361

Gln Gly Ile Arg Asn Asp
1               5

<210> SEQ ID NO 362
<211> LENGTH: 9
<212> TYPE: DNA
<213> ORGANISM: Artificial Sequence
<220> FEATURE:

<223> OTHER INFORMATION: synthetic

<400> SEQUENCE: 362 gctgcatcc                                                                9

<210> SEQ ID NO 363
<211> LENGTH: 3
<212> TYPE: PRT
<213> ORGANISM: Artificial Sequence
<220> FEATURE:
<223> OTHER INFORMATION: synthetic

<400> SEQUENCE: 363

Ala Ala Ser
1

<210> SEQ ID NO 364
<211> LENGTH: 27
<212> TYPE: DNA
<213> ORGANISM: Artificial Sequence
<220> FEATURE:
<223> OTHER INFORMATION: synthetic

<400> SEQUENCE: 364
ctacagcata atagttaccc tcggacg                                           27

<210> SEQ ID NO 365
<211> LENGTH: 9
<212> TYPE: PRT
<213> ORGANISM: Artificial Sequence
<220> FEATURE:
<223> OTHER INFORMATION: synthetic

<400> SEQUENCE: 365

Leu Gln His Asn Ser Tyr Pro Arg Thr
1               5

<210> SEQ ID NO 366
<211> LENGTH: 387
<212> TYPE: DNA
<213> ORGANISM: Artificial Sequence
<220> FEATURE:
<223> OTHER INFORMATION: synthetic

<400> SEQUENCE: 366
gaggtgcagc tggaggaatc tggggggaggc ctggtccagc ctgggggggtc cctgagactc    60 tcctgtgcag cctctggatt cacctttact agcttttgga tgagttgggt ccgccaggtt    120
ccagggaagg ggctgcagtg ggtggccaat ataaagcaag atggaactga aaatactat    180 gtggactctg tgaagggccg attcaccatc tccagacaca acgccaagaa ctcactgtat    240
ctgcaaatga acagcctgag agccgaggac acggctgtgt attactgtgc gagagaacgg    300
tttggatata gtctcttcga taaggggggta cgctactact acggtatgga cgtctggggc    360 caagggaccct cggtcaccgt ctcctca                                        387

<210> SEQ ID NO 367
<211> LENGTH: 129
<212> TYPE: PRT
<213> ORGANISM: Artificial Sequence
<220> FEATURE:
<223> OTHER INFORMATION: synthetic

<400> SEQUENCE: 367

Glu Val Gln Leu Glu Glu Ser Gly Gly Gly Leu Val Gln Pro Gly Gly

```
  1               5                  10                 15
Ser Leu Arg Leu Ser Cys Ala Ala Ser Gly Phe Thr Phe Thr Ser Phe
              20                  25                  30

Trp Met Ser Trp Val Arg Gln Val Pro Gly Lys Gly Leu Gln Trp Val
              35                  40                  45

Ala Asn Ile Lys Gln Asp Gly Thr Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
              85                  90                  95

Ala Arg Glu Arg Phe Gly Tyr Ser Leu Phe Asp Lys Gly Val Arg Tyr
            100                 105                 110

Tyr Tyr Gly Met Asp Val Trp Gly Gln Gly Thr Ser Val Thr Val Ser
            115                 120                 125

Ser
```

<210> SEQ ID NO 368
<211> LENGTH: 24
<212> TYPE: DNA
<213> ORGANISM: Artificial Sequence
<220> FEATURE:
<223> OTHER INFORMATION: synthetic

<400> SEQUENCE: 368
ggattcacct ttactagctt ttgg                                   24

<210> SEQ ID NO 369
<211> LENGTH: 8
<212> TYPE: PRT
<213> ORGANISM: Artificial Sequence
<220> FEATURE:
<223> OTHER INFORMATION: synthetic

<400> SEQUENCE: 369

Gly Phe Thr Phe Thr Ser Phe Trp
1               5

<210> SEQ ID NO 370
<211> LENGTH: 24
<212> TYPE: DNA
<213> ORGANISM: Artificial Sequence
<220> FEATURE:
<223> OTHER INFORMATION: synthetic

<400> SEQUENCE: 370
ataaagcaag atggaactga gaaa                                   24

<210> SEQ ID NO 371
<211> LENGTH: 8
<212> TYPE: PRT
<213> ORGANISM: Artificial Sequence
<220> FEATURE:
<223> OTHER INFORMATION: synthetic

<400> SEQUENCE: 371

Ile Lys Gln Asp Gly Thr Glu Lys
1               5

<210> SEQ ID NO 372
<211> LENGTH: 66
<212> TYPE: DNA

```
<213> ORGANISM: Artificial Sequence
<220> FEATURE:
<223> OTHER INFORMATION: synthetic

<400> SEQUENCE: 372
gcgagagaac ggtttggata tagtctcttc gataaggggg tacgctacta ctacggtatg    60
gacgtc                                                              66

<210> SEQ ID NO 373
<211> LENGTH: 22
<212> TYPE: PRT
<213> ORGANISM: Artificial Sequence
<220> FEATURE:
<223> OTHER INFORMATION: synthetic

<400> SEQUENCE: 373

Ala Arg Glu Arg Phe Gly Tyr Ser Leu Phe Asp Lys Gly Val Arg Tyr
1               5                   10                  15

Tyr Tyr Gly Met Asp Val
            20

<210> SEQ ID NO 374
<211> LENGTH: 321
<212> TYPE: DNA
<213> ORGANISM: Artificial Sequence
<220> FEATURE:
<223> OTHER INFORMATION: synthetic

<400> SEQUENCE: 374
gacatccaga tgacccagtc tccatcctcc ctgtctgcat ctgtaggaga cagagtcacc    60
atcacttgcc gggcaagtca gggcattaga aatgatttag ctggtatca gcagaaacca   120 gggaaagccc ctaagcgcct gatctatgct gcatccagtt tacaaagtgg ggtcccatca   180
aggttcagcg gcagtggatc tgggacagaa ttcactctca caatcagcgg cctgcagcct   240
gaagattttg caacttatta ctgtctacag cataatagtt accctcggac gttcggccaa   300
gggaccaagg tggaaatcaa a                                             321

<210> SEQ ID NO 375
<211> LENGTH: 107
<212> TYPE: PRT
<213> ORGANISM: Artificial Sequence
<220> FEATURE:
<223> OTHER INFORMATION: synthetic

<400> SEQUENCE: 375

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys
            100                 105
```

<210> SEQ ID NO 376
<211> LENGTH: 18
<212> TYPE: DNA
<213> ORGANISM: Artificial Sequence
<220> FEATURE:
<223> OTHER INFORMATION: synthetic

<400> SEQUENCE: 376
cagggcatta gaaatgat                                                     18

<210> SEQ ID NO 377
<211> LENGTH: 6
<212> TYPE: PRT
<213> ORGANISM: Artificial Sequence
<220> FEATURE:
<223> OTHER INFORMATION: synthetic

<400> SEQUENCE: 377

Gln Gly Ile Arg Asn Asp
1               5

<210> SEQ ID NO 378
<211> LENGTH: 9
<212> TYPE: DNA
<213> ORGANISM: Artificial Sequence
<220> FEATURE:
<223> OTHER INFORMATION: synthetic

<400> SEQUENCE: 378 gctgcatcc                                                                9

<210> SEQ ID NO 379
<211> LENGTH: 3
<212> TYPE: PRT
<213> ORGANISM: Artificial Sequence
<220> FEATURE:
<223> OTHER INFORMATION: synthetic

<400> SEQUENCE: 379

Ala Ala Ser
1

<210> SEQ ID NO 380
<211> LENGTH: 27
<212> TYPE: DNA
<213> ORGANISM: Artificial Sequence
<220> FEATURE:
<223> OTHER INFORMATION: synthetic

<400> SEQUENCE: 380
ctacagcata atagttaccc tcggacg                                           27

<210> SEQ ID NO 381
<211> LENGTH: 9
<212> TYPE: PRT
<213> ORGANISM: Artificial Sequence
<220> FEATURE:
<223> OTHER INFORMATION: synthetic

<400> SEQUENCE: 381

Leu Gln His Asn Ser Tyr Pro Arg Thr
1               5

<210> SEQ ID NO 382
<211> LENGTH: 8
<212> TYPE: PRT

<213> ORGANISM: Artificial Sequence
<220> FEATURE:
<223> OTHER INFORMATION: synthetic
<220> FEATURE:
<221> NAME/KEY: VARIANT
<222> LOCATION: 5
<223> OTHER INFORMATION: Xaa = S, N or T
<220> FEATURE:
<221> NAME/KEY: VARIANT
<222> LOCATION: 6
<223> OTHER INFORMATION: Xaa = S or N
<220> FEATURE:
<221> NAME/KEY: VARIANT
<222> LOCATION: 7
<223> OTHER INFORMATION: Xaa = F or Y

<400> SEQUENCE: 382

Gly Phe Thr Phe Xaa Xaa Xaa Trp
1               5

<210> SEQ ID NO 383
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 6
<223> OTHER INFORMATION: Xaa = T or S
<220> FEATURE:
<221> NAME/KEY: VARIANT
<222> LOCATION: 8
<223> OTHER INFORMATION: Xaa = R or K

<400> SEQUENCE: 383

Ile Lys Gln Asp Gly Xaa Glu Xaa
1               5

<210> SEQ ID NO 384
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 3
<223> OTHER INFORMATION: Xaa = D or E
<220> FEATURE:
<221> NAME/KEY: VARIANT
<222> LOCATION: 9
<223> OTHER INFORMATION: Xaa = F, V or L
<220> FEATURE:
<221> NAME/KEY: VARIANT
<222> LOCATION: 10
<223> OTHER INFORMATION: Xaa = F or Y

<400> SEQUENCE: 384

Ala Arg Xaa Arg Phe Gly Tyr Ser Xaa Xaa Asp Lys Gly Val Arg Tyr
1               5                   10                  15

Tyr Tyr Gly Met Asp Val
            20

<210> SEQ ID NO 385
<211> LENGTH: 3
<212> TYPE: PRT
<213> ORGANISM: Artificial Sequence
<220> FEATURE:
<223> OTHER INFORMATION: synthetic
<220> FEATURE:
<221> NAME/KEY: VARIANT

```
<222> LOCATION: 2
<223> OTHER INFORMATION: Xaa = A or T

<400> SEQUENCE: 385

Ala Xaa Ser
1

<210> SEQ ID NO 386
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 4
<223> OTHER INFORMATION: Xaa = N or K

<400> SEQUENCE: 386

Leu Gln His Xaa Ser Tyr Pro Arg Thr
1               5

<210> SEQ ID NO 387
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 3
<223> OTHER INFORMATION: Xaa = D or E
<220> FEATURE:
<221> NAME/KEY: VARIANT
<222> LOCATION: 9
<223> OTHER INFORMATION: Xaa = F, V, L or A
<220> FEATURE:
<221> NAME/KEY: VARIANT
<222> LOCATION: 10
<223> OTHER INFORMATION: Xaa = F or Y

<400> SEQUENCE: 387

Ala Arg Xaa Arg Phe Gly Tyr Ser Xaa Xaa Asp Lys Gly Val Arg Tyr
1               5                   10                  15

Tyr Tyr Gly Met Asp Val
            20
```